US011351240B2

United States Patent
Dallmeier et al.

(10) Patent No.: US 11,351,240 B2
(45) Date of Patent: Jun. 7, 2022

(54) CHIMERIC YELLOW FEVER ZIKA VIRUS STRAIN

(71) Applicant: KATHOLIEKE UNIVERSITEIT LEUVEN, Leuven (BE)

(72) Inventors: Kai Dallmeier, Kessel-Lo (BE); Dieudonné Buh Kum, Aarschot (BE); Niraj Mishra, Leuven (BE); Johan Neyts, Kessel-Lo (BE); Michael Alexander Schmid, Lumino (CH)

(73) Assignee: Katholieke Universiteit Leuven, Leuven (BE)

( * ) Notice: Subject to any disclaimer, the term of this patent is extended or adjusted under 35 U.S.C. 154(b) by 0 days.

(21) Appl. No.: 16/652,705

(22) PCT Filed: Oct. 5, 2018

(86) PCT No.: PCT/EP2018/077167
§ 371 (c)(1),
(2) Date: Apr. 1, 2020

(87) PCT Pub. No.: WO2019/068885
PCT Pub. Date: Apr. 11, 2019

(65) Prior Publication Data
US 2020/0316187 A1 Oct. 8, 2020

(30) Foreign Application Priority Data

Oct. 5, 2017 (GB) ..................................... 1716307

(51) Int. Cl.
*A61K 39/12* (2006.01)
*C07K 14/005* (2006.01)
*C12N 7/00* (2006.01)
*A61K 39/00* (2006.01)

(52) U.S. Cl.
CPC ............ *A61K 39/12* (2013.01); *C07K 14/005* (2013.01); *C12N 7/00* (2013.01); *A61K 2039/5254* (2013.01); *C12N 2770/00034* (2013.01); *C12N 2770/24121* (2013.01); *C12N 2770/24122* (2013.01); *C12N 2770/24134* (2013.01); *C12N 2770/24143* (2013.01)

(58) Field of Classification Search
None
See application file for complete search history.

(56) References Cited

FOREIGN PATENT DOCUMENTS

| WO | 2005042014 A1 | 5/2005 |
|---|---|---|
| WO | 2006116182 A1 | 11/2006 |
| WO | 2014174078 A1 | 10/2014 |
| WO | 2018060771 A1 | 4/2018 |

OTHER PUBLICATIONS

GenBank Accession No. EU545988.1 (2008). (Year: 2008).*
International Search Report in reference to co-pending European Patent Application No. PCT/EP2018/077167 filed Oct. 5, 2018.
Written Opinion in reference to co-pending European Patent Application No. PCT/EP2018/077167 filed Oct. 5, 2018.
Arroyo, et al., "Molecular Basis for Attentuation of Neurovirulence of a Yellow Fever Virus/Japenese Encephalitis Virus Chimera Vaccine (ChimeriVax-JE)", Journal of Virology, vol. 75, No. 2, pp. 934-942, Jan. 2001.
Cicin-Sain, et al., "Vaccination of Mice with Bacteria Carrying a Cloned Herpesvirus Genome Reconstituted In Vivo", Journal of Virology, vol. 77, No. 15, pp. 8249-8255, Aug. 2003.
Darji, et al., "Oral delivery of DNA vaccines using attenuated *Salmonella typhimurium* as carrier", FEMS Immunology and medical Microbiology, vol. 27, pp. 341-349, 2000.
Fischl, et al., "High-Throughput Screening Using Dengue Virus Reporter Genomes", Chapter 17, vol. 1030, pp. 205-219, 2013.
Giel-Moloney, et al., "Chimeric yellow fever 17D-Zika virus (ChimeriVax-Zika) as a live-attenuated Zika virus vaccine", Scientific Reports, pp. 1-11, 2018.
Grant, et al., "A Single Amino Acid in nonstructural Protein NS4B Confers Virulence to Dengue Virus in AG129 Mice through Enhancement of Viral RNA Synthesis", Journal of Virology, vol. 85, No. 15, pp. 7775-7787, Aug. 2011.
Guirakhoo, et al., "Immunogenicity, Genetic Stability, and Protective Efficacy of a Recombinant, Chimeric Yellow Fever-Japanese Encephalitis Virus (ChimerVax-JE) as a Live, Attentuated Vaccine Candidate against Japanese Encephalitis", Virology, vol. 257, pp. 363-372, 1999.
Khou, et al., "Identifying Attenuating Mutations: Tools for a New Vaccine Design against Flaviviruses", Intervirology, pp. 8-18, 2017.
Lee, et al., "Mutagenesis of the Signal Sequence of Yellow Fever Virus prM Protein: Enhancement of Signalase Cleavage In Vitro Is Lethal for Virus Production", Journal of Virology, vol. 74, No. 1, pp. 24-32, Jan. 2000.
Lobigs, et al., "Inefficient Signalase Cleavage Promotes Efficient Nucleocapsid Incorporation into Budding Flavivirus Membranes", Journal of Virology, vol. 78, No. 1, pp. 178-186, Jan. 2004.
Schlesinger, et al., "Monoclonal Antibodies Distinguish between Wild and Vaccine Strains of Yellow Fever Virus by Neutralization, Hemagglutination Inhibition, and Immune Precipitation of the Virus Envelope Protein", Virology, vol. 125, pp. 8-17, 1983.
Seligman, et al., "Risk groups for yellow fever vaccine-associated viscerotropic disease (YEL-AVD)", Vaccine, vol. 32, pp. 5769-5775, 2014.
Shan, et al., "A single-dose live-attenuated vaccine prevents Zika virus pregnancy transmission and testis damage", Nature Communications, pp. 1-9, 2017.

(Continued)

*Primary Examiner* — Stacy B Chen

(74) *Attorney, Agent, or Firm* — Dinsmore & Shohl LLP

(57) ABSTRACT

The present invention relates to chimeric yellow fever—Zika strains and attenuated versions thereof, wherein the nucleotide sequence encoding the signal sequence and prME protein of said yellow virus is replaced by a nucleotide sequence encoding the signal sequence and the prME protein of a Zika virus.

20 Claims, 22 Drawing Sheets

Figure 5:
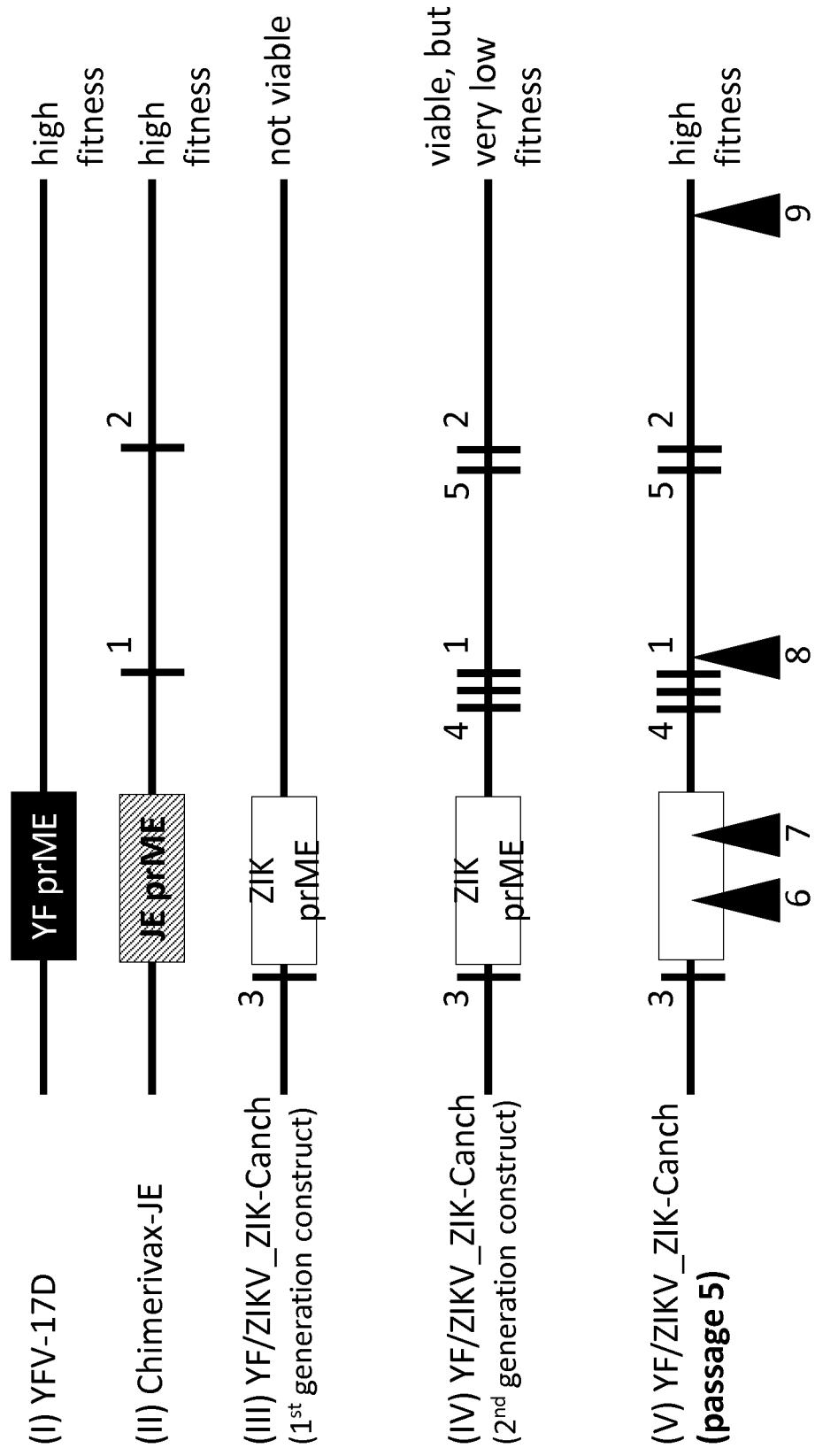

Specification includes a Sequence Listing.

(56) References Cited

OTHER PUBLICATIONS

Tan, et al., "A Non Mouse-Adapted Dengue Virus Strain as a New Model of Severe Dengue Infection in AG129 Mice", PLOS Neglected Tropical Diseases, vol. 4, Issue 4, pp. 1-10, Apr. 2010.

Touret, et al., "Live Zika virus chimeric vaccine candidate based on a yellow fever 17-D attenuated backbone", Emerging Microbes & Infections, pp. 1-12, 2018.

Xie, et al., "Understanding Zika Virus Stability and Developing a Chimeric Vaccine through Functional Analysis", American Society for Microbiology, vol. 8, Issue 1, pp. 1-14, Jan. 2017.

Yuan, et al., "A single mutation in the prM protein of Zika virus contributes to fetal microcephaly", Research, vol. 358, pp. 1-4, Nov. 17, 2017.

Zmurko, et al., "The Viral Polymerase Inhibitor 7-Deaza-2'-C-Methyladenosine Is a Potent Inhibitor of In Vitro Zika Virus Replication and Delays Disease Progression in a Robust Mouse Infection Model", PLOS Neglected Tropical Diseases, pp. 1-15, May 10, 2016.

* cited by examiner (SEQ ID NO:1) AGTAAATCCTGTGTGCTAATTGAGGTGCATTGGTCTGCAAATCGAGTTGCTAGGCAATAA
ACACATTTGGATTAATTTTAATCGTTCGTTGAGCGATTAGCAGAGAACTGACCAGAAC
ATGTCTGGTCGTAAAGCTCAGGGAAAAACCCTGGGCGTCAATATGGTACGACGAGGAGTT
(SEQ ID NO:2)  M  S  G  R  K  A  Q  G  K  T  L  G  V  N  M  V  R  R  G  V
CGCTCCTTGTCAAACAAAATAAAACAAAAAACAAAACAAATTGGAAACAGACCTGGACCT
 R  S  L  S  N  K  I  K  Q  K  T  K  Q  I  G  N  R  P  G  P
TCAAGAGGTGTTCAAGGATTTATCTTTTTCTTTTTGTTCAACATTTTGACTGGAAAAAAG
 S  R  G  V  Q  G  F  I  F  F  F  L  F  N  I  L  T  G  K  K
ATCACAGCCCACCTAAAGAGGTTGTGGAAAATGCTGGACCCAAGACAAGGCTTGGCTGTT
 I  T  A  H  L  K  R  L  W  K  M  L  D  P  R  Q  G  L  A  V
                                                  409[409]
CTAAGGAAAGTCAAGAGAGTGGTGGCCAGTTTGATGAGAGGATTGTCCTCG³AGGAAACGC
 L  R  K  V  K  R  V  V  A  S  L  M  R  G  L  S  S  R  K  R
                                                   97
CGT ggcacagatactagtgtcggaattgttggcctcctgctgaccacagccatggcagtg
 R   G  T  D  T  S  V  G  I  V  G  L  L  L  T  T  A  M  A  V
gaggtcactagacgtgggagtgcatactatatgtacttggacagaagcgatgctggggag
 E  V  T  R  R  G  S  A  Y  Y  M  Y  L  D  R  S  D  A  G  E
gccatatcttttccaaccacactggggatgaacaagtgttacatacagatcatggatctt
 A  I  S  F  P  T  T  L  G  M  N  K  C  Y  I  Q  I  M  D  L
ggacacatgtgtgatgccaccatgagctatgaatgccctatgttggatgaggggtagaa
 G  H  M  C  D  A  T  M  S  Y  E  C  P  M  L  D  E  G  V  E
ccagatgacgtcgattgttggtgcaacacgacatcaacttgggttgtgtacggaacctgc
 P  D  D  V  D  C  W  C  N  T  T  S  T  W  V  V  Y  G  T  C
caccacaaaaaggtgaagcacggagatctagaagagctgtgacgctcccctcccattcc
 H  H  K  K  G  E  A  R  R  S  R  R  A  V  T  L  P  S  H  S
actaggaagctgcaaacgcggtcgcagacctggttggaatcaagagaatatacaaagcac
 T  R  K  L  Q  T  R  S  Q  T  W  L  E  S  R  E  Y  T  K  H
ctgattagagtcgaaaattggatattcaggaaccctggcttcgcgttagcagcagctgcc
 L  I  R  V  E  N  W  I  F  R  N  P  G  F  A  L  A  A  A  A
atcgcctggcttttgggaagttcaacgagccaaaaagtcatatacttggtcatgatactg
 I  A  W  L  L  G  S  S  T  S  Q  K  V  I  Y  L  V  M  I  L
ctgattgccccggcatacagcatcaggtgcataggagtcagcaatagggactttgtggaa
 L  I  A  P  A  Y  S  I  R  C  I  G  V  S  N  R  D  F  V  E
ggtatgtcaggtgggacttgggttgatgttgtcttggaacatggaggttgtgttaccgta
 G  M  S  G  G  T  W  V  D  V  V  L  E  H  G  G  C  V  T  V
                   1097[1097]
atggcacaggacaaaccgN⁶ctgtcgacatagagctggttacaacaacagtcagcaacatg
 M  A  Q  D  K  P  T  V  D  I  E  L  V  T  T  T  V  S  N  M
                   ‾‾‾
                   327
gcggaggtaagatcctattgctatgaggcatcaatatcggacatggcttcggacagccgc
 A  E  V  R  S  Y  C  Y  E  A  S  I  S  D  M  A  S  D  S  R
tgcccaacacaaggtgaagcctaccttgacaagcagtcagacactcaatatgtctgcaaa
 C  P  T  Q  G  E  A  Y  L  D  K  Q  S  D  T  Q  Y  V  C  K
agaacgttagtggacagaggctggggaaatggatgtggacttttttggcaaagggagcctg
 R  T  L  V  D  R  G  W  G  N  G  C  G  L  F  G  K  G  S  L
gtgacatgcgctaagtttgcatgctccaagaaaatgaccgggaagagcatccagccagag
 V  T  C  A  K  F  A  C  S  K  K  M  T  G  K  S  I  Q  P  E
aatctggagtaccggataatgctgtcagttcatggctcccagcacagtgggatgatcgtt
 N  L  E  Y  R  I  M  L  S  V  H  G  S  Q  H  S  G  M  I  V

FIGURE 1

(SEQ ID NO:1 (cont.)) aatgacacaggacatgaaactgatgagaatagagcgaaggttgagataacgcccaattca
(SEQ ID NO:2 (cont.)) N  D  T  G  H  E  T  D  E  N  R  A  K  V  E  I  T  P  N  S
ccaagagctgaagccaccctggggggttttggaagcctaggacttgattgtgaaccgagg
P  R  A  E  A  T  L  G  G  F  G  S  L  G  L  D  C  E  P  R
acaggccttgacttttcagatttgtattacttgactatgaataacaagcactggttggtt
T  G  L  D  F  S  D  L  Y  Y  L  T  M  N  N  K  H  W  L  V
cacaaggagtggttccacgacattccattaccttggcatgctggggcagacaccggaact
H  K  E  W  F  H  D  I  P  L  P  W  H  A  G  A  D  T  G  T
ccacattggaacaacaaagaagcattggtagagttcaaggacgcacatgccaaaaggcaa
P  H  W  N  N  K  E  A  L  V  E  F  K  D  A  H  A  K  R  Q
actgtcgtggttctagggagtcaagaaggagcagttcacacggcccttgctggagctctg
T  V  V  V  L  G  S  Q  E  G  A  V  H  T  A  L  A  G  A  L
gaggctgagatggatggtgcaaagggaaggctgtcctctggccacttgaaatgtcgcctg
E  A  E  M  D  G  A  K  G  R  L  S  S  G  H  L  K  C  R  L
aaaatggataaacttagattgaaggggcgtgtcatactccttgtgtaccgcagcgttcaca
K  M  D  K  L  R  L  K  G  V  S  Y  S  L  C  T  A  A  F  T
ttcaccaagatcccggctgaaacactgcacgggacagtcacagtggaggtacagtacgca
F  T  K  I  P  A  E  T  L  H  G  T  V  T  V  E  V  Q  Y  A
gggacagatggaccctgcaaggttccagctcagatggcggtggacatgcaaactctgacc
G  T  D  G  P  C  K  V  P  A  Q  M  A  V  D  M  Q  T  L  T
ccagttgggaggctgataaccgctaaccctgtaatcactgaaagcactgagaactctaag
P  V  G  R  L  I  T  A  N  P  V  I  T  E  S  T  E  N  S  K
atgatgctggaacttgatccaccatttggggactcttacattgtcataggagtcggggag
M  M  L  E  D  P  P  F  G  D  S  Y  I  V  I  G  V  G  E
aagaagatcacccatcactggcacaggagtggcagcaccattggaaaagcatttgaagcc
K  K  I  T  H  H  W  H  R  S  G  S  T  I  G  K  A  F  E  A
actgtgagaggtgccaagagaatggcagtcttgggagacacagcctgggattttggatca
T  V  R  G  A  K  R  M  A  V  L  G  D  T  A  W  D  F  G  S
gttggaggtgctctcaactcattgggcaagggcatccatcaaattttggagcagctttc
V  G  G  A  L  N  S  L  G  K  G  I  H  Q  I  F  G  A  A  F
    2343[2343]
aaatt7attgtttggaggaatgtcctggttctcacaaattctcattggaacgttgctggtg
K  L  L  F  G  G  M  S  W  F  S  Q  I  L  I  G  T  L  L  V
    742
tggttgggtctgaatacaaagaatggatctatttcccttacgtgcttggccttaggggga
W  L  G  L  N  T  K  N  G  S  I  S  L  T  C  L  A  L  G  G
gtgttgatcttttatccacagccgtctctgcGGGCGCCGATCAAGGATGCGCCATCAAC
V  L  I  F  L  S  T  A  V  S  A  G  A  D  Q  G  C  A  I  N
TTTGGCAAGAGAGAGCTCAAGTGCGGAGATGGTATCTTCATATTTAGAGACTCTGATGAC
F  G  K  R  E  L  K  C  G  D  G  I  F  I  F  R  D  S  D  D
TGGCTGAACAAGTACTCATACTATCCAGAAGATCCTGTGAAGCTTGCATCAATAGTGAAA
W  L  N  K  Y  S  Y  Y  P  E  D  P  V  K  L  A  S  I  V  K
GCCTCTTTTGAAGAAGGGAAGTGTGGCCTAAATTCAGTTGACTCCCTTGAGCATGAGATG
A  S  F  E  E  G  K  C  G  L  N  S  V  D  S  L  E  H  E  M
TGGAGAAGCAGGGCAGATGAGATCAATGCCATTTTTGAGGAAAACGAGGTGGACATTTCT
W  R  S  R  A  D  E  I  N  A  I  F  E  E  N  E  V  D  I  S
GTTGTCGTGCAGGATCCAAAGAATGTTTACCAGAGAGGAACTCATCCATTTTCCAGAATT
V  V  V  Q  D  P  K  N  V  Y  Q  R  G  T  H  P  F  S  R  I
CGGGATGGTCTGCAGTATGGTTGGAAGACTTGGGGTAAGAACCTTGTGTTCTCCCCAGGG
R  D  G  L  Q  Y  G  W  K  T  W  G  K  N  L  V  F  S  P  G FIGURE 1 (continued)

(SEQ ID NO:1 (cont.)) AGGAAGAATGGAAGCTTCATCATAGATGGAAAGTCCAGGAAAGAATGCCCGTTTTCAAAC
(SEQ ID NO:2 (cont.)) R  K  N  G  S  F  I  I  D  G  K  S  R  K  E  C  P  F  S  N CGGGTCTGGAATTCTTTCCAGATAGAGGAGTTTGGGACGGGAGTGTTCACCACACGCGTG
R  V  W  N  S  F  Q  I  E  E  F  G  T  G  V  F  T  T  R  V TACATGGACGCAGTCTTTGAATACACCATAGACTGCGATGGATCTATCTTGGGTGCAGCG
Y  M  D  A  V  F  E  Y  T  I  D  C  D  G  S  I  L  G  A  A GTGAACGGAAAAAAGAGTGCCCATGGCTCTCCAACATTTTGGATGGGAAGTCATGAAGTA
V  N  G  K  K  S  A  H  G  S  P  T  F  W  M  G  S  H  E  V AATGGGACATGGATGATCCACACCTTGGAGGCATTAGATTACAAGGAGTGTGAGTGGCCA
N  G  T  W  M  I  H  T  L  E  A  L  D  Y  K  E  C  E  W  P CTGACACATACGATTGGAACATCAGTTGAAGAGAGTGAAATGTTCATGCCGAGATCAATC
L  T  H  T  I  G  T  S  V  E  E  S  E  M  F  M  P  R  S  I GGAGGCCCAGTTAGCTCTCACAATCATATCCCTGGATACAAGGTTCAGACGAACGGACCT
G  G  P  V  S  S  H  N  H  I  P  G  Y  K  V  Q  T  N  G  P TGGATGCAGGTACCACTAGAAGTGAAGAGAGAAGCTTGCCCAGGGACTAGCGTGATCATT
W  M  Q  V  P  L  E  V  K  R  E  A  C  P  G  T  S  V  I  I GATGGCAACTGTGATGGACGGGGAAAATCAACCAGATCCACCACGGATAGCGGGAAAGTT
D  G  N  C  D  G  R  G  K  S  T  R  S  T  T  D  S  G  K  V ATTCCTGAATGGTGTTGCCGCTCCTGCACAATGCCGCCTGTGAGCTTCCATGGTAGTGAT
I  P  E  W  C  C  R  S  C  T  M  P  P  V  S  F  H  G  S  D GGGTGTTGGTATCCCATGGAAATTAGGCCAAGGAAAACGCATGAAAGCCATCTGGTGCGC
G  C  W  Y  P  M  E  I  R  P  R  K  T  H  E  S  H  L  V  R TCCTGGGTTACAGCTGGAGAAATACATGCTGTCCCTTTTGGTTTGGTGAGCATGATGATA
S  W  V  T  A  G  E  I  H  A  V  P  F  G  L  V  S  M  M  I GCAATGGAAGTGGTCCTAAGGAAAAGACAGGGACCAAAGCAAATGTTGGTTGGAGGAGTA
A  M  E  V  V  L  R  K  R  Q  G  P  K  Q  M  L  V  G  G  V GTGCTCTTGGGAGCAATGCTGGTCGGGCAAGTAACTCTCCTTGATTTGCTGAAACTCACA
V  L  L  G  A  M  L  V  G  Q  V  T  L  L  D  L  L  K  L  T GTGGCTGTGGGATTGCATTTCCATGAGATGAACAATGGAGGAGACGCCATGTATATGGCG
V  A  V  G  L  H  F  H  E  M  N  N  G  G  D  A  M  Y  M  A TTGATTGCTGCCTTTTCAATCAGACCAGGGCTGCTCATCGGCTTTGGGCTCAGGACCCTA
L  I  A  A  F  S  I  R  P  G  L  L  I  G  F  G  L  R  T  L TGGAGCCCTCGGGAACGCCTTGTGCTGACCCTAGGAGCAGCCATGGTGGAGATTGCCTTG
W  S  P  R  E  R  L  V  L  T  L  G  A  A  M  V  E  I  A  L GGTGGCGTGATGGGCGGCCTGTGGAAGTATCTAAATGCAGTTTCTCTCTGCATCCTGACA
G  G  V  M  G  G  L  W  K  Y  L  N  A  V  S  L  C  I  L  T ATAAATGCTGTTGCTTCTAGGAAAGCATCAAATACCATCTTGCCCCTCATGGCTCTGTTG
I  N  A  V  A  S  R  K  A  S  N  T  I  L  P  L  M  A  L  L
   3979    3985                                        4025
   [4024]  [4030]                                      [4070]
ACACCG⁴GTCACC⁴ATGGCTGAGGTGAGACTTGCCGCAATGTTCTTTTGTGCCA¹TGGTTATC
T  P  V  T  M  A  E  V  R  L  A  A  M  F  F  C  A  <u>M</u>  V  I
   1302    1304                                        1318

ATAGGGGTCCTTCACCAGAATTTCAAGGACACCTCCATGCAGAAGACTATACCTCTGGTG
I  G  V  L  H  Q  N  F  K  D  T  S  M  Q  K  T  I  P  L  V

GCCCTCACACTCACATCTTACCTGGGCTTGACACAACCTTTTTTGGGCCTGTGTGCATTT
A  L  T  L  T  S  Y  L  G  L  T  Q  P  F  L  G  L  C  A  F

CTGGCAACCCGCATATTTGGGCGAAGGAGTATCCCAGTGAATGAGGCACTCGCAGCAGCT
L  A  T  R  I  F  G  R  R  S  I  P  V  N  E  A  L  A  A  A

FIGURE 1 (continued)

(SEQ ID NO:1 (cont.)) GGTCTAGTGGGAGTGCTGGCAGGACTGGCTTTTCAGGAGATGGAGAACTTCCTTGGTCCG
(SEQ ID NO:2 (cont.)) G   L   V   G   V   L   A   G   L   A   F   Q   E   M   E   N   F   L   G   P
ATTGCAGTTGGAGGACTCCTGATGATGCTGGTTAGCGTGGCTGGGAGGGTGGATGGGCTA
I   A   V   G   G   L   L   M   M   L   V   S   V   A   G   R   V   D   G   L
GAGCTCAAGAAGCTTGGTGAAGTTTCATGGGAAGAGGAGGCGGAGATCAGCGGGAGTTCC
E   L   K   K   L   G   E   V   S   W   E   E   E   A   E   I   S   G   S   S
GCCCGCTATGATGTGGCACTCAGTGAACAAGGGGAGTTCAAGCTGCTTTCTGAAGAGAAA
A   R   Y   D   V   A   L   S   E   Q   G   E   F   K   L   L   S   E   E   K
GTGCCATGGGACCAGGTTGTGATGACCTCGCTGGCCTTGGTTGGGGCTGCCCTCCATCCA
V   P   W   D   Q   V   V   M   T   S   L   A   L   V   G   A   A   L   H   P
TTTGCTCTTCTGCTGGTCCTTGCTGGGTGGCTGTTTCATGTCAGGGGAGCTAGGAGAAGT
F   A   L   L   L   V   L   A   G   W   L   F   H   V   R   G   A   R   R   S
GGGGATGTCTTGTGGGATATTCCCACTCCTAAGATCATCGAGGAATGTGAACATCTGGAG
G   D   V   L   W   D   I   P   T   P   K   I   I   E   E   C   E   H   L   E
GATGGGATTTATGGCATATTCCAGTCAACCTTCTTGGGGCCTCCCAGCGAGGAGTGGGA
D   G   I   Y   G   I   F   Q   S   T   F   L   G   A   S   Q   R   G   V   G
GTGGCACAGGGAGGGGTGTTCCACACAATGTGGCATGTCACAAGAGGAGCTTTCCTTGTC
V   A   Q   G   G   V   F   H   T   M   W   H   V   T   R   G   A   F   L   V
AGGAATGGCAAGAAGTTGATTCCATCTTGGGCTTCAGTAAAGGAAGACCTTGTCGCCTAT
R   N   G   K   K   L   I   P   S   W   A   S   V   K   E   D   L   V   A   Y
GGTGGCTCATGGAAGTTGGAAGGCAGATGGGATGGAGAGGAAGAGGTCCAGTTGATCGCG
G   G   S   W   K   L   E   G   R   W   D   G   E   E   E   V   Q   L   I   A
GCTGTTCCAGGAAAGAACGTGGTCAACGTCCAGACAAAACCGAGCTTGTTCAAAGTGAGG
A   V   P   G   K   N   V   V   N   V   Q   T   K   P   S   L   F   K   V   R
AATGGGGGAGAAATCGGGGCTGTCGCTCTTGACTATCCGAGTGGCACTTCAGGATCTCCT
N   G   G   E   I   G   A   V   A   L   D   Y   P   S   G   T   S   G   S   P
ATTGTTAACAGGAACGGAGAGGTGATTGGGCTGTACGGCAATGGCATCCTTGTCGGTGAC
I   V   N   R   N   G   E   V   I   G   L   Y   G   N   G   I   L   V   G   D
AACTCCTTCGTGTCCGCCATATCCCAGACTGAGGTGAAGGAAGAAGGAAAGGAGGAGCTC
N   S   F   V   S   A   I   S   Q   T   E   V   K   E   E   G   K   E   E   L
CAAGAGATCCCGACAATGCTAAAGAAAGGAATGACAACTGTCCTTGATTTTCATCCTGGA
Q   E   I   P   T   M   L   K   K   G   M   T   T   V   L   D   F   H   P   G
GCTGGGAAGACAAGACGTTTCCTCCCACAGATCTTGGCCGAGTGCGCACGGAGACGCTTG
A   G   K   T   R   R   F   L   P   Q   I   L   A   E   C   A   R   R   R   L
CGCACTCTTGTGTTGGCCCCCACCAGGGTTGTTCTTTCTGAAATGAAGGAGGCTTTTCAC
R   T   L   V   L   A   P   T   R   V   V   L   S   E   M   K   E   A   F   H
GGCCTGGACGTGAAATTCCACACACAGGCTTTTTCCGCTCACGGCAGCGGGAGAGAAGTC
G   L   D   V   K   F   H   T   Q   A   F   S   A   H   G   S   G   R   E   V
ATTGATGCCATGTGCCATGCCACCCTAACTTACAGGATGTTGGAACCAACTAGGGTTGTT
I   D   A   M   C   H   A   T   L   T   Y   R   M   L   E   P   T   R   V   V
AACTGGGAAGTGATCATTATGGATGAAGCCCATTTTTTGGATCCAGCTAGCATAGCCGCT
N   W   E   V   I   I   M   D   E   A   H   F   L   D   P   A   S   I   A   A
AGAGGTTGGGCAGCGCACAGAGCTAGGGCAAATGAAAGTGCAACAATCTTGATGACAGCC
R   G   W   A   A   H   R   A   R   A   N   E   S   A   T   I   L   M   T   A ACACCGCCTGGGACTAGTGATGAATTTCCACATTCAAATGGTGAAATAGAAGATGTTCAA
T   P   P   G   T   S   D   E   F   P   H   S   N   G   E   I   E   D   V   Q

5641[5686]

FIGURE 1 (continued)

(SEQ ID NO:1 (cont.)) ACGGACATACCCAGTGAGCCCTGGAACACAGGGCATGACTGGATCCT`G⁸`GCTGACAAAAGG
(SEQ ID NO:2 (cont.)) T   D   I   P   S   E   P   W   N   T   G   H   D   W   I   L   A   D   K   R
                                                                                            1856
CCCACGGCATGGTTCCTTCCATCCATCAGAGCTGCAAATGTCATGGCTGCCTCTTTGCGT
P   T   A   W   F   L   P   S   I   R   A   A   N   V   M   A   A   S   L   R
AAGGCTGGAAAGAGTGTGGTGGTCCTGAACAGGAAAACCTTTGAGAGAGAATACCCCACG
K   A   G   K   S   V   V   V   L   N   R   K   T   F   E   R   E   Y   P   T
ATAAAGCAGAAGAAACCTGACTTTATATTGGCCACTGACATAGCTGAAATGGGAGCCAAC
I   K   Q   K   K   P   D   F   I   L   A   T   D   I   A   E   M   G   A   N
CTTTGCGTGGAGCGAGTGCTGGATTGCAGGACGGCTTTTAAGCCTGTGCTTGTGGATGAA
L   C   V   E   R   V   L   D   C   R   T   A   F   K   P   V   L   V   D   E
GGGAGGAAGGTGGCAATAAAAGGGCCACTTCGTATCTCCGCATCCTCTGCTGCTCAAAGG
G   R   K   V   A   I   K   G   P   L   R   I   S   A   S   S   A   A   Q   R
AGGGGGCGCATTGGAGAAATCCCAACAGAGATGGAGACTCATACTACTATTCTGAGCCT
R   G   R   I   G   R   N   P   N   R   D   G   D   S   Y   Y   Y   S   E   P
ACAAGTGAAAATAATGCCCACCACGTCTGCTGGTTGGAGGCCTCAATGCTCTTGGACAAC
T   S   E   N   N   A   H   H   V   C   W   L   E   A   S   M   L   L   D   N
ATGGAGGTGAGGGGTGGAATGGTCGCCCCACTCTATGGCGTTGAAGGAACTAAAACACCA
M   E   V   R   G   G   M   V   A   P   L   Y   G   V   E   G   T   K   T   P
GTTTCCCCTGGTGAAATGAGACTGAGGGATGACCAGAGGAAAGTCTTCAGAGAACTAGTG
V   S   P   G   E   M   R   L   R   D   D   Q   R   K   V   F   R   E   L   V
AGGAATTGTGACCTGCCCGTTTGGCTTTCGTGGCAAGTGGCCAAGGCTGGTTTGAAGACG
R   N   C   D   L   P   V   W   L   S   W   Q   V   A   K   A   G   L   K   T
AATGATCGTAAGTGGTGTTTTGAAGGCCCTGAGGAACATGAGATCTTGAATGACAGCGGT
N   D   R   K   W   C   F   E   G   P   E   E   H   E   I   L   N   D   S   G
GAAACAGTGAAGTGCAGGGCTCCTGGAGGAGCAAAGAAGCCTCTGCGCCCAAGGTGGTGT
E   T   V   K   C   R   A   P   G   G   A   K   K   P   L   R   P   R   W   C
GATGAAAGGGTGTCATCTGACCAGAGTGCGCTGTCTGAATTTATTAAGTTTGCTGAAGGT
D   E   R   V   S   S   D   Q   S   A   L   S   E   F   I   K   F   A   E   G
AGGAGGGGAGCTGCTGAAGTGCTAGTTGTGCTGAGTGAACTCCCTGATTTCCTGGCTAAA
R   R   G   A   A   E   V   L   V   V   L   S   E   L   P   D   F   L   A   K
AAAGGTGGAGAGGCAATGGATACCATCAGTGTGTTCCTCCACTCTGAGGAAGGCTCTAGG
K   G   G   E   A   M   D   T   I   S   V   F   L   H   S   E   E   G   S   R
GCTTACCGCAATGCACTATCAATGATGCCTGAGGCAATGACAATAGTCATGCTGTTTATA
A   Y   R   N   A   L   S   M   M   P   E   A   M   T   I   V   M   L   F   I
CTGGCTGGACTACTGACATCGGGAATGGTCATCTTTTTCATGTCTCCCAAAGGCATCAGT
L   A   G   L   L   T   S   G   M   V   I   F   F   M   S   P   K   G   I   S
AGAATGTCTATGGCGATGGGCACAATGGCCGGCTGTGGATATCTCATGTTCCTTGGAGGC
R   M   S   M   A   M   G   T   M   A   G   C   G   Y   L   M   F   L   G   G
GTCAAACCCACTCACATCTCCTATGTCATGCTCATATTCTTTGTCCTGATGGTGGTTGTG
V   K   P   T   H   I   S   Y   V   M   L   I   F   F   V   L   M   V   V   V
ATCCCCGAGCCAGGGCAACAAAGGTCCATCCAAGACAACCAAGTGGCATACCTCATTATT
I   P   E   P   G   Q   Q   R   S   I   Q   D   N   Q   V   A   Y   L   I   I
GGCATCCTGACGCTGGTTTCAGCGGTGGCAGCCAACGAGCTAGGCATGCTGGAGAAAACC
G   I   L   T   L   V   S   A   V   A   A   N   E   L   G   M   L   E   K   T
AAAGAGGACCTCTTTGGGAAGAAGAACTTAATTCCATCTAGTGCTTCACCCTGGAGTTGG
K   E   D   L   F   G   K   K   N   L   I   P   S   S   A   S   P   W   S   W
CCGGATCTTGACCTGAAGCCAGGAGCTGCCTGGACAGTGTACGTTGGCATTGTTACAATG
P   D   L   D   L   K   P   G   A   A   W   T   V   Y   V   G   I   V   T   M

FIGURE 1 (continued)

(SEQ ID NO:1 (cont.)) CTCTCTCCAATGTTGCACCACTGGATCAAAGTCGAATATGGCAACCTGTCTCTGTCTGGA
(SEQ ID NO:2 (cont.)) L   S   P   M   L   H   H   W   I   K   V   E   Y   G   N   L   S   L   S   G ATAGCCCAGTCAGCCTCAGTCCTTTCTTTCATGGACAAGGGGATACCATTCATGAAGATG
I   A   Q   S   A   S   V   L   S   F   M   D   K   G   I   P   F   M   K   M AATATCTCGGTCATAATGCTGCTGGTCAGTGGCTGGAATTCAATAACAGTGATGCCTCTG
N   I   S   V   I   M   L   L   V   S   G   W   N   S   I   T   V   M   P   L CTCTGTGGCATAGGGTGCGCCATGCTCCACTGGTCTCTCATTTTACCTGGAATCAAAGCG
L   C   G   I   G   C   A   M   L   H   W   S   L   I   L   P   G   I   K   A 7288[7333]                 7319 [7319]
CAGCAGTCAAAGCTA⁵GCACAGAGAAGGGTGTTCCATGGCGTTGCCA²AGAACCCTGTGGTT
Q   Q   S   K   L   A   Q   R   R   V   F   H   G   V   A   K   N   P   V   V
         2405                  2416

GATGGGAATCCAACAGTTGACATTGAGGAAGCTCCTGAAATGCCTGCCCTTTATGAGAAG
D   G   N   P   T   V   D   I   E   E   A   P   E   M   P   A   L   Y   E   K

AAACTGGCTCTATATCTCCTTCTTGCTCTCAGCCTAGCTTCTGTTGCCATGTGCAGAACG
K   L   A   L   Y   L   L   L   A   L   S   L   A   S   V   A   M   C   R   T

CCCTTTTCATTGGCTGAAGGCATTGTCCTAGCATCAGCTGCCTTAGGGCCGCTCATAGAG
P   F   S   L   A   E   G   I   V   L   A   S   A   A   L   G   P   L   I   E

GGAAACACCAGCCTTCTTTGGAATGGACCCATGGCTGTCTCCATGACAGGAGTCATGAGG
G   N   T   S   L   L   W   N   G   P   M   A   V   S   M   T   G   V   M   R

GGGAATCACTATGCTTTTGTGGGAGTCATGTACAATCTATGGAAGATGAAAACTGGACGC
G   N   H   Y   A   F   V   G   V   M   Y   N   L   W   K   M   K   T   G   R

CGGGGGAGCGCGAATGGAAAAACTTTGGGTGAAGTCTGGAAGAGGGAACTGAATCTGTTG
R   G   S   A   N   G   K   T   L   G   E   V   W   K   R   E   L   N   L   L

GACAAGCGACAGTTTGAGTTGTATAAAAGGACCGACATTGTGGAGGTGGATCGTGATACG
D   K   R   Q   F   E   L   Y   K   R   T   D   I   V   E   V   D   R   D   T

GCACGCAGGCATTTGGCCGAAGGGAAGGTGGACACCGGGGTGGCGGTCTCCAGGGGGACC
A   R   R   H   L   A   E   G   K   V   D   T   G   V   A   V   S   R   G   T

GCAAAGTTAAGGTGGTTCCATGAGCGTGGCTATGTCAAGCTGGAAGGTAGGGTGATTGAC
A   K   L   R   W   F   H   E   R   G   Y   V   K   L   E   G   R   V   I   D

CTGGGGTGTGGCCGCGGAGGCTGGTGTTACTACGCTGCTGCGCAAAAGGAAGTGAGTGGG
L   G   C   G   R   G   G   W   C   Y   Y   A   A   A   Q   K   E   V   S   G

GTCAAAGGATTTACTCTTGGAAGAGACGGCCATGAGAAACCCATGAATGTGCAAAGTCTG
V   K   G   F   T   L   G   R   D   G   H   E   K   P   M   N   V   Q   S   L

GGATGGAACATCATCACCTTCAAGGACAAAACTGATATCCACCGCCTAGAACCAGTGAAA
G   W   N   I   I   T   F   K   D   K   T   D   I   H   R   L   E   P   V   K

TGTGACACCCTTTTGTGTGACATTGGAGAGTCATCATCGTCATCGGTCACAGAGGGGAA
C   D   T   L   L   C   D   I   G   E   S   S   S   S   S   V   T   E   G   E

AGGACCGTGAGAGTTCTTGATACTGTAGAAAAATGGCTGGCTTGTGGGGTTGACAACTTC
R   T   V   R   V   L   D   T   V   E   K   W   L   A   C   G   V   D   N   F

TGTGTGAAGGTGTTAGCTCCATACATGCCAGATGTTCTTGAGAAACTGGAATTGCTCCAA
C   V   K   V   L   A   P   Y   M   P   D   V   L   E   K   L   E   L   L   Q

AGGAGGTTTGGCGGAACAGTGATCAGGAACCCTCTCTCCAGGAATTCCACTCATGAAATG
R   R   F   G   G   T   V   I   R   N   P   L   S   R   N   S   T   H   E   M

TACTACGTGTCTGGAGCCCGCAGCAATGTCACATTTACTGTGAACCAAACATCCCGCCTC
Y   Y   V   S   G   A   R   S   N   V   T   F   T   V   N   Q   T   S   R   L

CTGATGAGGAGAATGAGGCGTCCAACTGGAAAAGTGACCCTGGAGGCTGACGTCATCCTC
L   M   R   R   M   R   R   P   T   G   K   V   T   L   E   A   D   V   I   L

CCAATTGGGACACGCAGTGTTGAGACAGACAAGGGACCCCTGGACAAAGAGGCCATAGAA
P   I   G   T   R   S   V   E   T   D   K   G   P   L   D   K   E   A   I   E

FIGURE 1 (continued)

(SEQ ID NO:1 (cont.)) GAAAGGGTTGAGAGGATAAAATCTGAGTACATGACCTCTTGGTTTTATGACAATGACAAC
(SEQ ID NO:2 (cont.)) E   R   V   E   R   I   K   S   E   Y   M   T   S   W   F   Y   D   N   D   N
CCCTACAGGACCTGGCACTACTGTGGCTCGTACGTCACAAAAACCTCAGGAAGTGCGGCG
P   Y   R   T   W   H   Y   C   G   S   Y   V   T   K   T   S   G   S   A   A
AGCATGGTAAATGGTGTTATTAAAATTCTGACATATCCATGGGACAGGATAGAGGAGGTC
S   M   V   N   G   V   I   K   I   L   T   Y   P   W   D   R   I   E   E   V
ACAAGAATGGCAATGACTGACACAACCCCTTTTGGACAGCAAAGAGTGTTTAAAGAAAAA
T   R   M   A   M   T   D   T   T   P   F   G   Q   Q   R   V   F   K   E   K
GTTGACACCAGAGCAAAGGATCCACCAGCGGGAACTAGGAAGATCATGAAAGTTGTCAAC
V   D   T   R   A   K   D   P   P   A   G   T   R   K   I   M   K   V   V   N
AGGTGGCTGTTCCGCCACCTGGCCAGAGAAAAGAACCCCAGACTGTGCACAAAGGAAGAA
R   W   L   F   R   H   L   A   R   E   K   N   P   R   L   C   T   K   E   E
TTTATTGCAAAAGTCCGAAGTCATGCAGCCATTGGAGCTTACCTGGAAGAACAAGAACAG
F   I   A   K   V   R   S   H   A   A   I   G   A   Y   L   E   E   Q   E   Q
TGGAAGACTGCCAATGAGGCTGTCCAAGACCCAAAGTTCTGGGAACTGGTGGATGAAGAA
W   K   T   A   N   E   A   V   Q   D   P   K   F   W   E   L   V   D   E   E
AGGAAGCTGCACCAACAAGGCAGGTGTCGGACTTGTGTGTACAACATGATGGGGAAAAGA
R   K   L   H   Q   Q   G   R   C   R   T   C   V   Y   N   M   M   G   K   R
GAGAAGAAGCTGTCAGAGTTTGGGAAAGCAAAGGGAAGCCGTGCCATATGGTATATGTGG
E   K   K   L   S   E   F   G   K   A   K   G   S   R   A   I   W   Y   M   W
CTGGGAGCGCGGTATCTTGAGTTTGAGGCCCTGGGATTCCTGAATGAGGACCATTGGGCT
L   G   A   R   Y   L   E   F   E   A   L   G   F   L   N   E   D   H   W   A
TCCAGGGAAAACTCAGGAGGAGGAGTGGAAGGCATTGGCTTACAATACCTAGGATATGTG
S   R   E   N   S   G   G   G   V   E   G   I   G   L   Q   Y   L   G   Y   V
ATCAGAGACCTGGCTGCAATGGATGGTGGTGGATTCTACGCGGATGACACCGCTGGATGG
I   R   D   L   A   A   M   D   G   G   G   F   Y   A   D   D   T   A   G   W
GACACGCGCATCACAGAGGCAGACCTTGATGATGAACAGGAGATCTTGAACTACATGAGC
D   T   R   I   T   E   A   D   L   D   D   E   Q   E   I   L   N   Y   M   S
CCACATCACAAAAAACTGGCACAAGCAGTGATGGAAATGACATACAAGAACAAAGTGGTG
P   H   H   K   K   L   A   Q   A   V   M   E   M   T   Y   K   N   K   V   V
AAAGTGTTGAGACCAGCCCCAGGAGGGAAAGCCTACATGGATGTCATAAGTCGACGAGAC
K   V   L   R   P   A   P   G   G   K   A   Y   M   D   V   I   S   R   R   D
CAGAGAGGATCCGGGCAGGTAGTGACTTATGCTCTGAACACCATCACCAACTTGAAAGTC
Q   R   G   S   G   Q   V   V   T   Y   A   L   N   T   I   T   N   L   K   V
CAATTGATCAGAATGGCAGAAGCAGAGATGGTGATACATCACCAACATGTTCAAGATTGT
Q   L   I   R   M   A   E   A   E   M   V   I   H   H   Q   H   V   Q   D   C
GATGAATCAGTTCTGACCAGGCTGGAGGCATGGCTCACTGAGCACGGATGTGACAGACTG
D   E   S   V   L   T   R   L   E   A   W   L   T   E   H   G   C   D   R   L
AAGAGGATGGCGGTGAGTGGAGACGACTGTGTGGTCCGGCCCATCGATGACAGGTTCGGC
K   R   M   A   V   S   G   D   D   C   V   V   R   P   I   D   D   R   F   G
CTGGCCCTGTCCCATCTCAACGCCATGTCCAAGGTTAGAAAGGACATATCTGAATGGCAG
L   A   L   S   H   L   N   A   M   S   K   V   R   K   D   I   S   E   W   Q
CCATCAAAAGGGTGGAATGATTGGGAGAATGTGCCCTTCTGTTCCCACCACTTCCATGAA
P   S   K   G   W   N   D   W   E   N   V   P   F   C   S   H   H   F   H   E
CTACAGCTGAAGGATGGCAGGAGGATTGTGGTGCCTTGCCGAGAACAGGACGAGCTCATT
L   Q   L   K   D   G   R   R   I   V   V   P   C   R   E   Q   D   E   L   I
GGGAGAGGAAGGGTGTCTCCAGGAAACGGCTGGATGATCAAGGAAACAGCTTGCCTCAGC
G   R   G   R   V   S   P   G   N   G   W   M   I   K   E   T   A   C   L   S
AAAGCCTATGCCAACATGTGGTCACTGATGTATTTTCACAAAAGGGACATGAGGCTACTG
K   A   Y   A   N   M   W   S   L   M   Y   F   H   K   R   D   M   R   L   L

FIGURE 1 (continued)

(SEQ ID NO:1 (cont.)) TCATTGGCTGTTTCCTCAGCTGTTCCCACCTCATGGGTTCCACAAGGACGCACAACATGG
(SEQ ID NO:2 (cont.)) S  L  A  V  S  S  A  V  P  T  S  W  V  P  Q  G  R  T  T  W
TCGATTCATGGGAAAGGGGAGTGGATGACCACGGAAGACATGCTTGAGGTGTGGAACAGA
S  I  H  G  K  G  E  W  M  T  T  E  D  M  L  E  V  W  N  R
GTATGGATAACCAACAACCCACACATGCAGGACAAGACAATGGTGAAAAAATGGAGAGAT
V  W  I  T  N  N  P  H  M  Q  D  K  T  M  V  K  K  W  R  D
GTCCCTTATCTAACCAAGAGACAAGACAAGCTGTGCGGATCACTGATTGGAATGACCAAT
V  P  Y  L  T  K  R  Q  D  K  L  C  G  S  L  I  G  M  T  N
AGGGCCACCTGGGCCTCCCACATCCATTTAGTCATCCATCGTATCCGAACGCTGATTGGA
R  A  T  W  A  S  H  I  H  L  V  I  H  R  I  R  T  L  I  G
CAGGAGAAATACACTGACTACCTAACAGTCATGGACAGGTATTCTGTGGATGCTGACCTG
Q  E  K  Y  T  D  Y  L  T  V  M  D  R  Y  S  V  D  A  D  L
CAACTGGGTGAGCTTATCTGAAACACCATCTAACAGGAATAACCGGGATACAAACCACGG
Q  L  G  E  L  I  *
GTGGAGAACCGGACTCCCCACAACCTGAAACCGGGATATAAACCACGGCTGGAGAACCGG
10545[10590]
A9CTCCGCACTTAAAATGAAACAGAAACCGGGATAAAAACTACGGATGGAGAACCGGACTC
CACACATTGAGACAGAAGAAGTTGTCAGCCCAGAACCCCACACGAGTTTTGCCACTGCTA
AGCTGTGAGGCAGTGCAGGCTGGGACAGCCGACCTCCAGGTTGCGAAAAACCTGGTTTCT
GGGACCTCCCACCCCAGAGTAAAAAGAACGGAGCCTCCGCTACCACCCTCCCACGTGGTG
GTAGAAAGACGGGGTCTAGAGGTTAGAGGAGACCCTCCAGGGAACAAATAGTGGGACCAT
ATTGACGCCAGGGAAAGACCGGAGTGGTTCTCTGCTTTTCCTCCAGAGGTCTGTGAGCAC
AGTTTGCTCAAGAATAAGCAGACCTTTGGATGACAAACACAAAACCACT -Numbering on highlighted letters correspond to nucleotides
changes reported in Figure 5. Numbers in brackets refer to the
numbering in SEQ ID NO:1
-Lower cases correspond to ZIKV-Yap 2007 prME with the
bold/underlined sequence representing the ZIKV anchor domain.
-Upper cases correspond to YFV 17D sequences.
-n= G or A (A being the dominant peak) resulting in Thr (or
Ala)

| Polyprotein | C protein (carboxy-terminus) | C anchor domain | prM protein (amino-terminus) | |
|---|---|---|---|---|
| YFV-17D | ...LSSRKRR-(2b/3)- | SHDVLTVQFLIIGMLIMTGG-(sign)- | VTL**...functional | [SEQ ID NO:10] |
| JEV SA14-14-2 | ...GRKQNKR-(2b/3)- | GGNEGSIMWLASLAVVIACAGA-(sign)- | MKL..functional | [SEQ ID NO:11] |
| ZIKV-Yap2008 | ...RKEKKRR-(2b/3)- | GTDTSVGIVGLLLTTAMA-(sign)- | VEV...functional | [SEQ ID NO:12] |
| Chimerivax-JE | ...LSSRKRR-(2b/3)- | SHDVLTVQFLIIGMLIMTGG-(sign)- | MKL** functional | [SEQ ID NO:13] |
| Chimeric YF/ZIKV_YF-Canch... | ...LSSRKRR-(2b/3)- | SHDVLTVQFLIIGMLIMTGG-(sign)- | VEV**..non-functional | [SEQ ID NO:14] |
| Chimeric YF/ZIKV_ZIK-Canch | ...LSSRKRR-(2b/3)- | GTDTSVGIVGLLLTTAMA-(sign)- | VEV...functional | [SEQ ID NO:15] |

Figure 4

A. synthetic (chimeric) cDNA ⇨ IVT + TFXN ⇨ serial passage of infectious virus from supernatants ⇨ harvest of adapted progeny

B. synthetic (chimeric) cDNA ⇨ IVT + TFXN ⇨ serial passage of infectious virus from supernatants in mouse brain ⇨ harvest of adapted progeny

C. synthetic (chimeric) cDNA ⇨ direct plasmid DNA TFXN ⇨ serial passage of plasmid transfected cells bearing replicating virus ⇨ serial passage of infectious virus from supernatants ⇨ harvest of adapted progeny

Figure 8

Virus titer upon passaging A

|  | 4G2 | JEV Env mAb | YFV NS1 mAb |
|---|---|---|---|
| YFV-17D | | | |
| ZIKV BeH819015 | | | |
| YF-ZIKprME | | | |

Figure 12

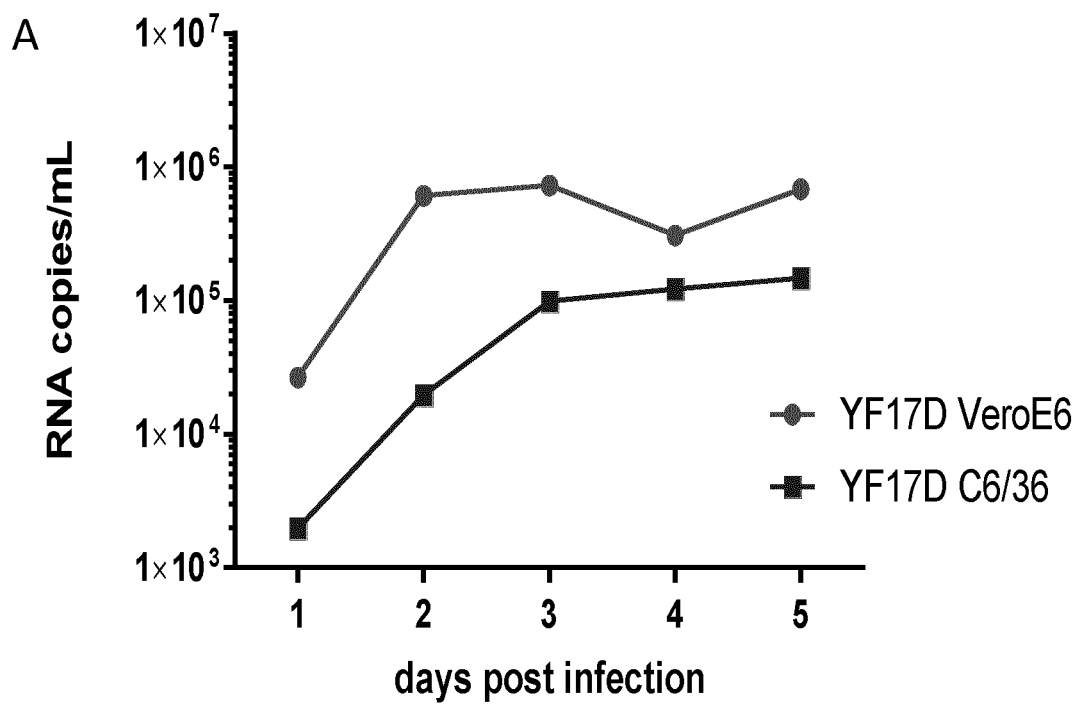
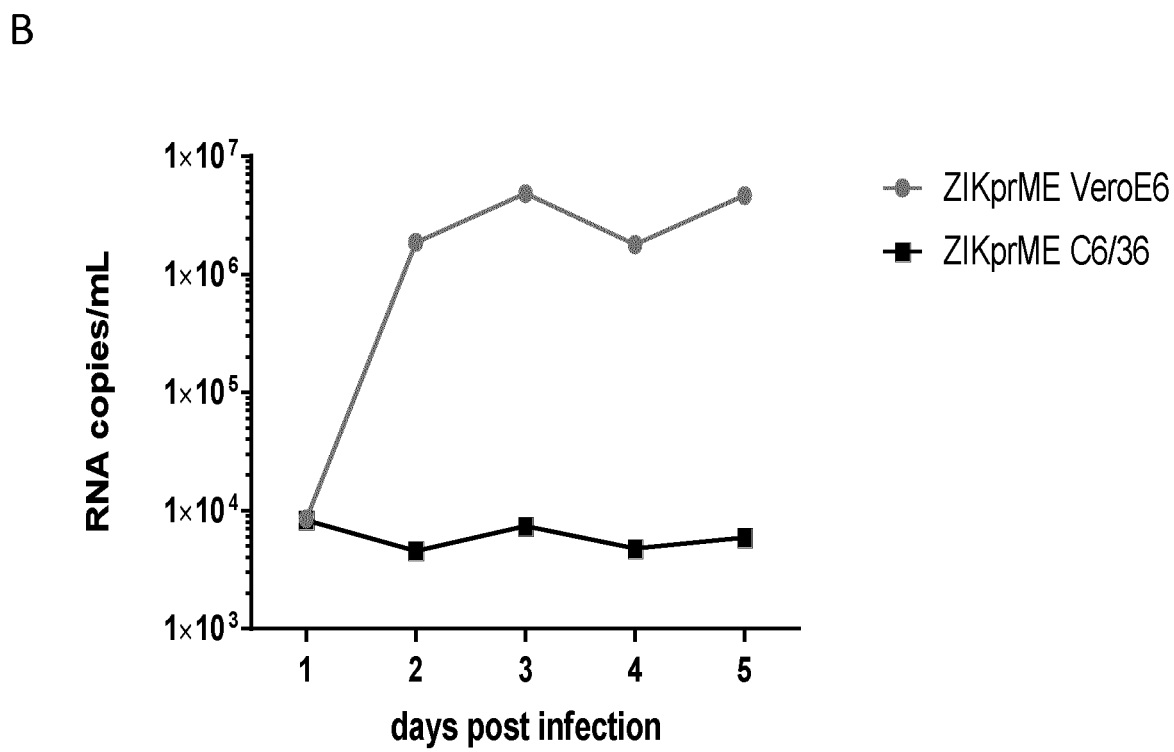
Figure 13

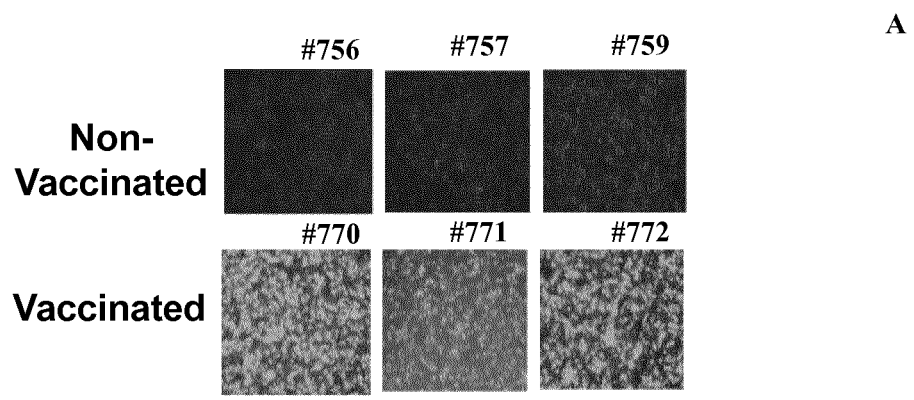
A
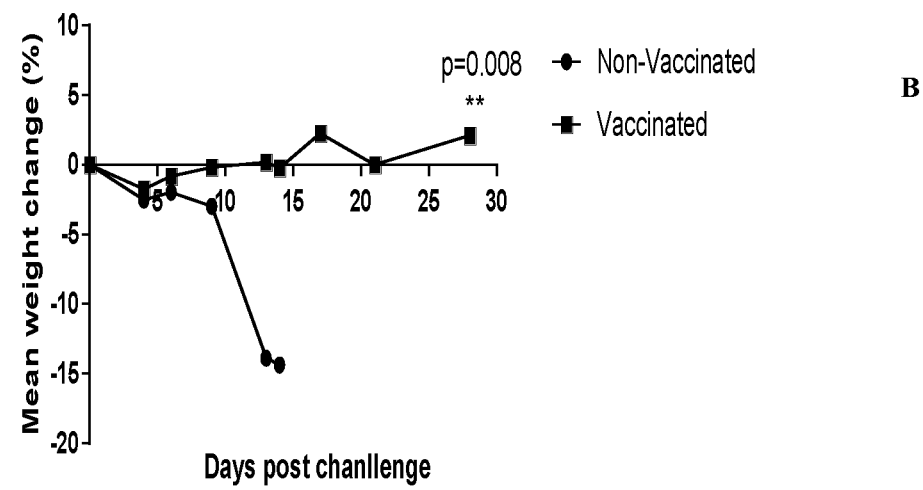
B
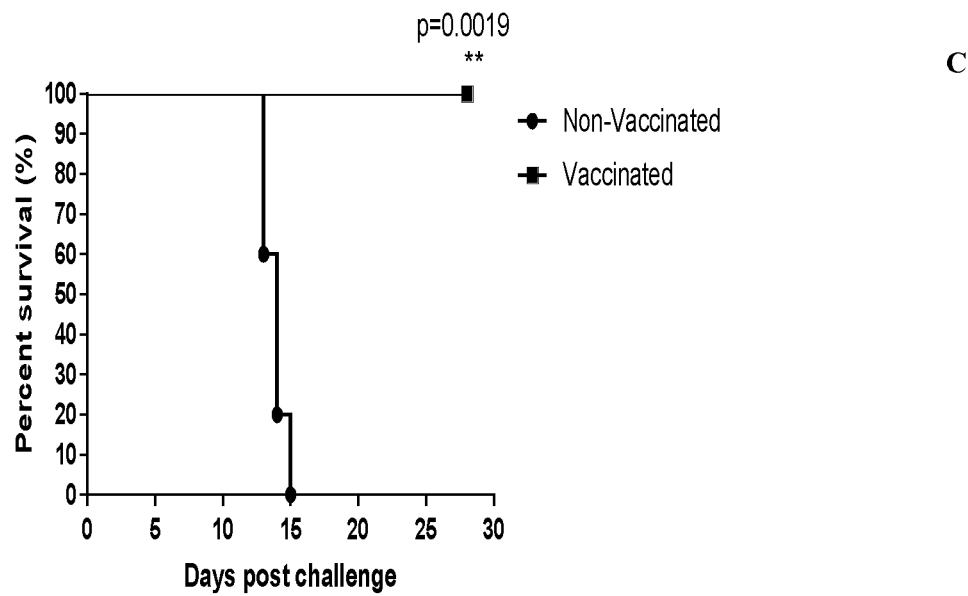
C
Figure 14

Figure 16

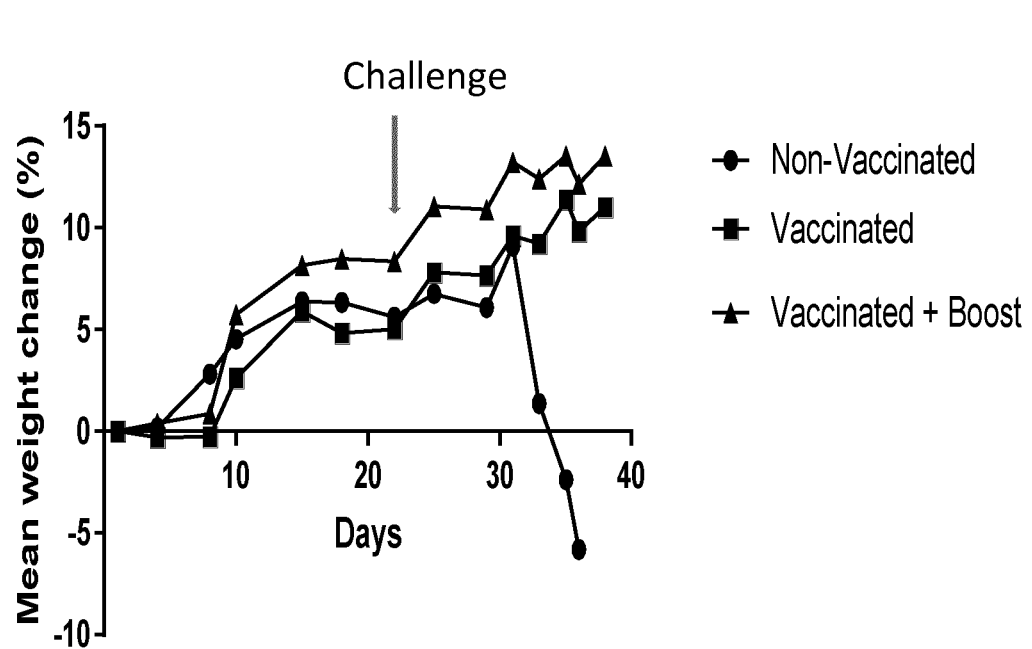
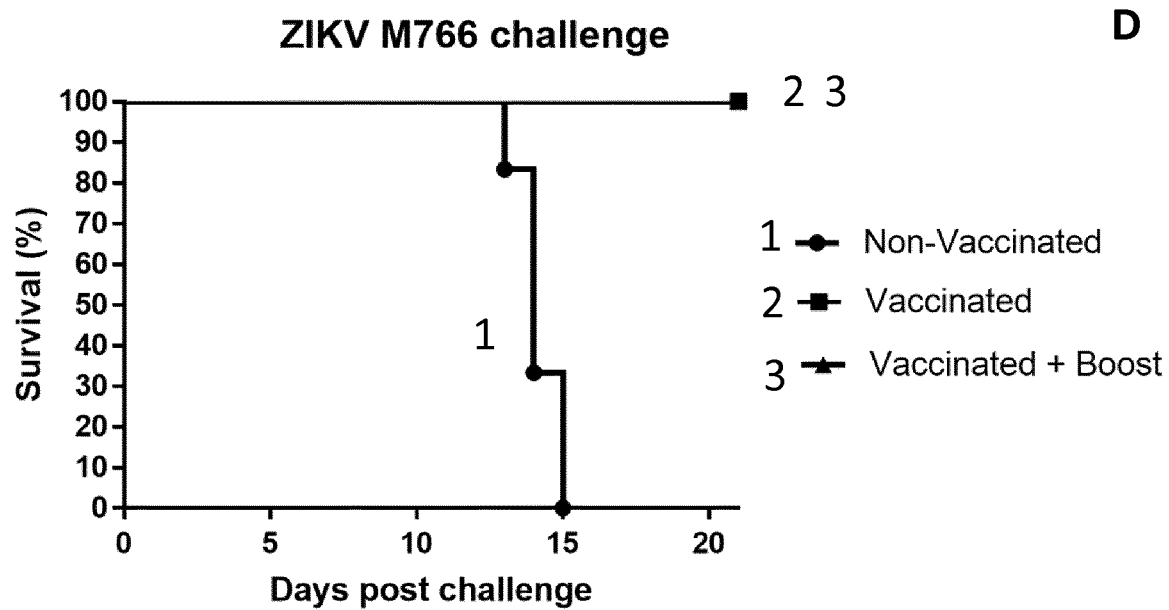
Figure 16 (continued)

SEQUENCE LISTING

```
<160> NUMBER OF SEQ ID NOS: 15

<210> SEQ ID NO 1
<211> LENGTH: 10907
<212> TYPE: DNA
<213> ORGANISM: Artificial Sequence
<220> FEATURE:
<223> OTHER INFORMATION: Yellow Fever Zika chimer
<220> FEATURE:
<221> NAME/KEY: CDS
<222> LOCATION: (119)..(10399)
<220> FEATURE:
<221> NAME/KEY: misc_feature
<222> LOCATION: (1097)..(1097)
<223> OTHER INFORMATION: r = a or g (leading to Thr or Ala at amino acid
      327)

<400> SEQUENCE: 1
agtaaatcct gtgtgctaat tgaggtgcat tggtctgcaa atcgagttgc taggcaataa        60
acacatttgg attaatttta atcgttcgtt gagcgattag cagagaactg accagaac        118
```

| | | |
|---|---|---|
| atg tct ggt cgt aaa gct cag gga aaa acc ctg ggc gtc aat atg gta<br>Met Ser Gly Arg Lys Ala Gln Gly Lys Thr Leu Gly Val Asn Met Val<br>1                         5                         10                  15 | 166 |

| cga cga gga gtt cgc tcc ttg tca aac aaa ata aaa caa aaa aca aaa<br>Arg Arg Gly Val Arg Ser Leu Ser Asn Lys Ile Lys Gln Lys Thr Lys<br>          20                    25                    30 | 214 |

| caa att gga aac aga cct gga cct tca aga ggt gtt caa gga ttt atc<br>Gln Ile Gly Asn Arg Pro Gly Pro Ser Arg Gly Val Gln Gly Phe Ile<br>              35                  40                    45 | 262 |

| ttt ttc ttt ttg ttc aac att ttg act gga aaa aag atc aca gcc cac<br>Phe Phe Phe Leu Phe Asn Ile Leu Thr Gly Lys Lys Ile Thr Ala His<br>    50                    55                    60 | 310 |

| cta aag agg ttg tgg aaa atg ctg gac cca aga caa ggc ttg gct gtt<br>Leu Lys Arg Leu Trp Lys Met Leu Asp Pro Arg Gln Gly Leu Ala Val<br>65                        70                    75                  80 | 358 |

| cta agg aaa gtc aag aga gtg gtg gcc agt ttg atg aga gga ttg tcc<br>Leu Arg Lys Val Lys Arg Val Val Ala Ser Leu Met Arg Gly Leu Ser<br>                    85                    90                    95 | 406 |

| tcg agg aaa cgc cgt ggc aca gat act agt gtc gga att gtt ggc ctc<br>Ser Arg Lys Arg Arg Gly Thr Asp Thr Ser Val Gly Ile Val Gly Leu<br>          100                    105                    110 | 454 |

| ctg ctg acc aca gcc atg gca gtg gag gtc act aga cgt ggg agt gca<br>Leu Leu Thr Thr Ala Met Ala Val Glu Val Thr Arg Arg Gly Ser Ala<br>              115                    120                    125 | 502 |

| tac tat atg tac ttg gac aga agc gat gct ggg gag gcc ata tct ttt<br>Tyr Tyr Met Tyr Leu Asp Arg Ser Asp Ala Gly Glu Ala Ile Ser Phe<br>130                        135                    140 | 550 |

| cca acc aca ctg ggg atg aac aag tgt tac ata cag atc atg gat ctt<br>Pro Thr Thr Leu Gly Met Asn Lys Cys Tyr Ile Gln Ile Met Asp Leu<br>145                        150                    155                  160 | 598 |

| gga cac atg tgt gat gcc acc atg agc tat gaa tgc cct atg ttg gat<br>Gly His Met Cys Asp Ala Thr Met Ser Tyr Glu Cys Pro Met Leu Asp<br>                    165                    170                    175 | 646 |

| gag ggg gta gaa cca gat gac gtc gat tgt tgg tgc aac acg aca tca<br>Glu Gly Val Glu Pro Asp Asp Val Asp Cys Trp Cys Asn Thr Thr Ser<br>180                        185                    190 | 694 |

| act tgg gtt gtg tac gga acc tgc cac cac aaa aaa ggt gaa gca cgg<br>Thr Trp Val Val Tyr Gly Thr Cys His His Lys Lys Gly Glu Ala Arg<br>          195                    200                    205 | 742 |

| aga tct aga aga gct gtg acg ctc ccc tcc cat tcc act agg aag ctg<br>Arg Ser Arg Arg Ala Val Thr Leu Pro Ser His Ser Thr Arg Lys Leu<br>          210                    215                    220 | 790 |

| caa acg cgg tcg cag acc tgg ttg gaa tca aga gaa tat aca aag cac<br>Gln Thr Arg Ser Gln Thr Trp Leu Glu Ser Arg Glu Tyr Thr Lys His<br>225                        230                    235                  240 | 838 |

| ctg att aga gtc gaa aat tgg ata ttc agg aac cct ggc ttc gcg tta<br>Leu Ile Arg Val Glu Asn Trp Ile Phe Arg Asn Pro Gly Phe Ala Leu<br>                    245                    250                    255 | 886 |

| gca gca gct gcc atc gcc tgg ctt ttg gga agt tca acg agc caa aaa<br>Ala Ala Ala Ala Ile Ala Trp Leu Leu Gly Ser Ser Thr Ser Gln Lys<br>                260                    265                    270 | 934 |

| gtc ata tac ttg gtc atg ata ctg ctg att gcc ccg gca tac agc atc<br>Val Ile Tyr Leu Val Met Ile Leu Leu Ile Ala Pro Ala Tyr Ser Ile<br>275                        280                    285 | 982 |

| agg tgc ata gga gtc agc aat agg gac ttt gtg gaa ggt atg tca ggt<br>Arg Cys Ile Gly Val Ser Asn Arg Asp Phe Val Glu Gly Met Ser Gly<br>          290                    295                    300 | 1030 |

| ggg act tgg gtt gat gtt gtc ttg gaa cat gga ggt tgt gtt acc gta<br>Gly Thr Trp Val Asp Val Val Leu Glu His Gly Gly Cys Val Thr Val | 1078 |

```
                    305                 310                 315                 320
      atg gca cag gac aaa ccg rct gtc gac ata gag ctg gtt aca aca aca          1126
      Met Ala Gln Asp Lys Pro Xaa Val Asp Ile Glu Leu Val Thr Thr Thr
                              325                 330                 335 gtc agc aac atg gcg gag gta aga tcc tat tgc tat gag gca tca ata          1174
      Val Ser Asn Met Ala Glu Val Arg Ser Tyr Cys Tyr Glu Ala Ser Ile
                      340                 345                 350 tcg gac atg gct tcg gac agc cgc tgc cca aca caa ggt gaa gcc tac          1222
      Ser Asp Met Ala Ser Asp Ser Arg Cys Pro Thr Gln Gly Glu Ala Tyr
                  355                 360                 365 ctt gac aag cag tca gac act caa tat gtc tgc aaa aga acg tta gtg          1270
      Leu Asp Lys Gln Ser Asp Thr Gln Tyr Val Cys Lys Arg Thr Leu Val
              370                 375                 380 gac aga ggc tgg gga aat gga tgt gga ctt ttt ggc aaa ggg agc ctg          1318
      Asp Arg Gly Trp Gly Asn Gly Cys Gly Leu Phe Gly Lys Gly Ser Leu
      385                 390                 395                 400 gtg aca tgc gct aag ttt gca tgc tcc aag aaa atg acc ggg aag agc          1366
      Val Thr Cys Ala Lys Phe Ala Cys Ser Lys Lys Met Thr Gly Lys Ser
                          405                 410                 415 atc cag cca gag aat ctg gag tac cgg ata atg ctg tca gtt cat ggc          1414
      Ile Gln Pro Glu Asn Leu Glu Tyr Arg Ile Met Leu Ser Val His Gly
                      420                 425                 430 tcc cag cac agt ggg atg atc gtt aat gac aca gga cat gaa act gat          1462
      Ser Gln His Ser Gly Met Ile Val Asn Asp Thr Gly His Glu Thr Asp
                  435                 440                 445 gag aat aga gcg aag gtt gag ata acg ccc aat tca cca aga gct gaa          1510
      Glu Asn Arg Ala Lys Val Glu Ile Thr Pro Asn Ser Pro Arg Ala Glu
              450                 455                 460 gcc acc ctg ggg ggt ttt gga agc cta gga ctt gat tgt gaa ccg agg          1558
      Ala Thr Leu Gly Gly Phe Gly Ser Leu Gly Leu Asp Cys Glu Pro Arg
      465                 470                 475                 480 aca ggc ctt gac ttt tca gat ttg tat tac ttg act atg aat aac aag          1606
      Thr Gly Leu Asp Phe Ser Asp Leu Tyr Tyr Leu Thr Met Asn Asn Lys
                          485                 490                 495 cac tgg ttg gtt cac aag gag tgg ttc cac gac att cca tta cct tgg          1654
      His Trp Leu Val His Lys Glu Trp Phe His Asp Ile Pro Leu Pro Trp
                      500                 505                 510 cat gct ggg gca gac acc gga act cca cat tgg aac aac aaa gaa gca          1702
      His Ala Gly Ala Asp Thr Gly Thr Pro His Trp Asn Asn Lys Glu Ala
                  515                 520                 525 ttg gta gag ttc aag gac gca cat gcc aaa agg caa act gtc gtg gtt          1750
      Leu Val Glu Phe Lys Asp Ala His Ala Lys Arg Gln Thr Val Val Val
              530                 535                 540 cta ggg agt caa gaa gga gca gtt cac acg gcc ctt gct gga gct ctg          1798
      Leu Gly Ser Gln Glu Gly Ala Val His Thr Ala Leu Ala Gly Ala Leu
      545                 550                 555                 560 gag gct gag atg gat ggt gca aag gga agg ctg tcc tct ggc cac ttg          1846
      Glu Ala Glu Met Asp Gly Ala Lys Gly Arg Leu Ser Ser Gly His Leu
                          565                 570                 575 aaa tgt cgc ctg aaa atg gat aaa ctt aga ttg aag ggc gtg tca tac          1894
      Lys Cys Arg Leu Lys Met Asp Lys Leu Arg Leu Lys Gly Val Ser Tyr
                      580                 585                 590 tcc ttg tgt acc gca gcg ttc aca ttc acc aag atc ccg gct gaa aca          1942
      Ser Leu Cys Thr Ala Ala Phe Thr Phe Thr Lys Ile Pro Ala Glu Thr
                  595                 600                 605 ctg cac ggg aca gtc aca gtg gag gta cag tac gca ggg aca gat gga          1990
      Leu His Gly Thr Val Thr Val Glu Val Gln Tyr Ala Gly Thr Asp Gly
              610                 615                 620 ccc tgc aag gtt cca gct cag atg gcg gtg gac atg caa act ctg acc          2038
```

```
              Pro Cys Lys Val Pro Ala Gln Met Ala Val Asp Met Gln Thr Leu Thr
              625                 630                 635                 640 cca gtt ggg agg ctg ata acc gct aac cct gta atc act gaa agc act              2086
Pro Val Gly Arg Leu Ile Thr Ala Asn Pro Val Ile Thr Glu Ser Thr
                645                 650                 655 gag aac tct aag atg atg ctg gaa ctt gat cca cca ttt ggg gac tct              2134
Glu Asn Ser Lys Met Met Leu Glu Leu Asp Pro Pro Phe Gly Asp Ser
                660                 665                 670 tac att gtc ata gga gtc ggg gag aag aag atc acc cat cac tgg cac              2182
Tyr Ile Val Ile Gly Val Gly Glu Lys Lys Ile Thr His His Trp His
                675                 680                 685 agg agt ggc agc acc att gga aaa gca ttt gaa gcc act gtg aga ggt              2230
Arg Ser Gly Ser Thr Ile Gly Lys Ala Phe Glu Ala Thr Val Arg Gly
            690                 695                 700 gcc aag aga atg gca gtc ttg gga gac aca gcc tgg gat ttt gga tca              2278
Ala Lys Arg Met Ala Val Leu Gly Asp Thr Ala Trp Asp Phe Gly Ser
705                 710                 715                 720 gtt gga ggt gct ctc aac tca ttg ggc aag ggc atc cat caa att ttt              2326
Val Gly Gly Ala Leu Asn Ser Leu Gly Lys Gly Ile His Gln Ile Phe
                725                 730                 735 gga gca gct ttc aaa tta ttg ttt gga gga atg tcc tgg ttc tca caa              2374
Gly Ala Ala Phe Lys Leu Leu Phe Gly Gly Met Ser Trp Phe Ser Gln
                740                 745                 750 att ctc att gga acg ttg ctg gtg tgg ttg ggt ctg aat aca aag aat              2422
Ile Leu Ile Gly Thr Leu Leu Val Trp Leu Gly Leu Asn Thr Lys Asn
                755                 760                 765 gga tct att tcc ctt acg tgc ttg gcc tta ggg gga gtg ttg atc ttt              2470
Gly Ser Ile Ser Leu Thr Cys Leu Ala Leu Gly Gly Val Leu Ile Phe
                770                 775                 780 tta tcc aca gcc gtc tct gcg ggc gcc gat caa gga tgc gcc atc aac              2518
Leu Ser Thr Ala Val Ser Ala Gly Ala Asp Gln Gly Cys Ala Ile Asn
785                 790                 795                 800 ttt ggc aag aga gag ctc aag tgc gga gat ggt atc ttc ata ttt aga              2566
Phe Gly Lys Arg Glu Leu Lys Cys Gly Asp Gly Ile Phe Ile Phe Arg
                805                 810                 815 gac tct gat gac tgg ctg aac aag tac tca tac tat cca gaa gat cct              2614
Asp Ser Asp Asp Trp Leu Asn Lys Tyr Ser Tyr Tyr Pro Glu Asp Pro
                820                 825                 830 gtg aag ctt gca tca ata gtg aaa gcc tct ttt gaa gaa ggg aag tgt              2662
Val Lys Leu Ala Ser Ile Val Lys Ala Ser Phe Glu Glu Gly Lys Cys
                835                 840                 845 ggc cta aat tca gtt gac tcc ctt gag cat gag atg tgg aga agc agg              2710
Gly Leu Asn Ser Val Asp Ser Leu Glu His Glu Met Trp Arg Ser Arg
850                 855                 860 gca gat gag atc aat gcc att ttt gag gaa aac gag gtg gac att tct              2758
Ala Asp Glu Ile Asn Ala Ile Phe Glu Glu Asn Glu Val Asp Ile Ser
865                 870                 875                 880 gtt gtc gtg cag gat cca aag aat gtt tac cag aga gga act cat cca              2806
Val Val Val Gln Asp Pro Lys Asn Val Tyr Gln Arg Gly Thr His Pro
                885                 890                 895 ttt tcc aga att cgg gat ggt ctg cag tat ggt tgg aag act tgg ggt              2854
Phe Ser Arg Ile Arg Asp Gly Leu Gln Tyr Gly Trp Lys Thr Trp Gly
                900                 905                 910 aag aac ctt gtg ttc tcc cca ggg agg aag aat gga agc ttc atc ata              2902
Lys Asn Leu Val Phe Ser Pro Gly Arg Lys Asn Gly Ser Phe Ile Ile
                915                 920                 925 gat gga aag tcc agg aaa gaa tgc ccg ttt tca aac cgg gtc tgg aat              2950
Asp Gly Lys Ser Arg Lys Glu Cys Pro Phe Ser Asn Arg Val Trp Asn
930                 935                 940
```

```
tct ttc cag ata gag gag ttt ggg acg gga gtg ttc acc aca cgc gtg    2998
Ser Phe Gln Ile Glu Glu Phe Gly Thr Gly Val Phe Thr Thr Arg Val
945                 950                 955                 960 tac atg gac gca gtc ttt gaa tac acc ata gac tgc gat gga tct atc    3046
Tyr Met Asp Ala Val Phe Glu Tyr Thr Ile Asp Cys Asp Gly Ser Ile
                965                 970                 975 ttg ggt gca gcg gtg aac gga aaa aag agt gcc cat ggc tct cca aca    3094
Leu Gly Ala Ala Val Asn Gly Lys Lys Ser Ala His Gly Ser Pro Thr
        980                 985                 990 ttt tgg atg gga agt cat gaa gta aat ggg aca tgg atg atc cac acc    3142
Phe Trp Met Gly Ser His Glu Val Asn Gly Thr Trp Met Ile His Thr
            995                 1000                1005 ttg gag gca tta gat tac aag gag tgt gag tgg cca ctg aca cat        3187
Leu Glu Ala Leu Asp Tyr Lys Glu Cys Glu Trp Pro Leu Thr His
    1010            1015                1020 acg att gga aca tca gtt gaa gag agt gaa atg ttc atg ccg aga        3232
Thr Ile Gly Thr Ser Val Glu Glu Ser Glu Met Phe Met Pro Arg
    1025            1030                1035 tca atc gga ggc cca gtt agc tct cac aat cat atc cct gga tac        3277
Ser Ile Gly Gly Pro Val Ser Ser His Asn His Ile Pro Gly Tyr
    1040            1045                1050 aag gtt cag acg aac gga cct tgg atg cag gta cca cta gaa gtg        3322
Lys Val Gln Thr Asn Gly Pro Trp Met Gln Val Pro Leu Glu Val
    1055            1060                1065 aag aga gaa gct tgc cca ggg act agc gtg atc att gat ggc aac        3367
Lys Arg Glu Ala Cys Pro Gly Thr Ser Val Ile Ile Asp Gly Asn
    1070            1075                1080 tgt gat gga cgg gga aaa tca acc aga tcc acc acg gat agc ggg        3412
Cys Asp Gly Arg Gly Lys Ser Thr Arg Ser Thr Thr Asp Ser Gly
    1085            1090                1095 aaa gtt att cct gaa tgg tgt tgc cgc tcc tgc aca atg ccg cct        3457
Lys Val Ile Pro Glu Trp Cys Cys Arg Ser Cys Thr Met Pro Pro
    1100            1105                1110 gtg agc ttc cat ggt agt gat ggg tgt tgg tat ccc atg gaa att        3502
Val Ser Phe His Gly Ser Asp Gly Cys Trp Tyr Pro Met Glu Ile
    1115            1120                1125 agg cca agg aaa acg cat gaa agc cat ctg gtg cgc tcc tgg gtt        3547
Arg Pro Arg Lys Thr His Glu Ser His Leu Val Arg Ser Trp Val
    1130            1135                1140 aca gct gga gaa ata cat gct gtc cct ttt ggt ttg gtg agc atg        3592
Thr Ala Gly Glu Ile His Ala Val Pro Phe Gly Leu Val Ser Met
    1145            1150                1155 atg ata gca atg gaa gtg gtc cta agg aaa aga cag gga cca aag        3637
Met Ile Ala Met Glu Val Val Leu Arg Lys Arg Gln Gly Pro Lys
    1160            1165                1170 caa atg ttg gtt gga gga gta gtg ctc ttg gga gca atg ctg gtc        3682
Gln Met Leu Val Gly Gly Val Val Leu Leu Gly Ala Met Leu Val
    1175            1180                1185 ggg caa gta act ctc ctt gat ttg ctg aaa ctc aca gtg gct gtg        3727
Gly Gln Val Thr Leu Leu Asp Leu Leu Lys Leu Thr Val Ala Val
    1190            1195                1200 gga ttg cat ttc cat gag atg aac aat gga gga gac gcc atg tat        3772
Gly Leu His Phe His Glu Met Asn Asn Gly Gly Asp Ala Met Tyr
    1205            1210                1215 atg gcg ttg att gct gcc ttt tca atc aga cca ggg ctg ctc atc        3817
Met Ala Leu Ile Ala Ala Phe Ser Ile Arg Pro Gly Leu Leu Ile
    1220            1225                1230 ggc ttt ggg ctc agg acc cta tgg agc cct cgg gaa cgc ctt gtg        3862
Gly Phe Gly Leu Arg Thr Leu Trp Ser Pro Arg Glu Arg Leu Val
    1235            1240                1245
```

```
                                                              -continued ctg acc cta gga gca gcc atg gtg gag att gcc ttg ggt ggc gtg    3907
Leu Thr Leu Gly Ala Ala Met Val Glu Ile Ala Leu Gly Gly Val
    1250            1255                1260 atg ggc ggc ctg tgg aag tat cta aat gca gtt tct ctc tgc atc    3952
Met Gly Gly Leu Trp Lys Tyr Leu Asn Ala Val Ser Leu Cys Ile
1265                1270                1275 ctg aca ata aat gct gtt gct tct agg aaa gca tca aat acc atc    3997
Leu Thr Ile Asn Ala Val Ala Ser Arg Lys Ala Ser Asn Thr Ile
    1280            1285                1290 ttg ccc ctc atg gct ctg ttg aca ccg gtc acc atg gct gag gtg    4042
Leu Pro Leu Met Ala Leu Leu Thr Pro Val Thr Met Ala Glu Val
1295                1300                1305 aga ctt gcc gca atg ttc ttt tgt gcc atg gtt atc ata ggg gtc    4087
Arg Leu Ala Ala Met Phe Phe Cys Ala Met Val Ile Ile Gly Val
    1310            1315                1320 ctt cac cag aat ttc aag gac acc tcc atg cag aag act ata cct    4132
Leu His Gln Asn Phe Lys Asp Thr Ser Met Gln Lys Thr Ile Pro
1325                1330                1335 ctg gtg gcc ctc aca ctc aca tct tac ctg ggc ttg aca caa cct    4177
Leu Val Ala Leu Thr Leu Thr Ser Tyr Leu Gly Leu Thr Gln Pro
    1340            1345                1350 ttt ttg ggc ctg tgt gca ttt ctg gca acc cgc ata ttt ggg cga    4222
Phe Leu Gly Leu Cys Ala Phe Leu Ala Thr Arg Ile Phe Gly Arg
1355                1360                1365 agg agt atc cca gtg aat gag gca ctc gca gca gct ggt cta gtg    4267
Arg Ser Ile Pro Val Asn Glu Ala Leu Ala Ala Ala Gly Leu Val
    1370            1375                1380 gga gtg ctg gca gga ctg gct ttt cag gag atg gag aac ttc ctt    4312
Gly Val Leu Ala Gly Leu Ala Phe Gln Glu Met Glu Asn Phe Leu
1385                1390                1395 ggt ccg att gca gtt gga gga ctc ctg atg atg ctg gtt agc gtg    4357
Gly Pro Ile Ala Val Gly Gly Leu Leu Met Met Leu Val Ser Val
    1400            1405                1410 gct ggg agg gtg gat ggg cta gag ctc aag aag ctt ggt gaa gtt    4402
Ala Gly Arg Val Asp Gly Leu Glu Leu Lys Lys Leu Gly Glu Val
1415                1420                1425 tca tgg gaa gag gag gcg gag atc agc ggg agt tcc gcc cgc tat    4447
Ser Trp Glu Glu Glu Ala Glu Ile Ser Gly Ser Ser Ala Arg Tyr
    1430            1435                1440 gat gtg gca ctc agt gaa caa ggg gag ttc aag ctg ctt tct gaa    4492
Asp Val Ala Leu Ser Glu Gln Gly Glu Phe Lys Leu Leu Ser Glu
1445                1450                1455 gag aaa gtg cca tgg gac cag gtt gtg atg acc tcg ctg gcc ttg    4537
Glu Lys Val Pro Trp Asp Gln Val Val Met Thr Ser Leu Ala Leu
    1460            1465                1470 gtt ggg gct gcc ctc cat cca ttt gct ctt ctg ctg gtc ctt gct    4582
Val Gly Ala Ala Leu His Pro Phe Ala Leu Leu Leu Val Leu Ala
1475                1480                1485 ggg tgg ctg ttt cat gtc agg gga gct agg aga agt ggg gat gtc    4627
Gly Trp Leu Phe His Val Arg Gly Ala Arg Arg Ser Gly Asp Val
    1490            1495                1500 ttg tgg gat att ccc act cct aag atc atc gag gaa tgt gaa cat    4672
Leu Trp Asp Ile Pro Thr Pro Lys Ile Ile Glu Glu Cys Glu His
1505                1510                1515 ctg gag gat ggg att tat ggc ata ttc cag tca acc ttc ttg ggg    4717
Leu Glu Asp Gly Ile Tyr Gly Ile Phe Gln Ser Thr Phe Leu Gly
    1520            1525                1530 gcc tcc cag cga gga gtg gga gtg gca cag gga ggg gtg ttc cac    4762
Ala Ser Gln Arg Gly Val Gly Val Ala Gln Gly Gly Val Phe His
```

-continued

|  |  |  |  |  |  |  |  |  |  |  |  |  |
|---|---|---|---|---|---|---|---|---|---|---|---|---|
|  |  | 1535 |  |  | 1540 |  |  |  | 1545 |  |  |  |
| aca | atg | tgg | cat | gtc | aca | aga | gga | gct | ttc | ctt | gtc | agg | aat | ggc | 4807 |
| Thr | Met | Trp | His | Val | Thr | Arg | Gly | Ala | Phe | Leu | Val | Arg | Asn | Gly |  |
|  | 1550 |  |  |  | 1555 |  |  |  | 1560 |  |  |  |
| aag | aag | ttg | att | cca | tct | tgg | gct | tca | gta | aag | gaa | gac | ctt | gtc | 4852 |
| Lys | Lys | Leu | Ile | Pro | Ser | Trp | Ala | Ser | Val | Lys | Glu | Asp | Leu | Val |  |
| 1565 |  |  |  | 1570 |  |  |  | 1575 |  |  |  |
| gcc | tat | ggt | ggc | tca | tgg | aag | ttg | gaa | ggc | aga | tgg | gat | gga | gag | 4897 |
| Ala | Tyr | Gly | Gly | Ser | Trp | Lys | Leu | Glu | Gly | Arg | Trp | Asp | Gly | Glu |  |
|  | 1580 |  |  |  | 1585 |  |  |  | 1590 |  |  |  |
| gaa | gag | gtc | cag | ttg | atc | gcg | gct | gtt | cca | gga | aag | aac | gtg | gtc | 4942 |
| Glu | Glu | Val | Gln | Leu | Ile | Ala | Ala | Val | Pro | Gly | Lys | Asn | Val | Val |  |
| 1595 |  |  |  | 1600 |  |  |  | 1605 |  |  |  |
| aac | gtc | cag | aca | aaa | ccg | agc | ttg | ttc | aaa | gtg | agg | aat | ggg | gga | 4987 |
| Asn | Val | Gln | Thr | Lys | Pro | Ser | Leu | Phe | Lys | Val | Arg | Asn | Gly | Gly |  |
|  | 1610 |  |  |  | 1615 |  |  |  | 1620 |  |  |  |
| gaa | atc | ggg | gct | gtc | gct | ctt | gac | tat | ccg | agt | ggc | act | tca | gga | 5032 |
| Glu | Ile | Gly | Ala | Val | Ala | Leu | Asp | Tyr | Pro | Ser | Gly | Thr | Ser | Gly |  |
| 1625 |  |  |  | 1630 |  |  |  | 1635 |  |  |  |
| tct | cct | att | gtt | aac | agg | aac | gga | gag | gtg | att | ggg | ctg | tac | ggc | 5077 |
| Ser | Pro | Ile | Val | Asn | Arg | Asn | Gly | Glu | Val | Ile | Gly | Leu | Tyr | Gly |  |
|  | 1640 |  |  |  | 1645 |  |  |  | 1650 |  |  |  |
| aat | ggc | atc | ctt | gtc | ggt | gac | aac | tcc | ttc | gtg | tcc | gcc | ata | tcc | 5122 |
| Asn | Gly | Ile | Leu | Val | Gly | Asp | Asn | Ser | Phe | Val | Ser | Ala | Ile | Ser |  |
| 1655 |  |  |  | 1660 |  |  |  | 1665 |  |  |  |
| cag | act | gag | gtg | aag | gaa | gaa | gga | aag | gag | gag | ctc | caa | gag | atc | 5167 |
| Gln | Thr | Glu | Val | Lys | Glu | Glu | Gly | Lys | Glu | Glu | Leu | Gln | Glu | Ile |  |
|  | 1670 |  |  |  | 1675 |  |  |  | 1680 |  |  |  |
| ccg | aca | atg | cta | aag | aaa | gga | atg | aca | act | gtc | ctt | gat | ttt | cat | 5212 |
| Pro | Thr | Met | Leu | Lys | Lys | Gly | Met | Thr | Thr | Val | Leu | Asp | Phe | His |  |
| 1685 |  |  |  | 1690 |  |  |  | 1695 |  |  |  |
| cct | gga | gct | ggg | aag | aca | aga | cgt | ttc | ctc | cca | cag | atc | ttg | gcc | 5257 |
| Pro | Gly | Ala | Gly | Lys | Thr | Arg | Arg | Phe | Leu | Pro | Gln | Ile | Leu | Ala |  |
|  | 1700 |  |  |  | 1705 |  |  |  | 1710 |  |  |  |
| gag | tgc | gca | cgg | aga | cgc | ttg | cgc | act | ctt | gtg | ttg | gcc | ccc | acc | 5302 |
| Glu | Cys | Ala | Arg | Arg | Arg | Leu | Arg | Thr | Leu | Val | Leu | Ala | Pro | Thr |  |
| 1715 |  |  |  | 1720 |  |  |  | 1725 |  |  |  |
| agg | gtt | gtt | ctt | tct | gaa | atg | aag | gag | gct | ttt | cac | ggc | ctg | gac | 5347 |
| Arg | Val | Val | Leu | Ser | Glu | Met | Lys | Glu | Ala | Phe | His | Gly | Leu | Asp |  |
|  | 1730 |  |  |  | 1735 |  |  |  | 1740 |  |  |  |
| gtg | aaa | ttc | cac | aca | cag | gct | ttt | tcc | gct | cac | ggc | agc | ggg | aga | 5392 |
| Val | Lys | Phe | His | Thr | Gln | Ala | Phe | Ser | Ala | His | Gly | Ser | Gly | Arg |  |
| 1745 |  |  |  | 1750 |  |  |  | 1755 |  |  |  |
| gaa | gtc | att | gat | gcc | atg | tgc | cat | gcc | acc | cta | act | tac | agg | atg | 5437 |
| Glu | Val | Ile | Asp | Ala | Met | Cys | His | Ala | Thr | Leu | Thr | Tyr | Arg | Met |  |
|  | 1760 |  |  |  | 1765 |  |  |  | 1770 |  |  |  |
| ttg | gaa | cca | act | agg | gtt | gtt | aac | tgg | gaa | gtg | atc | att | atg | gat | 5482 |
| Leu | Glu | Pro | Thr | Arg | Val | Val | Asn | Trp | Glu | Val | Ile | Ile | Met | Asp |  |
| 1775 |  |  |  | 1780 |  |  |  | 1785 |  |  |  |
| gaa | gcc | cat | ttt | ttg | gat | cca | gct | agc | ata | gcc | gct | aga | ggt | tgg | 5527 |
| Glu | Ala | His | Phe | Leu | Asp | Pro | Ala | Ser | Ile | Ala | Ala | Arg | Gly | Trp |  |
|  | 1790 |  |  |  | 1795 |  |  |  | 1800 |  |  |  |
| gca | gcg | cac | aga | gct | agg | gca | aat | gaa | agt | gca | aca | atc | ttg | atg | 5572 |
| Ala | Ala | His | Arg | Ala | Arg | Ala | Asn | Glu | Ser | Ala | Thr | Ile | Leu | Met |  |
| 1805 |  |  |  | 1810 |  |  |  | 1815 |  |  |  |
| aca | gcc | aca | ccg | cct | ggg | act | agt | gat | gaa | ttt | cca | cat | tca | aat | 5617 |
| Thr | Ala | Thr | Pro | Pro | Gly | Thr | Ser | Asp | Glu | Phe | Pro | His | Ser | Asn |  |
|  | 1820 |  |  |  | 1825 |  |  |  | 1830 |  |  |  |
| ggt | gaa | ata | gaa | gat | gtt | caa | acg | gac | ata | ccc | agt | gag | ccc | tgg | 5662 |

```
                Gly Glu Ile Glu Asp Val Gln Thr Asp Ile Pro Ser Glu Pro Trp
                    1835                1840                1845 aac aca ggg cat gac tgg atc ctg gct gac aaa agg ccc acg gca         5707
Asn Thr Gly His Asp Trp Ile Leu Ala Asp Lys Arg Pro Thr Ala
    1850                1855                1860 tgg ttc ctt cca tcc atc aga gct gca aat gtc atg gct gcc tct         5752
Trp Phe Leu Pro Ser Ile Arg Ala Ala Asn Val Met Ala Ala Ser
    1865                1870                1875 ttg cgt aag gct gga aag agt gtg gtg gtc ctg aac agg aaa acc         5797
Leu Arg Lys Ala Gly Lys Ser Val Val Val Leu Asn Arg Lys Thr
    1880                1885                1890 ttt gag aga gaa tac ccc acg ata aag cag aag aaa cct gac ttt         5842
Phe Glu Arg Glu Tyr Pro Thr Ile Lys Gln Lys Lys Pro Asp Phe
    1895                1900                1905 ata ttg gcc act gac ata gct gaa atg gga gcc aac ctt tgc gtg         5887
Ile Leu Ala Thr Asp Ile Ala Glu Met Gly Ala Asn Leu Cys Val
    1910                1915                1920 gag cga gtg ctg gat tgc agg acg gct ttt aag cct gtg ctt gtg         5932
Glu Arg Val Leu Asp Cys Arg Thr Ala Phe Lys Pro Val Leu Val
    1925                1930                1935 gat gaa ggg agg aag gtg gca ata aaa ggg cca ctt cgt atc tcc         5977
Asp Glu Gly Arg Lys Val Ala Ile Lys Gly Pro Leu Arg Ile Ser
    1940                1945                1950 gca tcc tct gct gct caa agg agg ggg cgc att ggg aga aat ccc         6022
Ala Ser Ser Ala Ala Gln Arg Arg Gly Arg Ile Gly Arg Asn Pro
    1955                1960                1965 aac aga gat gga gac tca tac tac tat tct gag cct aca agt gaa         6067
Asn Arg Asp Gly Asp Ser Tyr Tyr Tyr Ser Glu Pro Thr Ser Glu
    1970                1975                1980 aat aat gcc cac cac gtc tgc tgg ttg gag gcc tca atg ctc ttg         6112
Asn Asn Ala His His Val Cys Trp Leu Glu Ala Ser Met Leu Leu
    1985                1990                1995 gac aac atg gag gtg agg ggt gga atg gtc gcc cca ctc tat ggc         6157
Asp Asn Met Glu Val Arg Gly Gly Met Val Ala Pro Leu Tyr Gly
    2000                2005                2010 gtt gaa gga act aaa aca cca gtt tcc cct ggt gaa atg aga ctg         6202
Val Glu Gly Thr Lys Thr Pro Val Ser Pro Gly Glu Met Arg Leu
    2015                2020                2025 agg gat gac cag agg aaa gtc ttc aga gaa cta gtg agg aat tgt         6247
Arg Asp Asp Gln Arg Lys Val Phe Arg Glu Leu Val Arg Asn Cys
    2030                2035                2040 gac ctg ccc gtt tgg ctt tcg tgg caa gtg gcc aag gct ggt ttg         6292
Asp Leu Pro Val Trp Leu Ser Trp Gln Val Ala Lys Ala Gly Leu
    2045                2050                2055 aag acg aat gat cgt aag tgg tgt ttt gaa ggc cct gag gaa cat         6337
Lys Thr Asn Asp Arg Lys Trp Cys Phe Glu Gly Pro Glu Glu His
    2060                2065                2070 gag atc ttg aat gac agc ggt gaa aca gtg aag tgc agg gct cct         6382
Glu Ile Leu Asn Asp Ser Gly Glu Thr Val Lys Cys Arg Ala Pro
    2075                2080                2085 gga gga gca aag aag cct ctg cgc cca agg tgg tgt gat gaa agg         6427
Gly Gly Ala Lys Lys Pro Leu Arg Pro Arg Trp Cys Asp Glu Arg
    2090                2095                2100 gtg tca tct gac cag agt gcg ctg tct gaa ttt att aag ttt gct         6472
Val Ser Ser Asp Gln Ser Ala Leu Ser Glu Phe Ile Lys Phe Ala
    2105                2110                2115 gaa ggt agg agg gga gct gct gaa gtg cta gtt gtg ctg agt gaa         6517
Glu Gly Arg Arg Gly Ala Ala Glu Val Leu Val Val Leu Ser Glu
    2120                2125                2130
```

| | | | | | | | | | | | | | |
|---|---|---|---|---|---|---|---|---|---|---|---|---|---|
| ctc | cct | gat | ttc | ctg | gct | aaa | aaa | ggt | gga | gag | gca | atg gat acc | 6562 |
| Leu | Pro | Asp | Phe | Leu | Ala | Lys | Lys | Gly | Gly | Glu | Ala | Met Asp Thr | |
| | | 2135 | | | | 2140 | | | | | 2145 | | |
| atc | agt | gtg | ttc | ctc | cac | tct | gag | gaa | ggc | tct | agg | gct tac cgc | 6607 |
| Ile | Ser | Val | Phe | Leu | His | Ser | Glu | Glu | Gly | Ser | Arg | Ala Tyr Arg | |
| | 2150 | | | | | 2155 | | | | | 2160 | | |
| aat | gca | cta | tca | atg | atg | cct | gag | gca | atg | aca | ata | gtc atg ctg | 6652 |
| Asn | Ala | Leu | Ser | Met | Met | Pro | Glu | Ala | Met | Thr | Ile | Val Met Leu | |
| | 2165 | | | | | 2170 | | | | | 2175 | | |
| ttt | ata | ctg | gct | gga | cta | ctg | aca | tcg | gga | atg | gtc | atc ttt ttc | 6697 |
| Phe | Ile | Leu | Ala | Gly | Leu | Leu | Thr | Ser | Gly | Met | Val | Ile Phe Phe | |
| | 2180 | | | | | 2185 | | | | | 2190 | | |
| atg | tct | ccc | aaa | ggc | atc | agt | aga | atg | tct | atg | gcg | atg ggc aca | 6742 |
| Met | Ser | Pro | Lys | Gly | Ile | Ser | Arg | Met | Ser | Met | Ala | Met Gly Thr | |
| | 2195 | | | | | 2200 | | | | | 2205 | | |
| atg | gcc | ggc | tgt | gga | tat | ctc | atg | ttc | ctt | gga | ggc | gtc aaa ccc | 6787 |
| Met | Ala | Gly | Cys | Gly | Tyr | Leu | Met | Phe | Leu | Gly | Gly | Val Lys Pro | |
| | 2210 | | | | | 2215 | | | | | 2220 | | |
| act | cac | atc | tcc | tat | gtc | atg | ctc | ata | ttc | ttt | gtc | ctg atg gtg | 6832 |
| Thr | His | Ile | Ser | Tyr | Val | Met | Leu | Ile | Phe | Phe | Val | Leu Met Val | |
| | 2225 | | | | | 2230 | | | | | 2235 | | |
| gtt | gtg | atc | ccc | gag | cca | ggg | caa | caa | agg | tcc | atc | caa gac aac | 6877 |
| Val | Val | Ile | Pro | Glu | Pro | Gly | Gln | Gln | Arg | Ser | Ile | Gln Asp Asn | |
| | 2240 | | | | | 2245 | | | | | 2250 | | |
| caa | gtg | gca | tac | ctc | att | att | ggc | atc | ctg | acg | ctg | gtt tca gcg | 6922 |
| Gln | Val | Ala | Tyr | Leu | Ile | Ile | Gly | Ile | Leu | Thr | Leu | Val Ser Ala | |
| | 2255 | | | | | 2260 | | | | | 2265 | | |
| gtg | gca | gcc | aac | gag | cta | ggc | atg | ctg | gag | aaa | acc | aaa gag gac | 6967 |
| Val | Ala | Ala | Asn | Glu | Leu | Gly | Met | Leu | Glu | Lys | Thr | Lys Glu Asp | |
| | 2270 | | | | | 2275 | | | | | 2280 | | |
| ctc | ttt | ggg | aag | aag | aac | tta | att | cca | tct | agt | gct | tca ccc tgg | 7012 |
| Leu | Phe | Gly | Lys | Lys | Asn | Leu | Ile | Pro | Ser | Ser | Ala | Ser Pro Trp | |
| | 2285 | | | | | 2290 | | | | | 2295 | | |
| agt | tgg | ccg | gat | ctt | gac | ctg | aag | cca | gga | gct | gcc | tgg aca gtg | 7057 |
| Ser | Trp | Pro | Asp | Leu | Asp | Leu | Lys | Pro | Gly | Ala | Ala | Trp Thr Val | |
| | 2300 | | | | | 2305 | | | | | 2310 | | |
| tac | gtt | ggc | att | gtt | aca | atg | ctc | tct | cca | atg | ttg | cac cac tgg | 7102 |
| Tyr | Val | Gly | Ile | Val | Thr | Met | Leu | Ser | Pro | Met | Leu | His His Trp | |
| | 2315 | | | | | 2320 | | | | | 2325 | | |
| atc | aaa | gtc | gaa | tat | ggc | aac | ctg | tct | ctg | tct | gga | ata gcc cag | 7147 |
| Ile | Lys | Val | Glu | Tyr | Gly | Asn | Leu | Ser | Leu | Ser | Gly | Ile Ala Gln | |
| | 2330 | | | | | 2335 | | | | | 2340 | | |
| tca | gcc | tca | gtc | ctt | tct | ttc | atg | gac | aag | ggg | ata | cca ttc atg | 7192 |
| Ser | Ala | Ser | Val | Leu | Ser | Phe | Met | Asp | Lys | Gly | Ile | Pro Phe Met | |
| | 2345 | | | | | 2350 | | | | | 2355 | | |
| aag | atg | aat | atc | tcg | gtc | ata | atg | ctg | ctg | gtc | agt | ggc tgg aat | 7237 |
| Lys | Met | Asn | Ile | Ser | Val | Ile | Met | Leu | Leu | Val | Ser | Gly Trp Asn | |
| | 2360 | | | | | 2365 | | | | | 2370 | | |
| tca | ata | aca | gtg | atg | cct | ctg | ctc | tgt | ggc | ata | ggg | tgc gcc atg | 7282 |
| Ser | Ile | Thr | Val | Met | Pro | Leu | Leu | Cys | Gly | Ile | Gly | Cys Ala Met | |
| | 2375 | | | | | 2380 | | | | | 2385 | | |
| ctc | cac | tgg | tct | ctc | att | tta | cct | gga | atc | aaa | gcg | cag cag tca | 7327 |
| Leu | His | Trp | Ser | Leu | Ile | Leu | Pro | Gly | Ile | Lys | Ala | Gln Gln Ser | |
| | 2390 | | | | | 2395 | | | | | 2400 | | |
| aag | cta | gca | cag | aga | agg | gtg | ttc | cat | ggc | gtt | gcc | aag aac cct | 7372 |
| Lys | Leu | Ala | Gln | Arg | Arg | Val | Phe | His | Gly | Val | Ala | Lys Asn Pro | |
| | 2405 | | | | | 2410 | | | | | 2415 | | |
| gtg | gtt | gat | ggg | aat | cca | aca | gtt | gac | att | gag | gaa | gct cct gaa | 7417 |
| Val | Val | Asp | Gly | Asn | Pro | Thr | Val | Asp | Ile | Glu | Glu | Ala Pro Glu | |
| | 2420 | | | | | 2425 | | | | | 2430 | | |

| | | | | | | | | | | | | | | |
|---|---|---|---|---|---|---|---|---|---|---|---|---|---|---|
| atg | cct | gcc | ctt | tat | gag | aag | aaa | ctg | gct | cta | tat | ctc | ctt | ctt | 7462 |
| Met | Pro | Ala | Leu | Tyr | Glu | Lys | Lys | Leu | Ala | Leu | Tyr | Leu | Leu | Leu | |
| | 2435 | | | | 2440 | | | | | 2445 | | | | | |
| gct | ctc | agc | cta | gct | tct | gtt | gcc | atg | tgc | aga | acg | ccc | ttt | tca | 7507 |
| Ala | Leu | Ser | Leu | Ala | Ser | Val | Ala | Met | Cys | Arg | Thr | Pro | Phe | Ser | |
| | | 2450 | | | | | 2455 | | | | | 2460 | | | |
| ttg | gct | gaa | ggc | att | gtc | cta | gca | tca | gct | gcc | tta | ggg | ccg | ctc | 7552 |
| Leu | Ala | Glu | Gly | Ile | Val | Leu | Ala | Ser | Ala | Ala | Leu | Gly | Pro | Leu | |
| | 2465 | | | | | 2470 | | | | | 2475 | | | | |
| ata | gag | gga | aac | acc | agc | ctt | ctt | tgg | aat | gga | ccc | atg | gct | gtc | 7597 |
| Ile | Glu | Gly | Asn | Thr | Ser | Leu | Leu | Trp | Asn | Gly | Pro | Met | Ala | Val | |
| | | 2480 | | | | | 2485 | | | | | 2490 | | | |
| tcc | atg | aca | gga | gtc | atg | agg | ggg | aat | cac | tat | gct | ttt | gtg | gga | 7642 |
| Ser | Met | Thr | Gly | Val | Met | Arg | Gly | Asn | His | Tyr | Ala | Phe | Val | Gly | |
| | 2495 | | | | | 2500 | | | | | 2505 | | | | |
| gtc | atg | tac | aat | cta | tgg | aag | atg | aaa | act | gga | cgc | cgg | ggg | agc | 7687 |
| Val | Met | Tyr | Asn | Leu | Trp | Lys | Met | Lys | Thr | Gly | Arg | Arg | Gly | Ser | |
| | 2510 | | | | | 2515 | | | | | 2520 | | | | |
| gcg | aat | gga | aaa | act | ttg | ggt | gaa | gtc | tgg | aag | agg | gaa | ctg | aat | 7732 |
| Ala | Asn | Gly | Lys | Thr | Leu | Gly | Glu | Val | Trp | Lys | Arg | Glu | Leu | Asn | |
| | 2525 | | | | | 2530 | | | | | 2535 | | | | |
| ctg | ttg | gac | aag | cga | cag | ttt | gag | ttg | tat | aaa | agg | acc | gac | att | 7777 |
| Leu | Leu | Asp | Lys | Arg | Gln | Phe | Glu | Leu | Tyr | Lys | Arg | Thr | Asp | Ile | |
| | 2540 | | | | | 2545 | | | | | 2550 | | | | |
| gtg | gag | gtg | gat | cgt | gat | acg | gca | cgc | agg | cat | ttg | gcc | gaa | ggg | 7822 |
| Val | Glu | Val | Asp | Arg | Asp | Thr | Ala | Arg | Arg | His | Leu | Ala | Glu | Gly | |
| | 2555 | | | | | 2560 | | | | | 2565 | | | | |
| aag | gtg | gac | acc | ggg | gtg | gcg | gtc | tcc | agg | ggg | acc | gca | aag | tta | 7867 |
| Lys | Val | Asp | Thr | Gly | Val | Ala | Val | Ser | Arg | Gly | Thr | Ala | Lys | Leu | |
| | 2570 | | | | | 2575 | | | | | 2580 | | | | |
| agg | tgg | ttc | cat | gag | cgt | ggc | tat | gtc | aag | ctg | gaa | ggt | agg | gtg | 7912 |
| Arg | Trp | Phe | His | Glu | Arg | Gly | Tyr | Val | Lys | Leu | Glu | Gly | Arg | Val | |
| | 2585 | | | | | 2590 | | | | | 2595 | | | | |
| att | gac | ctg | ggg | tgt | ggc | cgc | gga | ggc | tgg | tgt | tac | tac | gct | gct | 7957 |
| Ile | Asp | Leu | Gly | Cys | Gly | Arg | Gly | Gly | Trp | Cys | Tyr | Tyr | Ala | Ala | |
| | 2600 | | | | | 2605 | | | | | 2610 | | | | |
| gcg | caa | aag | gaa | gtg | agt | ggg | gtc | aaa | gga | ttt | act | ctt | gga | aga | 8002 |
| Ala | Gln | Lys | Glu | Val | Ser | Gly | Val | Lys | Gly | Phe | Thr | Leu | Gly | Arg | |
| | 2615 | | | | | 2620 | | | | | 2625 | | | | |
| gac | ggc | cat | gag | aaa | ccc | atg | aat | gtg | caa | agt | ctg | gga | tgg | aac | 8047 |
| Asp | Gly | His | Glu | Lys | Pro | Met | Asn | Val | Gln | Ser | Leu | Gly | Trp | Asn | |
| | 2630 | | | | | 2635 | | | | | 2640 | | | | |
| atc | atc | acc | ttc | aag | gac | aaa | act | gat | atc | cac | cgc | cta | gaa | cca | 8092 |
| Ile | Ile | Thr | Phe | Lys | Asp | Lys | Thr | Asp | Ile | His | Arg | Leu | Glu | Pro | |
| | 2645 | | | | | 2650 | | | | | 2655 | | | | |
| gtg | aaa | tgt | gac | acc | ctt | ttg | tgt | gac | att | gga | gag | tca | tca | tcg | 8137 |
| Val | Lys | Cys | Asp | Thr | Leu | Leu | Cys | Asp | Ile | Gly | Glu | Ser | Ser | Ser | |
| | 2660 | | | | | 2665 | | | | | 2670 | | | | |
| tca | tcg | gtc | aca | gag | ggg | gaa | agg | acc | gtg | aga | gtt | ctt | gat | act | 8182 |
| Ser | Ser | Val | Thr | Glu | Gly | Glu | Arg | Thr | Val | Arg | Val | Leu | Asp | Thr | |
| | 2675 | | | | | 2680 | | | | | 2685 | | | | |
| gta | gaa | aaa | tgg | ctg | gct | tgt | ggg | gtt | gac | aac | ttc | tgt | gtg | aag | 8227 |
| Val | Glu | Lys | Trp | Leu | Ala | Cys | Gly | Val | Asp | Asn | Phe | Cys | Val | Lys | |
| | 2690 | | | | | 2695 | | | | | 2700 | | | | |
| gtg | tta | gct | cca | tac | atg | cca | gat | gtt | ctt | gag | aaa | ctg | gaa | ttg | 8272 |
| Val | Leu | Ala | Pro | Tyr | Met | Pro | Asp | Val | Leu | Glu | Lys | Leu | Glu | Leu | |
| | 2705 | | | | | 2710 | | | | | 2715 | | | | |
| ctc | caa | agg | agg | ttt | ggc | gga | aca | gtg | atc | agg | aac | cct | ctc | tcc | 8317 |
| Leu | Gln | Arg | Arg | Phe | Gly | Gly | Thr | Val | Ile | Arg | Asn | Pro | Leu | Ser | |

-continued

```
                2720                2725                2730
agg aat tcc act cat gaa atg tac tac gtg tct gga gcc cgc agc          8362
Arg Asn Ser Thr His Glu Met Tyr Tyr Val Ser Gly Ala Arg Ser
        2735                2740                2745 aat gtc aca ttt act gtg aac caa aca tcc cgc ctc ctg atg agg          8407
Asn Val Thr Phe Thr Val Asn Gln Thr Ser Arg Leu Leu Met Arg
    2750                2755                2760 aga atg agg cgt cca act gga aaa gtg acc ctg gag gct gac gtc          8452
Arg Met Arg Arg Pro Thr Gly Lys Val Thr Leu Glu Ala Asp Val
2765                2770                2775 atc ctc cca att ggg aca cgc agt gtt gag aca gac aag gga ccc          8497
Ile Leu Pro Ile Gly Thr Arg Ser Val Glu Thr Asp Lys Gly Pro
        2780                2785                2790 ctg gac aaa gag gcc ata gaa gaa agg gtt gag agg ata aaa tct          8542
Leu Asp Lys Glu Ala Ile Glu Glu Arg Val Glu Arg Ile Lys Ser
    2795                2800                2805 gag tac atg acc tct tgg ttt tat gac aat gac aac ccc tac agg          8587
Glu Tyr Met Thr Ser Trp Phe Tyr Asp Asn Asp Asn Pro Tyr Arg
2810                2815                2820 acc tgg cac tac tgt ggc tcg tac gtc aca aaa acc tca gga agt          8632
Thr Trp His Tyr Cys Gly Ser Tyr Val Thr Lys Thr Ser Gly Ser
        2825                2830                2835 gcg gcg agc atg gta aat ggt gtt att aaa att ctg aca tat cca          8677
Ala Ala Ser Met Val Asn Gly Val Ile Lys Ile Leu Thr Tyr Pro
    2840                2845                2850 tgg gac agg ata gag gag gtc aca aga atg gca atg act gac aca          8722
Trp Asp Arg Ile Glu Glu Val Thr Arg Met Ala Met Thr Asp Thr
2855                2860                2865 acc cct ttt gga cag caa aga gtg ttt aaa gaa aaa gtt gac acc          8767
Thr Pro Phe Gly Gln Gln Arg Val Phe Lys Glu Lys Val Asp Thr
        2870                2875                2880 aga gca aag gat cca cca gcg gga act agg aag atc atg aaa gtt          8812
Arg Ala Lys Asp Pro Pro Ala Gly Thr Arg Lys Ile Met Lys Val
    2885                2890                2895 gtc aac agg tgg ctg ttc cgc cac ctg gcc aga gaa aag aac ccc          8857
Val Asn Arg Trp Leu Phe Arg His Leu Ala Arg Glu Lys Asn Pro
2900                2905                2910 aga ctg tgc aca aag gaa gaa ttt att gca aaa gtc cga agt cat          8902
Arg Leu Cys Thr Lys Glu Glu Phe Ile Ala Lys Val Arg Ser His
        2915                2920                2925 gca gcc att gga gct tac ctg gaa gaa caa gaa cag tgg aag act          8947
Ala Ala Ile Gly Ala Tyr Leu Glu Glu Gln Glu Gln Trp Lys Thr
    2930                2935                2940 gcc aat gag gct gtc caa gac cca aag ttc tgg gaa ctg gtg gat          8992
Ala Asn Glu Ala Val Gln Asp Pro Lys Phe Trp Glu Leu Val Asp
2945                2950                2955 gaa gaa agg aag ctg cac caa caa ggc agg tgt cgg act tgt gtg          9037
Glu Glu Arg Lys Leu His Gln Gln Gly Arg Cys Arg Thr Cys Val
        2960                2965                2970 tac aac atg atg ggg aaa aga gag aag aag ctg tca gag ttt ggg          9082
Tyr Asn Met Met Gly Lys Arg Glu Lys Lys Leu Ser Glu Phe Gly
    2975                2980                2985 aaa gca aag gga agc cgt gcc ata tgg tat atg tgg ctg gga gcg          9127
Lys Ala Lys Gly Ser Arg Ala Ile Trp Tyr Met Trp Leu Gly Ala
2990                2995                3000 cgg tat ctt gag ttt gag gcc ctg gga ttc ctg aat gag gac cat          9172
Arg Tyr Leu Glu Phe Glu Ala Leu Gly Phe Leu Asn Glu Asp His
        3005                3010                3015 tgg gct tcc agg gaa aac tca gga gga gga gtg gaa ggc att ggc          9217
```

-continued

| | | | | | | | | | | | | |
|---|---|---|---|---|---|---|---|---|---|---|---|---|
| Trp | Ala | Ser | Arg | Glu | Asn | Ser | Gly | Gly | Gly | Val | Glu | Gly | Ile | Gly |
| | 3020 | | | | 3025 | | | | 3030 | | | |

```
tta caa tac cta gga tat gtg atc aga gac ctg gct gca atg gat         9262
Leu Gln Tyr Leu Gly Tyr Val Ile Arg Asp Leu Ala Ala Met Asp
    3035                3040                3045 ggt ggt gga ttc tac gcg gat gac acc gct gga tgg gac acg cgc         9307
Gly Gly Gly Phe Tyr Ala Asp Asp Thr Ala Gly Trp Asp Thr Arg
    3050                3055                3060 atc aca gag gca gac ctt gat gat gaa cag gag atc ttg aac tac         9352
Ile Thr Glu Ala Asp Leu Asp Asp Glu Gln Glu Ile Leu Asn Tyr
    3065                3070                3075 atg agc cca cat cac aaa aaa ctg gca caa gca gtg atg gaa atg         9397
Met Ser Pro His His Lys Lys Leu Ala Gln Ala Val Met Glu Met
    3080                3085                3090 aca tac aag aac aaa gtg gtg aaa gtg ttg aga cca gcc cca gga         9442
Thr Tyr Lys Asn Lys Val Val Lys Val Leu Arg Pro Ala Pro Gly
    3095                3100                3105 ggg aaa gcc tac atg gat gtc ata agt cga cga gac cag aga gga         9487
Gly Lys Ala Tyr Met Asp Val Ile Ser Arg Arg Asp Gln Arg Gly
    3110                3115                3120 tcc ggg cag gta gtg act tat gct ctg aac acc atc acc aac ttg         9532
Ser Gly Gln Val Val Thr Tyr Ala Leu Asn Thr Ile Thr Asn Leu
    3125                3130                3135 aaa gtc caa ttg atc aga atg gca gaa gca gag atg gtg ata cat         9577
Lys Val Gln Leu Ile Arg Met Ala Glu Ala Glu Met Val Ile His
    3140                3145                3150 cac caa cat gtt caa gat tgt gat gaa tca gtt ctg acc agg ctg         9622
His Gln His Val Gln Asp Cys Asp Glu Ser Val Leu Thr Arg Leu
    3155                3160                3165 gag gca tgg ctc act gag cac gga tgt gac aga ctg aag agg atg         9667
Glu Ala Trp Leu Thr Glu His Gly Cys Asp Arg Leu Lys Arg Met
    3170                3175                3180 gcg gtg agt gga gac gac tgt gtg gtc cgg ccc atc gat gac agg         9712
Ala Val Ser Gly Asp Asp Cys Val Val Arg Pro Ile Asp Asp Arg
    3185                3190                3195 ttc ggc ctg gcc ctg tcc cat ctc aac gcc atg tcc aag gtt aga         9757
Phe Gly Leu Ala Leu Ser His Leu Asn Ala Met Ser Lys Val Arg
    3200                3205                3210 aag gac ata tct gaa tgg cag cca tca aaa ggg tgg aat gat tgg         9802
Lys Asp Ile Ser Glu Trp Gln Pro Ser Lys Gly Trp Asn Asp Trp
    3215                3220                3225 gag aat gtg ccc ttc tgt tcc cac cac ttc cat gaa cta cag ctg         9847
Glu Asn Val Pro Phe Cys Ser His His Phe His Glu Leu Gln Leu
    3230                3235                3240 aag gat ggc agg agg att gtg gtg cct tgc cga gaa cag gac gag         9892
Lys Asp Gly Arg Arg Ile Val Val Pro Cys Arg Glu Gln Asp Glu
    3245                3250                3255 ctc att ggg aga gga agg gtg tct cca gga aac ggc tgg atg atc         9937
Leu Ile Gly Arg Gly Arg Val Ser Pro Gly Asn Gly Trp Met Ile
    3260                3265                3270 aag gaa aca gct tgc ctc agc aaa gcc tat gcc aac atg tgg tca         9982
Lys Glu Thr Ala Cys Leu Ser Lys Ala Tyr Ala Asn Met Trp Ser
    3275                3280                3285 ctg atg tat ttt cac aaa agg gac atg agg cta ctg tca ttg gct        10027
Leu Met Tyr Phe His Lys Arg Asp Met Arg Leu Leu Ser Leu Ala
    3290                3295                3300 gtt tcc tca gct gtt ccc acc tca tgg gtt cca caa gga cgc aca        10072
Val Ser Ser Ala Val Pro Thr Ser Trp Val Pro Gln Gly Arg Thr
    3305                3310                3315
```

```
aca tgg tcg att cat ggg aaa ggg gag tgg atg acc acg gaa gac      10117
Thr Trp Ser Ile His Gly Lys Gly Glu Trp Met Thr Thr Glu Asp
3320            3325                3330 atg ctt gag gtg tgg aac aga gta tgg ata acc aac aac cca cac      10162
Met Leu Glu Val Trp Asn Arg Val Trp Ile Thr Asn Asn Pro His
    3335                3340                3345 atg cag gac aag aca atg gtg aaa aaa tgg aga gat gtc cct tat      10207
Met Gln Asp Lys Thr Met Val Lys Lys Trp Arg Asp Val Pro Tyr
3350            3355                3360 cta acc aag aga caa gac aag ctg tgc gga tca ctg att gga atg      10252
Leu Thr Lys Arg Gln Asp Lys Leu Cys Gly Ser Leu Ile Gly Met
    3365                3370                3375 acc aat agg gcc acc tgg gcc tcc cac atc cat tta gtc atc cat      10297
Thr Asn Arg Ala Thr Trp Ala Ser His Ile His Leu Val Ile His
3380            3385                3390 cgt atc cga acg ctg att gga cag gag aaa tac act gac tac cta      10342
Arg Ile Arg Thr Leu Ile Gly Gln Glu Lys Tyr Thr Asp Tyr Leu
    3395                3400                3405 aca gtc atg gac agg tat tct gtg gat gct gac ctg caa ctg ggt      10387
Thr Val Met Asp Arg Tyr Ser Val Asp Ala Asp Leu Gln Leu Gly
3410            3415                3420 gag ctt atc tga aacaccatct aacaggaata accgggatac aaaccacggg      10439
Glu Leu Ile
3425 tggagaaccg gactccccac aacctgaaac cgggatataa accacggctg gagaaccgga   10499 ctccgcactt aaaatgaaac agaaaccggg ataaaaacta cggatggaga accggactcc   10559 acacattgag acagaagaag ttgtcagccc agaaccccac acgagttttg ccactgctaa   10619 gctgtgaggc agtgcaggct gggacagccg acctccaggt tgcgaaaaac ctggtttctg   10679 ggacctccca ccccagagta aaaagaacgg agcctccgct accaccctcc cacgtggtgg   10739 tagaaagacg gggtctagag gttagaggag accctccagg gaacaaatag tgggaccata   10799 ttgacgccag ggaaagaccg gagtggttct ctgcttttcc tccagaggtc tgtgagcaca   10859 gtttgctcaa gaataagcag acctttggat gacaaacaca aaaccact                10907

<210> SEQ ID NO 2
<211> LENGTH: 3426
<212> TYPE: PRT
<213> ORGANISM: Artificial Sequence
<220> FEATURE:
<221> NAME/KEY: misc_feature
<222> LOCATION: (327)..(327)
<223> OTHER INFORMATION: The 'Xaa' at location 327 stands for Ala, or
      Thr.
<220> FEATURE:
<223> OTHER INFORMATION: Synthetic Construct

<400> SEQUENCE: 2

Met Ser Gly Arg Lys Ala Gln Gly Lys Thr Leu Gly Val Asn Met Val
1               5                   10                  15

Arg Arg Gly Val Arg Ser Leu Ser Asn Lys Ile Lys Gln Lys Thr Lys
                20                  25                  30

Gln Ile Gly Asn Arg Pro Gly Pro Ser Arg Gly Val Gln Gly Phe Ile
            35                  40                  45

Phe Phe Phe Leu Phe Asn Ile Leu Thr Gly Lys Lys Ile Thr Ala His
        50                  55                  60

Leu Lys Arg Leu Trp Lys Met Leu Asp Pro Arg Gln Gly Leu Ala Val
65              70                  75                  80

Leu Arg Lys Val Lys Arg Val Val Ala Ser Leu Met Arg Gly Leu Ser
```

```
                85                  90                  95
Ser Arg Lys Arg Arg Gly Thr Asp Thr Ser Val Gly Ile Val Gly Leu
            100                 105                 110

Leu Leu Thr Thr Ala Met Ala Val Glu Val Thr Arg Arg Gly Ser Ala
            115                 120                 125

Tyr Tyr Met Tyr Leu Asp Arg Ser Asp Ala Gly Glu Ala Ile Ser Phe
            130                 135                 140

Pro Thr Thr Leu Gly Met Asn Lys Cys Tyr Ile Gln Ile Met Asp Leu
145                 150                 155                 160

Gly His Met Cys Asp Ala Thr Met Ser Tyr Glu Cys Pro Met Leu Asp
                165                 170                 175

Glu Gly Val Glu Pro Asp Val Asp Cys Trp Cys Asn Thr Thr Ser
                180                 185                 190

Thr Trp Val Val Tyr Gly Thr Cys His His Lys Lys Gly Glu Ala Arg
            195                 200                 205

Arg Ser Arg Arg Ala Val Thr Leu Pro Ser His Ser Thr Arg Lys Leu
            210                 215                 220

Gln Thr Arg Ser Gln Thr Trp Leu Glu Ser Arg Glu Tyr Thr Lys His
225                 230                 235                 240

Leu Ile Arg Val Glu Asn Trp Ile Phe Arg Asn Pro Gly Phe Ala Leu
                245                 250                 255

Ala Ala Ala Ala Ile Ala Trp Leu Leu Gly Ser Ser Thr Ser Gln Lys
            260                 265                 270

Val Ile Tyr Leu Val Met Ile Leu Leu Ile Ala Pro Ala Tyr Ser Ile
            275                 280                 285

Arg Cys Ile Gly Val Ser Asn Arg Asp Phe Val Glu Gly Met Ser Gly
            290                 295                 300

Gly Thr Trp Val Asp Val Val Leu Glu His Gly Gly Cys Val Thr Val
305                 310                 315                 320

Met Ala Gln Asp Lys Pro Xaa Val Asp Ile Glu Leu Val Thr Thr Thr
                325                 330                 335

Val Ser Asn Met Ala Glu Val Arg Ser Tyr Cys Tyr Glu Ala Ser Ile
            340                 345                 350

Ser Asp Met Ala Ser Asp Ser Arg Cys Pro Thr Gln Gly Glu Ala Tyr
            355                 360                 365

Leu Asp Lys Gln Ser Asp Thr Gln Tyr Val Cys Lys Arg Thr Leu Val
370                 375                 380

Asp Arg Gly Trp Gly Asn Gly Cys Gly Leu Phe Gly Lys Gly Ser Leu
385                 390                 395                 400

Val Thr Cys Ala Lys Phe Ala Cys Ser Lys Lys Met Thr Gly Lys Ser
            405                 410                 415

Ile Gln Pro Glu Asn Leu Glu Tyr Arg Ile Met Leu Ser Val His Gly
            420                 425                 430

Ser Gln His Ser Gly Met Ile Val Asn Asp Thr Gly His Glu Thr Asp
            435                 440                 445

Glu Asn Arg Ala Lys Val Glu Ile Thr Pro Asn Ser Pro Arg Ala Glu
            450                 455                 460

Ala Thr Leu Gly Gly Phe Gly Ser Leu Gly Leu Asp Cys Glu Pro Arg
465                 470                 475                 480

Thr Gly Leu Asp Phe Ser Asp Leu Tyr Tyr Leu Thr Met Asn Asn Lys
                485                 490                 495

His Trp Leu Val His Lys Glu Trp Phe His Asp Ile Pro Leu Pro Trp
            500                 505                 510
```

His Ala Gly Ala Asp Thr Gly Thr Pro His Trp Asn Asn Lys Glu Ala
    515                 520                 525

Leu Val Glu Phe Lys Asp Ala His Ala Lys Arg Gln Thr Val Val
    530                 535                 540

Leu Gly Ser Gln Glu Gly Ala Val His Thr Ala Leu Ala Gly Ala Leu
545                 550                 555                 560

Glu Ala Glu Met Asp Gly Ala Lys Gly Arg Leu Ser Ser Gly His Leu
                565                 570                 575

Lys Cys Arg Leu Lys Met Asp Lys Leu Arg Leu Lys Gly Val Ser Tyr
                580                 585                 590

Ser Leu Cys Thr Ala Ala Phe Thr Phe Thr Lys Ile Pro Ala Glu Thr
            595                 600                 605

Leu His Gly Thr Val Thr Val Glu Val Gln Tyr Ala Gly Thr Asp Gly
    610                 615                 620

Pro Cys Lys Val Pro Ala Gln Met Ala Val Asp Met Gln Thr Leu Thr
625                 630                 635                 640

Pro Val Gly Arg Leu Ile Thr Ala Asn Pro Val Ile Thr Glu Ser Thr
                645                 650                 655

Glu Asn Ser Lys Met Met Leu Glu Leu Asp Pro Pro Phe Gly Asp Ser
                660                 665                 670

Tyr Ile Val Ile Gly Val Gly Glu Lys Lys Ile Thr His His Trp His
            675                 680                 685

Arg Ser Gly Ser Thr Ile Gly Lys Ala Phe Glu Ala Thr Val Arg Gly
    690                 695                 700

Ala Lys Arg Met Ala Val Leu Gly Asp Thr Ala Trp Asp Phe Gly Ser
705                 710                 715                 720

Val Gly Gly Ala Leu Asn Ser Leu Gly Lys Gly Ile His Gln Ile Phe
                725                 730                 735

Gly Ala Ala Phe Lys Leu Leu Phe Gly Gly Met Ser Trp Phe Ser Gln
            740                 745                 750

Ile Leu Ile Gly Thr Leu Leu Val Trp Leu Gly Leu Asn Thr Lys Asn
    755                 760                 765

Gly Ser Ile Ser Leu Thr Cys Leu Ala Leu Gly Gly Val Leu Ile Phe
770                 775                 780

Leu Ser Thr Ala Val Ser Ala Gly Ala Asp Gln Gly Cys Ala Ile Asn
785                 790                 795                 800

Phe Gly Lys Arg Glu Leu Lys Cys Gly Asp Gly Ile Phe Ile Phe Arg
                805                 810                 815

Asp Ser Asp Asp Trp Leu Asn Lys Tyr Ser Tyr Tyr Pro Glu Asp Pro
            820                 825                 830

Val Lys Leu Ala Ser Ile Val Lys Ala Ser Phe Glu Glu Gly Lys Cys
    835                 840                 845

Gly Leu Asn Ser Val Asp Ser Leu Glu His Glu Met Trp Arg Ser Arg
850                 855                 860

Ala Asp Glu Ile Asn Ala Ile Phe Glu Glu Asn Glu Val Asp Ile Ser
865                 870                 875                 880

Val Val Val Gln Asp Pro Lys Asn Val Tyr Gln Arg Gly Thr His Pro
                885                 890                 895

Phe Ser Arg Ile Arg Asp Gly Leu Gln Tyr Gly Trp Lys Thr Trp Gly
            900                 905                 910

Lys Asn Leu Val Phe Ser Pro Gly Arg Lys Asn Gly Ser Phe Ile Ile
    915                 920                 925

```
Asp Gly Lys Ser Arg Lys Glu Cys Pro Phe Ser Asn Arg Val Trp Asn
    930             935             940

Ser Phe Gln Ile Glu Glu Phe Gly Thr Gly Val Phe Thr Thr Arg Val
945             950             955             960

Tyr Met Asp Ala Val Phe Glu Tyr Thr Ile Asp Cys Asp Gly Ser Ile
                965             970             975

Leu Gly Ala Ala Val Asn Gly Lys Lys Ser Ala His Gly Ser Pro Thr
            980             985             990

Phe Trp Met Gly Ser His Glu Val Asn Gly Thr Trp Met Ile His Thr
        995             1000            1005

Leu Glu Ala Leu Asp Tyr Lys Glu Cys Glu Trp Pro Leu Thr His
    1010            1015            1020

Thr Ile Gly Thr Ser Val Glu Glu Ser Glu Met Phe Met Pro Arg
    1025            1030            1035

Ser Ile Gly Gly Pro Val Ser Ser His Asn His Ile Pro Gly Tyr
    1040            1045            1050

Lys Val Gln Thr Asn Gly Pro Trp Met Gln Val Pro Leu Glu Val
    1055            1060            1065

Lys Arg Glu Ala Cys Pro Gly Thr Ser Val Ile Ile Asp Gly Asn
    1070            1075            1080

Cys Asp Gly Arg Gly Lys Ser Thr Arg Ser Thr Thr Asp Ser Gly
    1085            1090            1095

Lys Val Ile Pro Glu Trp Cys Cys Arg Ser Cys Thr Met Pro Pro
    1100            1105            1110

Val Ser Phe His Gly Ser Asp Gly Cys Trp Tyr Pro Met Glu Ile
    1115            1120            1125

Arg Pro Arg Lys Thr His Glu Ser His Leu Val Arg Ser Trp Val
    1130            1135            1140

Thr Ala Gly Glu Ile His Ala Val Pro Phe Gly Leu Val Ser Met
    1145            1150            1155

Met Ile Ala Met Glu Val Val Leu Arg Lys Arg Gln Gly Pro Lys
    1160            1165            1170

Gln Met Leu Val Gly Gly Val Val Leu Leu Gly Ala Met Leu Val
    1175            1180            1185

Gly Gln Val Thr Leu Leu Asp Leu Leu Lys Leu Thr Val Ala Val
    1190            1195            1200

Gly Leu His Phe His Glu Met Asn Asn Gly Gly Asp Ala Met Tyr
    1205            1210            1215

Met Ala Leu Ile Ala Ala Phe Ser Ile Arg Pro Gly Leu Leu Ile
    1220            1225            1230

Gly Phe Gly Leu Arg Thr Leu Trp Ser Pro Arg Glu Arg Leu Val
    1235            1240            1245

Leu Thr Leu Gly Ala Ala Met Val Glu Ile Ala Leu Gly Gly Val
    1250            1255            1260

Met Gly Gly Leu Trp Lys Tyr Leu Asn Ala Val Ser Leu Cys Ile
    1265            1270            1275

Leu Thr Ile Asn Ala Val Ala Ser Arg Lys Ala Ser Asn Thr Ile
    1280            1285            1290

Leu Pro Leu Met Ala Leu Leu Thr Pro Val Thr Met Ala Glu Val
    1295            1300            1305

Arg Leu Ala Ala Met Phe Phe Cys Ala Met Val Ile Ile Gly Val
    1310            1315            1320

Leu His Gln Asn Phe Lys Asp Thr Ser Met Gln Lys Thr Ile Pro
```

```
            1325                1330                1335

Leu Val Ala Leu Thr Leu Thr Ser Tyr Leu Gly Leu Thr Gln Pro
            1340                1345                1350

Phe Leu Gly Leu Cys Ala Phe Leu Ala Thr Arg Ile Phe Gly Arg
            1355                1360                1365

Arg Ser Ile Pro Val Asn Glu Ala Leu Ala Ala Ala Gly Leu Val
            1370                1375                1380

Gly Val Leu Ala Gly Leu Ala Phe Gln Glu Met Glu Asn Phe Leu
            1385                1390                1395

Gly Pro Ile Ala Val Gly Gly Leu Leu Met Met Leu Val Ser Val
            1400                1405                1410

Ala Gly Arg Val Asp Gly Leu Glu Leu Lys Lys Leu Gly Glu Val
            1415                1420                1425

Ser Trp Glu Glu Glu Ala Glu Ile Ser Gly Ser Ser Ala Arg Tyr
            1430                1435                1440

Asp Val Ala Leu Ser Glu Gln Gly Glu Phe Lys Leu Leu Ser Glu
            1445                1450                1455

Glu Lys Val Pro Trp Asp Gln Val Val Met Thr Ser Leu Ala Leu
            1460                1465                1470

Val Gly Ala Ala Leu His Pro Phe Ala Leu Leu Leu Val Leu Ala
            1475                1480                1485

Gly Trp Leu Phe His Val Arg Gly Ala Arg Arg Ser Gly Asp Val
            1490                1495                1500

Leu Trp Asp Ile Pro Thr Pro Lys Ile Ile Glu Glu Cys Glu His
            1505                1510                1515

Leu Glu Asp Gly Ile Tyr Gly Ile Phe Gln Ser Thr Phe Leu Gly
            1520                1525                1530

Ala Ser Gln Arg Gly Val Gly Val Ala Gln Gly Gly Val Phe His
            1535                1540                1545

Thr Met Trp His Val Thr Arg Gly Ala Phe Leu Val Arg Asn Gly
            1550                1555                1560

Lys Lys Leu Ile Pro Ser Trp Ala Ser Val Lys Glu Asp Leu Val
            1565                1570                1575

Ala Tyr Gly Gly Ser Trp Lys Leu Glu Gly Arg Trp Asp Gly Glu
            1580                1585                1590

Glu Glu Val Gln Leu Ile Ala Ala Val Pro Gly Lys Asn Val Val
            1595                1600                1605

Asn Val Gln Thr Lys Pro Ser Leu Phe Lys Val Arg Asn Gly Gly
            1610                1615                1620

Glu Ile Gly Ala Val Ala Leu Asp Tyr Pro Ser Gly Thr Ser Gly
            1625                1630                1635

Ser Pro Ile Val Asn Arg Asn Gly Glu Val Ile Gly Leu Tyr Gly
            1640                1645                1650

Asn Gly Ile Leu Val Gly Asp Asn Ser Phe Val Ser Ala Ile Ser
            1655                1660                1665

Gln Thr Glu Val Lys Glu Glu Gly Lys Glu Glu Leu Gln Glu Ile
            1670                1675                1680

Pro Thr Met Leu Lys Lys Gly Met Thr Thr Val Leu Asp Phe His
            1685                1690                1695

Pro Gly Ala Gly Lys Thr Arg Arg Phe Leu Pro Gln Ile Leu Ala
            1700                1705                1710

Glu Cys Ala Arg Arg Arg Leu Arg Thr Leu Val Leu Ala Pro Thr
            1715                1720                1725
```

-continued

Arg Val Val Leu Ser Glu Met Lys Glu Ala Phe His Gly Leu Asp
    1730                1735                1740

Val Lys Phe His Thr Gln Ala Phe Ser Ala His Gly Ser Gly Arg
    1745                1750                1755

Glu Val Ile Asp Ala Met Cys His Ala Thr Leu Thr Tyr Arg Met
    1760                1765                1770

Leu Glu Pro Thr Arg Val Val Asn Trp Glu Val Ile Ile Met Asp
    1775                1780                1785

Glu Ala His Phe Leu Asp Pro Ala Ser Ile Ala Ala Arg Gly Trp
    1790                1795                1800

Ala Ala His Arg Ala Arg Ala Asn Glu Ser Ala Thr Ile Leu Met
    1805                1810                1815

Thr Ala Thr Pro Pro Gly Thr Ser Asp Glu Phe Pro His Ser Asn
    1820                1825                1830

Gly Glu Ile Glu Asp Val Gln Thr Asp Ile Pro Ser Glu Pro Trp
    1835                1840                1845

Asn Thr Gly His Asp Trp Ile Leu Ala Asp Lys Arg Pro Thr Ala
    1850                1855                1860

Trp Phe Leu Pro Ser Ile Arg Ala Ala Asn Val Met Ala Ala Ser
    1865                1870                1875

Leu Arg Lys Ala Gly Lys Ser Val Val Val Leu Asn Arg Lys Thr
    1880                1885                1890

Phe Glu Arg Glu Tyr Pro Thr Ile Lys Gln Lys Lys Pro Asp Phe
    1895                1900                1905

Ile Leu Ala Thr Asp Ile Ala Glu Met Gly Ala Asn Leu Cys Val
    1910                1915                1920

Glu Arg Val Leu Asp Cys Arg Thr Ala Phe Lys Pro Val Leu Val
    1925                1930                1935

Asp Glu Gly Arg Lys Val Ala Ile Lys Gly Pro Leu Arg Ile Ser
    1940                1945                1950

Ala Ser Ser Ala Ala Gln Arg Arg Gly Arg Ile Gly Arg Asn Pro
    1955                1960                1965

Asn Arg Asp Gly Asp Ser Tyr Tyr Tyr Ser Glu Pro Thr Ser Glu
    1970                1975                1980

Asn Asn Ala His His Val Cys Trp Leu Glu Ala Ser Met Leu Leu
    1985                1990                1995

Asp Asn Met Glu Val Arg Gly Gly Met Val Ala Pro Leu Tyr Gly
    2000                2005                2010

Val Glu Gly Thr Lys Thr Pro Val Ser Pro Gly Glu Met Arg Leu
    2015                2020                2025

Arg Asp Asp Gln Arg Lys Val Phe Arg Glu Leu Val Arg Asn Cys
    2030                2035                2040

Asp Leu Pro Val Trp Leu Ser Trp Gln Val Ala Lys Ala Gly Leu
    2045                2050                2055

Lys Thr Asn Asp Arg Lys Trp Cys Phe Glu Gly Pro Glu Glu His
    2060                2065                2070

Glu Ile Leu Asn Asp Ser Gly Glu Thr Val Lys Cys Arg Ala Pro
    2075                2080                2085

Gly Gly Ala Lys Lys Pro Leu Arg Pro Arg Trp Cys Asp Glu Arg
    2090                2095                2100

Val Ser Ser Asp Gln Ser Ala Leu Ser Glu Phe Ile Lys Phe Ala
    2105                2110                2115

```
Glu Gly Arg Arg Gly Ala Ala Glu Val Leu Val Leu Ser Glu
    2120            2125            2130

Leu Pro Asp Phe Leu Ala Lys Lys Gly Glu Ala Met Asp Thr
    2135            2140            2145

Ile Ser Val Phe Leu His Ser Glu Glu Gly Ser Arg Ala Tyr Arg
    2150            2155            2160

Asn Ala Leu Ser Met Met Pro Glu Ala Met Thr Ile Val Met Leu
    2165            2170            2175

Phe Ile Leu Ala Gly Leu Leu Thr Ser Gly Met Val Ile Phe Phe
    2180            2185            2190

Met Ser Pro Lys Gly Ile Ser Arg Met Ser Met Ala Met Gly Thr
    2195            2200            2205

Met Ala Gly Cys Gly Tyr Leu Met Phe Leu Gly Gly Val Lys Pro
    2210            2215            2220

Thr His Ile Ser Tyr Val Met Leu Ile Phe Phe Val Leu Met Val
    2225            2230            2235

Val Val Ile Pro Glu Pro Gly Gln Gln Arg Ser Ile Gln Asp Asn
    2240            2245            2250

Gln Val Ala Tyr Leu Ile Ile Gly Ile Leu Thr Leu Val Ser Ala
    2255            2260            2265

Val Ala Ala Asn Glu Leu Gly Met Leu Glu Lys Thr Lys Glu Asp
    2270            2275            2280

Leu Phe Gly Lys Lys Asn Leu Ile Pro Ser Ser Ala Ser Pro Trp
    2285            2290            2295

Ser Trp Pro Asp Leu Asp Leu Lys Pro Gly Ala Ala Trp Thr Val
    2300            2305            2310

Tyr Val Gly Ile Val Thr Met Leu Ser Pro Met Leu His His Trp
    2315            2320            2325

Ile Lys Val Glu Tyr Gly Asn Leu Ser Leu Ser Gly Ile Ala Gln
    2330            2335            2340

Ser Ala Ser Val Leu Ser Phe Met Asp Lys Gly Ile Pro Phe Met
    2345            2350            2355

Lys Met Asn Ile Ser Val Ile Met Leu Leu Val Ser Gly Trp Asn
    2360            2365            2370

Ser Ile Thr Val Met Pro Leu Leu Cys Gly Ile Gly Cys Ala Met
    2375            2380            2385

Leu His Trp Ser Leu Ile Leu Pro Gly Ile Lys Ala Gln Gln Ser
    2390            2395            2400

Lys Leu Ala Gln Arg Arg Val Phe His Gly Val Ala Lys Asn Pro
    2405            2410            2415

Val Val Asp Gly Asn Pro Thr Val Asp Ile Glu Glu Ala Pro Glu
    2420            2425            2430

Met Pro Ala Leu Tyr Glu Lys Lys Leu Ala Leu Tyr Leu Leu Leu
    2435            2440            2445

Ala Leu Ser Leu Ala Ser Val Ala Met Cys Arg Thr Pro Phe Ser
    2450            2455            2460

Leu Ala Glu Gly Ile Val Leu Ala Ser Ala Ala Leu Gly Pro Leu
    2465            2470            2475

Ile Glu Gly Asn Thr Ser Leu Leu Trp Asn Gly Pro Met Ala Val
    2480            2485            2490

Ser Met Thr Gly Val Met Arg Gly Asn His Tyr Ala Phe Val Gly
    2495            2500            2505

Val Met Tyr Asn Leu Trp Lys Met Lys Thr Gly Arg Arg Gly Ser
```

```
                    2510                2515                2520
Ala Asn Gly Lys Thr Leu Gly Glu Val Trp Lys Arg Glu Leu Asn
    2525                2530                2535
Leu Leu Asp Lys Arg Gln Phe Glu Leu Tyr Lys Arg Thr Asp Ile
    2540                2545                2550
Val Glu Val Asp Arg Asp Thr Ala Arg Arg His Leu Ala Glu Gly
    2555                2560                2565
Lys Val Asp Thr Gly Val Ala Val Ser Arg Gly Thr Ala Lys Leu
    2570                2575                2580
Arg Trp Phe His Glu Arg Gly Tyr Val Lys Leu Glu Gly Arg Val
    2585                2590                2595
Ile Asp Leu Gly Cys Gly Arg Gly Gly Trp Cys Tyr Tyr Ala Ala
    2600                2605                2610
Ala Gln Lys Glu Val Ser Gly Val Lys Gly Phe Thr Leu Gly Arg
    2615                2620                2625
Asp Gly His Glu Lys Pro Met Asn Val Gln Ser Leu Gly Trp Asn
    2630                2635                2640
Ile Ile Thr Phe Lys Asp Lys Thr Asp Ile His Arg Leu Glu Pro
    2645                2650                2655
Val Lys Cys Asp Thr Leu Leu Cys Asp Ile Gly Glu Ser Ser Ser
    2660                2665                2670
Ser Ser Val Thr Glu Gly Glu Arg Thr Val Arg Val Leu Asp Thr
    2675                2680                2685
Val Glu Lys Trp Leu Ala Cys Gly Val Asp Asn Phe Cys Val Lys
    2690                2695                2700
Val Leu Ala Pro Tyr Met Pro Asp Val Leu Glu Lys Leu Glu Leu
    2705                2710                2715
Leu Gln Arg Arg Phe Gly Gly Thr Val Ile Arg Asn Pro Leu Ser
    2720                2725                2730
Arg Asn Ser Thr His Glu Met Tyr Tyr Val Ser Gly Ala Arg Ser
    2735                2740                2745
Asn Val Thr Phe Thr Val Asn Gln Thr Ser Arg Leu Leu Met Arg
    2750                2755                2760
Arg Met Arg Arg Pro Thr Gly Lys Val Thr Leu Glu Ala Asp Val
    2765                2770                2775
Ile Leu Pro Ile Gly Thr Arg Ser Val Glu Thr Asp Lys Gly Pro
    2780                2785                2790
Leu Asp Lys Glu Ala Ile Glu Glu Arg Val Glu Arg Ile Lys Ser
    2795                2800                2805
Glu Tyr Met Thr Ser Trp Phe Tyr Asp Asn Asp Asn Pro Tyr Arg
    2810                2815                2820
Thr Trp His Tyr Cys Gly Ser Tyr Val Thr Lys Thr Ser Gly Ser
    2825                2830                2835
Ala Ala Ser Met Val Asn Gly Val Ile Lys Ile Leu Thr Tyr Pro
    2840                2845                2850
Trp Asp Arg Ile Glu Glu Val Thr Arg Met Ala Met Thr Asp Thr
    2855                2860                2865
Thr Pro Phe Gly Gln Gln Arg Val Phe Lys Glu Lys Val Asp Thr
    2870                2875                2880
Arg Ala Lys Asp Pro Pro Ala Gly Thr Arg Lys Ile Met Lys Val
    2885                2890                2895
Val Asn Arg Trp Leu Phe Arg His Leu Ala Arg Glu Lys Asn Pro
    2900                2905                2910
```

-continued

```
Arg Leu Cys Thr Lys Glu Glu Phe Ile Ala Lys Val Arg Ser His
2915                2920                2925

Ala Ala Ile Gly Ala Tyr Leu Glu Glu Gln Glu Gln Trp Lys Thr
2930                2935                2940

Ala Asn Glu Ala Val Gln Asp Pro Lys Phe Trp Glu Leu Val Asp
2945                2950                2955

Glu Glu Arg Lys Leu His Gln Gln Gly Arg Cys Arg Thr Cys Val
2960                2965                2970

Tyr Asn Met Met Gly Lys Arg Glu Lys Lys Leu Ser Glu Phe Gly
2975                2980                2985

Lys Ala Lys Gly Ser Arg Ala Ile Trp Tyr Met Trp Leu Gly Ala
2990                2995                3000

Arg Tyr Leu Glu Phe Glu Ala Leu Gly Phe Leu Asn Glu Asp His
3005                3010                3015

Trp Ala Ser Arg Glu Asn Ser Gly Gly Gly Val Glu Gly Ile Gly
3020                3025                3030

Leu Gln Tyr Leu Gly Tyr Val Ile Arg Asp Leu Ala Ala Met Asp
3035                3040                3045

Gly Gly Gly Phe Tyr Ala Asp Asp Thr Ala Gly Trp Asp Thr Arg
3050                3055                3060

Ile Thr Glu Ala Asp Leu Asp Asp Glu Gln Glu Ile Leu Asn Tyr
3065                3070                3075

Met Ser Pro His His Lys Lys Leu Ala Gln Ala Val Met Glu Met
3080                3085                3090

Thr Tyr Lys Asn Lys Val Val Lys Val Leu Arg Pro Ala Pro Gly
3095                3100                3105

Gly Lys Ala Tyr Met Asp Val Ile Ser Arg Arg Asp Gln Arg Gly
3110                3115                3120

Ser Gly Gln Val Val Thr Tyr Ala Leu Asn Thr Ile Thr Asn Leu
3125                3130                3135

Lys Val Gln Leu Ile Arg Met Ala Glu Ala Glu Met Val Ile His
3140                3145                3150

His Gln His Val Gln Asp Cys Asp Glu Ser Val Leu Thr Arg Leu
3155                3160                3165

Glu Ala Trp Leu Thr Glu His Gly Cys Asp Arg Leu Lys Arg Met
3170                3175                3180

Ala Val Ser Gly Asp Asp Cys Val Val Arg Pro Ile Asp Asp Arg
3185                3190                3195

Phe Gly Leu Ala Leu Ser His Leu Asn Ala Met Ser Lys Val Arg
3200                3205                3210

Lys Asp Ile Ser Glu Trp Gln Pro Ser Lys Gly Trp Asn Asp Trp
3215                3220                3225

Glu Asn Val Pro Phe Cys Ser His His Phe His Glu Leu Gln Leu
3230                3235                3240

Lys Asp Gly Arg Arg Ile Val Val Pro Cys Arg Glu Gln Asp Glu
3245                3250                3255

Leu Ile Gly Arg Gly Arg Val Ser Pro Gly Asn Gly Trp Met Ile
3260                3265                3270

Lys Glu Thr Ala Cys Leu Ser Lys Ala Tyr Ala Asn Met Trp Ser
3275                3280                3285

Leu Met Tyr Phe His Lys Arg Asp Met Arg Leu Leu Ser Leu Ala
3290                3295                3300
```

```
Val Ser  Ser Ala Val Pro  Thr Ser Trp Val Pro  Gln Gly Arg Thr
    3305             3310              3315

Thr Trp  Ser Ile His Gly  Lys Gly Glu Trp Met  Thr Thr Glu Asp
    3320             3325              3330

Met Leu  Glu Val Trp Asn  Arg Val Trp Ile Thr  Asn Asn Pro His
    3335             3340              3345

Met Gln  Asp Lys Thr Met  Val Lys Lys Trp Arg  Asp Val Pro Tyr
    3350             3355              3360

Leu Thr  Lys Arg Gln Asp  Lys Leu Cys Gly Ser  Leu Ile Gly Met
    3365             3370              3375

Thr Asn  Arg Ala Thr Trp  Ala Ser His Ile His  Leu Val Ile His
    3380             3385              3390

Arg Ile  Arg Thr Leu Ile  Gly Gln Glu Lys Tyr  Thr Asp Tyr Leu
    3395             3400              3405

Thr Val  Met Asp Arg Tyr  Ser Val Asp Ala Asp  Leu Gln Leu Gly
    3410             3415              3420

Glu Leu  Ile
    3425
```

<210> SEQ ID NO 3
<211> LENGTH: 20
<212> TYPE: PRT
<213> ORGANISM: Artificial Sequence
<220> FEATURE:
<223> OTHER INFORMATION: Junction of Yellow Fever and Zika virus
      sequence

<400> SEQUENCE: 3

```
Met Arg Gly Leu Ser Ser Arg Lys Arg Arg Gly Thr Asp Thr Ser Val
1               5                   10                  15

Gly Ile Val Gly
            20
```

<210> SEQ ID NO 4
<211> LENGTH: 18
<212> TYPE: PRT
<213> ORGANISM: Artificial Sequence
<220> FEATURE:
<223> OTHER INFORMATION: Zika virus signal sequence

<400> SEQUENCE: 4

```
Gly Thr Asp Thr Ser Val Gly Ile Val Gly Leu Leu Leu Thr Thr Ala
1               5                   10                  15

Met Ala
```

<210> SEQ ID NO 5
<211> LENGTH: 690
<212> TYPE: PRT
<213> ORGANISM: Artificial Sequence
<220> FEATURE:
<223> OTHER INFORMATION: Zika signal sequence and prME gene

<400> SEQUENCE: 5

```
Gly Thr Asp Thr Ser Val Gly Ile Val Gly Leu Leu Leu Thr Thr Ala
1               5                   10                  15

Met Ala Val Glu Val Thr Arg Arg Gly Ser Ala Tyr Tyr Met Tyr Leu
            20                  25                  30

Asp Arg Ser Asp Ala Gly Glu Ala Ile Ser Phe Pro Thr Thr Leu Gly
        35                  40                  45

Met Asn Lys Cys Tyr Ile Gln Ile Met Asp Leu Gly His Met Cys Asp
```

```
            50                  55                  60
Ala Thr Met Ser Tyr Glu Cys Pro Met Leu Asp Glu Gly Val Glu Pro
 65                  70                  75                  80

Asp Asp Val Asp Cys Trp Cys Asn Thr Thr Ser Thr Trp Val Val Tyr
                 85                  90                  95

Gly Thr Cys His His Lys Lys Gly Glu Ala Arg Arg Ser Arg Arg Ala
                100                 105                 110

Val Thr Leu Pro Ser His Ser Thr Arg Lys Leu Gln Thr Arg Ser Gln
                115                 120                 125

Thr Trp Leu Glu Ser Arg Glu Tyr Thr Lys His Leu Ile Arg Val Glu
130                 135                 140

Asn Trp Ile Phe Arg Asn Pro Gly Phe Ala Leu Ala Ala Ala Ala Ile
145                 150                 155                 160

Ala Trp Leu Leu Gly Ser Ser Thr Ser Gln Lys Val Ile Tyr Leu Val
                165                 170                 175

Met Ile Leu Leu Ile Ala Pro Ala Tyr Ser Ile Arg Cys Ile Gly Val
                180                 185                 190

Ser Asn Arg Asp Phe Val Glu Gly Met Ser Gly Gly Thr Trp Val Asp
            195                 200                 205

Val Val Leu Glu His Gly Gly Cys Val Thr Val Met Ala Gln Asp Lys
            210                 215                 220

Pro Thr Val Asp Ile Glu Leu Val Thr Thr Thr Val Ser Asn Met Ala
225                 230                 235                 240

Glu Val Arg Ser Tyr Cys Tyr Glu Ala Ser Ile Ser Asp Met Ala Ser
                245                 250                 255

Asp Ser Arg Cys Pro Thr Gln Gly Glu Ala Tyr Leu Asp Lys Gln Ser
                260                 265                 270

Asp Thr Gln Tyr Val Cys Lys Arg Thr Leu Val Asp Arg Gly Trp Gly
                275                 280                 285

Asn Gly Cys Gly Leu Phe Gly Lys Gly Ser Leu Val Thr Cys Ala Lys
            290                 295                 300

Phe Ala Cys Ser Lys Lys Met Thr Gly Lys Ser Ile Gln Pro Glu Asn
305                 310                 315                 320

Leu Glu Tyr Arg Ile Met Leu Ser Val His Gly Ser Gln His Ser Gly
                325                 330                 335

Met Ile Val Asn Asp Thr Gly His Glu Thr Asp Glu Asn Arg Ala Lys
                340                 345                 350

Val Glu Ile Thr Pro Asn Ser Pro Arg Ala Glu Ala Thr Leu Gly Gly
                355                 360                 365

Phe Gly Ser Leu Gly Leu Asp Cys Glu Pro Arg Thr Gly Leu Asp Phe
370                 375                 380

Ser Asp Leu Tyr Tyr Leu Thr Met Asn Asn Lys His Trp Leu Val His
385                 390                 395                 400

Lys Glu Trp Phe His Asp Ile Pro Leu Pro Trp His Ala Gly Ala Asp
                405                 410                 415

Thr Gly Thr Pro His Trp Asn Asn Lys Glu Ala Leu Val Glu Phe Lys
                420                 425                 430

Asp Ala His Ala Lys Arg Gln Thr Val Val Leu Gly Ser Gln Glu
                435                 440                 445

Gly Ala Val His Thr Ala Leu Ala Gly Ala Leu Glu Ala Glu Met Asp
                450                 455                 460

Gly Ala Lys Gly Arg Leu Ser Ser Gly His Leu Lys Cys Arg Leu Lys
465                 470                 475                 480
```

```
Met Asp Lys Leu Arg Leu Lys Gly Val Ser Tyr Ser Leu Cys Thr Ala
                485                 490                 495

Ala Phe Thr Phe Thr Lys Ile Pro Ala Glu Thr Leu His Gly Thr Val
            500                 505                 510

Thr Val Glu Val Gln Tyr Ala Gly Thr Asp Gly Pro Cys Lys Val Pro
        515                 520                 525

Ala Gln Met Ala Val Asp Met Gln Thr Leu Thr Pro Val Gly Arg Leu
    530                 535                 540

Ile Thr Ala Asn Pro Val Ile Thr Glu Ser Thr Glu Asn Ser Lys Met
545                 550                 555                 560

Met Leu Glu Leu Asp Pro Pro Phe Gly Asp Ser Tyr Ile Val Ile Gly
                565                 570                 575

Val Gly Glu Lys Lys Ile Thr His His Trp His Arg Ser Gly Ser Thr
            580                 585                 590

Ile Gly Lys Ala Phe Glu Ala Thr Val Arg Gly Ala Lys Arg Met Ala
        595                 600                 605

Val Leu Gly Asp Thr Ala Trp Asp Phe Gly Ser Val Gly Gly Ala Leu
    610                 615                 620

Asn Ser Leu Gly Lys Gly Ile His Gln Ile Phe Gly Ala Ala Phe Lys
625                 630                 635                 640

Leu Leu Phe Gly Gly Met Ser Trp Phe Ser Gln Ile Leu Ile Gly Thr
                645                 650                 655

Leu Leu Val Trp Leu Gly Leu Asn Thr Lys Asn Gly Ser Ile Ser Leu
            660                 665                 670

Thr Cys Leu Ala Leu Gly Gly Val Leu Ile Phe Leu Ser Thr Ala Val
        675                 680                 685

Ser Ala
    690

<210> SEQ ID NO 6
<211> LENGTH: 21
<212> TYPE: PRT
<213> ORGANISM: Artificial Sequence
<220> FEATURE:
<223> OTHER INFORMATION: Zika E protein fragment

<400> SEQUENCE: 6

Ile His Gln Ile Phe Gly Ala Ala Phe Lys Leu Leu Phe Gly Gly Met
1               5                   10                  15

Ser Trp Phe Ser Gln
            20

<210> SEQ ID NO 7
<211> LENGTH: 21
<212> TYPE: PRT
<213> ORGANISM: Artificial Sequence
<220> FEATURE:
<223> OTHER INFORMATION: Zika E protein fragment

<400> SEQUENCE: 7

Cys Val Thr Val Met Ala Gln Asp Lys Pro Thr Val Asp Ile Glu Leu
1               5                   10                  15

Val Thr Thr Thr Val
            20

<210> SEQ ID NO 8
<211> LENGTH: 60
<212> TYPE: DNA
```

-continued

```
<213> ORGANISM: Artificial Sequence
<220> FEATURE:
<223> OTHER INFORMATION: pcr primer

<400> SEQUENCE: 8
gttgtggaaa atgctggacc caagacaagg cttggctgtt ctaaggaaag tcaagagagt    60

<210> SEQ ID NO 9
<211> LENGTH: 60
<212> TYPE: DNA
<213> ORGANISM: Artificial Sequence
<220> FEATURE:
<223> OTHER INFORMATION: pcr primer

<400> SEQUENCE: 9
tctaaatatg aagataccat ctccgcactt gagctctctc ttgccaaagt tgatggcgca    60

<210> SEQ ID NO 10
<211> LENGTH: 27
<212> TYPE: PRT
<213> ORGANISM: Artificial Sequence
<220> FEATURE:
<223> OTHER INFORMATION: YVF - ZIKA chimer

<400> SEQUENCE: 10

Leu Ser Ser Arg Lys Arg Arg Ser His Asp Val Leu Thr Val Gln Phe
 1               5                  10                  15

Leu Ile Leu Gly Met Leu Leu Met Thr Gly Gly
            20                  25

<210> SEQ ID NO 11
<211> LENGTH: 29
<212> TYPE: PRT
<213> ORGANISM: Artificial Sequence
<220> FEATURE:
<223> OTHER INFORMATION: YFV - Zika chimer

<400> SEQUENCE: 11

Gly Arg Lys Gln Asn Lys Arg Gly Gly Asn Glu Gly Ser Ile Met Trp
 1               5                  10                  15

Leu Ala Ser Leu Ala Val Val Ile Ala Cys Ala Gly Ala
            20                  25

<210> SEQ ID NO 12
<211> LENGTH: 25
<212> TYPE: PRT
<213> ORGANISM: Artificial Sequence
<220> FEATURE:
<223> OTHER INFORMATION: YFV-Zika Chimer

<400> SEQUENCE: 12

Arg Lys Glu Lys Lys Arg Gly Thr Asp Thr Ser Val Gly Ile Val
 1               5                  10                  15

Gly Leu Leu Leu Thr Thr Ala Met Ala
            20                  25

<210> SEQ ID NO 13
<211> LENGTH: 27
<212> TYPE: PRT
<213> ORGANISM: Artificial Sequence
<220> FEATURE:
<223> OTHER INFORMATION: YFV - Zika Chimer

<400> SEQUENCE: 13

Leu Ser Ser Arg Lys Arg Arg Ser His Asp Val Leu Thr Val Gln Phe
```

```
1               5                  10                 15
Leu Ile Leu Gly Met Leu Leu Met Thr Gly Gly
            20                25
```

<210> SEQ ID NO 14
<211> LENGTH: 19
<212> TYPE: PRT
<213> ORGANISM: Artificial Sequence
<220> FEATURE:
<223> OTHER INFORMATION: YFV-Zika chimer

<400> SEQUENCE: 14

```
Leu Ser Ser Arg Lys Arg Arg Ser His Asp Val Leu Thr Val Gln Phe
1               5                  10                 15

Leu Ile Leu
```

<210> SEQ ID NO 15
<211> LENGTH: 25
<212> TYPE: PRT
<213> ORGANISM: Artificial Sequence
<220> FEATURE:
<223> OTHER INFORMATION: YFV - Zika chimer

<400> SEQUENCE: 15

```
Leu Ser Ser Arg Lys Arg Arg Gly Thr Asp Thr Ser Val Gly Ile Val
1               5                  10                 15

Gly Leu Leu Leu Thr Thr Ala Met Ala
            20                25
```

CHIMERIC YELLOW FEVER ZIKA VIRUS STRAIN

The recent outbreak of ZIKA in the Americas has led to the search of therapeutics to curb or prevent the debilitating disease. As of now, a number of antivirals and vaccine candidates have been reported that show activity against the ZIKA virus (ZIKV) but none has been approved yet even during an emergency. The yellow fever (YF) and ZIKA viruses belong to a genus called *Flavivirus* together with the Dengue, Japanese encephalitis, West Nile, Tick borne encephalitis viruses.

Vaccines against *flaviviruses* have been developed, such as the well-established attenuated YF17D yellow fever vaccine.

Furthermore chimeric vaccines have been developed wherein the prM/E genes of one *flavivirus* are inserted, or replaced, in the prM/E genes of another *flavivirus*. The best known examples hereof are the Chimerivax viruses (Guirakhoo et al. (1999) *Virology* 257, 363-372).

It has been found that the C terminal part of the C protein acts a signal peptide and it important in the proper proteolytic processing of the viral proteins. To what extent a chimeric construct should contain the signal sequence of the parent virus or from the insert is unpredictable, since optimal processing and viral fitness are not correlated (see Lee et al. (2000) *J. Virol.* 74, 24-32 and Lobigs & Lee (2004) *J. Virol.* 78, 178-86).

Xie et al. (2017) mbio 8, e02134-16 discloses chimeric constructs of Dengue virus and Zika virus. The precise mutations that have accumulated during passaging in Vero cells are yet unknown.

SUMMARY OF THE INVENTION

Using the live attenuated YF virus vaccine, YFV 17D, we engineered a chimera by replacing the structural genes of the said virus with those of a ZIKV strain isolated from the Yap Island in 2007 [the sequence is available in GB accession EU545988].

The chimeric virus generated could not be effectively propagated in cell culture begging the need of a protocol to propagate such highly attenuated viruses. Classical approaches of either (a) serial passaging of extracellular recombinant virus particles in tissue culture or (b) rescue of recombinant virus following intracranial inoculation in the brain of mice failed to yield measurable virus progeny (see FIG. 8 panels A+B). As an essential distinction to the art we implemented an essential phase of prolonged passaging of cells that had been transfected with a DNA-based construct expressing said chimeric virus genomes and supported their prolonged replication (see FIG. 8 panel C), prior to serial passaging of extracellular progeny. In an enforced attempt to propagate the virus in cell culture, we developed a protocol that permitted the replication of the virus to high titres of more than $10^3$ plaque forming units (PFU) per mL [or $10^{4.5}$ viral RNA copy numbers/mL], preferably more than $10^5$ PFU/mL [or $10^{6.5}$ viral RNA copy numbers/mL], for use in experimental animal models and vaccine production.

The chimeric virus generated by this method was shown to have acquired the ability to infect naïve Vero cells and propagate the infection without the need of intracellular passaging. Our results show that YF17D-prME-ZIK is replication competent and attenuated and can be used as a vaccine for the prevention of a ZIKV infection.

This invention relates to the use of YF as a vector to generate a chimeric virus in which the pre-Membrane and Envelope (prME) genes including the capsid signal sequence of YF were replaced by those of the heterologous ZIKV.

The present invention shows the generation of a chimeric virus by replacing the structural genes of YF with those of the heterologous ZIKV. By designing a protocol employing initial intracellular passage within cells transfected with cDNA constructs prior to serial passage of extracellular progeny virus that permits the propagation of the rather highly attenuated [as exemplified by no spread of respective mCherry tagged reporter variants thereof, see FIG. 6 panel A] chimeric virus, we could successfully grow the virus to titres of more than $10^3$ PFU/mL or $10^5$ viral RNA copy numbers/mL (see FIG. 10 panel A) by means of (intracellular) passaging in dividing cells. The virus thus generated formed plaques that were markedly smaller than plaques formed by the parental YF17D (see FIG. 10 panel B P1). Following serial passage of extracellular progeny virus plaques diameter increased from passage 1 (P1) to P5 by about to twofold. Also at P5 plaques remained smaller than plaques formed by the parental YF17D suggesting that the virus might be attenuated in vitro. The relative increase in plaque size indicates a gain in replication fitness from P1 to P5.

The invention is further summarized in the following statements:

1. A polynucleotide comprising the sequence of a live, infectious, attenuated Yellow Fever Zika chimeric virus wherein the nucleotide sequence encoding the signal sequence and prME protein of said yellow virus is replaced by a nucleotide sequence encoding the signal sequence and the prME protein of a Zika virus, so that said signal sequence and prME protein of said Zika are expressed, characterised in that the encoded amino acid of the prME protein of a Zika virus differs from the wild type sequence by Ser742Leu substitution as indicated in SEQ ID NO:2. Thus the fragment of the prME protein wherein this mutation (underlined) is located has the sequence IHQIFGAAFKLLFGGMSWFSQ [SEQ ID NO: 6]

2. The polynucleotide which further differs from the wild type sequence by the Ala327Thr substitution as indicated in SEQ ID NO:2.

3. The polynucleotide according to statement 1 or 2, wherein the encoded signal sequence and the prME protein of the Zika virus has the amino acid

[SEQ ID: 5]
GTDTSVGIVGLLLTTAMAVEVTRRGSAYYMYLDRSDAGEAISFPTTLGMNKCYIQIMDLGHMCDA

TMSYECPMLDEGVEPDDVDCWCNTTSTWVVYGTCHHKKGEARRSRRAVTLPSHSTRKLQTRSQ

TWLESREYTKHLIRVENWIFRNPGFALAAAAIAWLLGSSTSQKVIYLVMILLIAPAYSIRCIGVSNR

DFVEGMSGGTWVDVVLEHGGCVTVMAQDKPTVDIELVTTTVSNMAEVRSYCYEASISDMASDS

-continued

```
RCPTQGEAYLDKQSDTQYVCKRTLVDRGWGNGCGLFGKGSLVTCAKFACSKKMTGKSIQPENLE

YRIMLSVHGSQHSGMIVNDTGHETDENRAKVEITPNSPRAEATLGGFGSLGLDCEPRTGLDFSDL

YYLTMNNKHWLVHKEWFHDIPLPWHAGADTGTPHWNNKEALVEFKDAHAKRQTVVVLGSQEGA

VHTALAGALEAEMDGAKGRLSSGHLKCRLKMDKLRLKGVSYSLCTAAFTFTKIPAETLHGTVTVEV

QYAGTDGPCKVPAQMAVDMQTLTPVGRLITANPVITESTENSKMMLELDPPFGDSYIVIGVGEKKI

THHWHRSGSTIGKAFEATVRGAKRMAVLGDTAWDFGSVGGALNSLGKGIHQIFGAAFKLLFGG

MSWFSQILIGTLLVWLGLNTKNGSISLTCLALGGVLIFLSTAVSA.
```

4. The polynucleotide according to any one of statements 1 to 3, wherein the encoded amino acid sequence of the NS2A protein of the yellow fever virus has the Val1318Met substitution as indicated in SEQ ID NO:2,
and/or wherein the encoded amino acid sequence of the NS4B protein of the yellow fever virus has the Glu2416Lys substitution as indicated in SEQ ID NO:2.

5. The polynucleotide according to any one of statements 1 to 4, wherein the yellow virus backboned has, compared with the sequence of YFV 17D, the mutations g4070a, t7333a, g7364a with reference to the nucleotide numbering of SEQ ID NO: 1, thus representing the backbone of the Chimerivax JE construct of Arroyo cited below.

The polynucleotide according to statement any one of statements 1 to 5, which encodes for the amino acid sequence of SEQ ID NO:2, wherein amino acid 327 is Thr. (optionally Ala)

6. The polynucleotide according to any one of statements 1 to 6, comprising the open reading frame of from nucleotide 119 to 10393 depicted in SEQ ID NO:1, stop codon excluded.

7. The polynucleotide according to any one of statements 1 to 7, comprising the sequence depicted in SEQ ID NO:1.

8. A polynucleotide comprising the sequence of a yellow fever virus in which the nucleotide sequence encoding the signal sequence and the prME protein of said yellow virus is replaced by a nucleotide sequence encoding the signal sequence and the prME protein of a Zika virus, so that said signal sequence and prME protein of said Zika is expressed, wherein the nucleotide sequence of the signal peptide of the Zika virus encodes the amino acid sequence GTDTSV-GIVGLLLTTAMA [SEQ ID NO:4].

9. The polynucleotide according to statement 9, wherein the Zika virus is the Yap strain with accession number EU545988.

10. The polynucleotide according to statement 9 or 10, wherein the yellow virus is the YFV 17D attenuated virus.

11. The polynucleotide according to any one of statements 9 to 11, wherein the yellow virus backboned has, compared with the sequence of YFV 17D, the mutations g4070a, t7333a, g7364a with reference to the nucleotide numbering of SEQ ID NO: 1, thus representing the mutations in the backbone of the Chimerivax JE construct of Arroyo cited below.

The polynucleotide according to any one of statements 9 to 12, wherein the Zika virus insert, compared with the sequence of the Zika YAP sequences, has the mutations Ala327Thr and/or Ser742Leu as indicated in SEQ ID NO:2.

12. The polynucleotide according to any one of statements 9 to 13, wherein the sequence at the junction of the C protein of the YF and the signal peptide of the Zika virus encodes the amino acid sequence comprising MRGLSSRKRR GTDTSVGIVG [SEQ ID NO:3].

13. The polynucleotide according to any one of statements 1 to 14, which is an Artificial Bacterial Chromosome.

14. The polynucleotide according to statement 15, wherein the BAC comprises an inducible bacterial ori sequence for amplification of said BAC to more than 10 copies per bacterial cell, and
a viral expression cassette comprising a cDNA of said yellow fever zika chimeric virus and comprising cis-regulatory elements for transcription of said viral cDNA in mammalian cells and for processing of the transcribed RNA into infectious RNA virus.

15. The polynucleotide according to any one of statements 1 to 8, for use as a vaccine.

16. The polynucleotide according to statement 17, for use as a vaccine in the prevention against a Zika viral infection.

17. A method of preparing a vaccine against a Zika infection, comprising the steps of:
a) providing a BAC which comprises
an inducible bacterial ori sequence for amplification of said BAC to more than 10 copies per bacterial cell, and
a viral expression cassette comprising a cDNA of a yellow fever zika chimeric virus according to any one of statements 9 to 12, and comprising cis-regulatory elements for transcription of said viral cDNA in mammalian cells and for processing of the transcribed RNA into infectious RNA virus
b) transfecting mammalian cells with the BAC of step a) and passaging the infected cells
c) validating replicated virus of the transfected cells of step b) for virulence and the capacity of generating antibodies and inducing protection against Zika virus infection.
d) cloning the virus validated in step c into a vector
e) formulating the vector into a vaccine formulation.

18 The method according to statement 17, wherein the vector is BAC, which comprises an inducible bacterial ori sequence for amplification of said BAC to more than 10 copies per bacterial cell.

19. A polynucleotide comprising the sequence of a live, infectious, attenuated Yellow Fever—Zika chimeric virus wherein the nucleotide sequence encoding the signal sequence and prME protein of said yellow virus is replaced by a nucleotide sequence encoding the signal sequence and the prME protein of a Zika virus, so that said signal sequence and prME protein of said Zika are expressed, characterised in that the encoded amino acid of the prME protein of a Zika virus differs from the wild type Zika sequence by the Ser742Leu substitution as indicated in SEQ ID NO:2.

Herein signal sequence refers to the C-terminal part of the Capsid protein.

20. The polynucleotide according to statement 19, wherein the encoded amino acid sequence of the Zika E protein comprises the sequence IHQIFGAAFKLL-FGGMSWFSQ [SEQ ID NO: 6].

21. The polynucleotide according to statement 19 or 20, which further differs from the wild type sequence by the Ala327Thr substitution as indicated in SEQ ID NO:2.

22. The polynucleotide according to any one of statements 19 to 21, wherein the encoded amino acid sequence of the Zika E protein comprises the sequence CVTVMAQDKPTVDIELVTTTV [SEQ ID NO: 7].

23. The polynucleotide according to any one of statements 19 to 22, wherein the encoded signal sequence and the prME protein of the Zika virus has the amino acid sequence depicted in SEQ ID NO: 5.

24. The polynucleotide according to any one of statements 19 to 23, wherein the encoded amino acid sequence of the NS2A protein of the yellow fever virus has the Val1318Met substitution as indicated in SEQ ID NO:2, and/or wherein the encoded amino acid sequence of the NS4B protein of the yellow fever virus has the Glu2416Lys substitution as indicated in SEQ ID NO:2.

25. The polynucleotide according to any one of statements 19 to 24, wherein the yellow virus backbone has, compared with the sequence of YFV 17D, the mutations g4070a, t7333a, g7364a with reference to the nucleotide numbering of SEQ ID NO: 1.

26. The polynucleotide according to any one of statements 19 to 25, wherein the yellow virus is the YFV 17D attenuated virus.

27. The polynucleotide according to any one of statements 19 to 26, wherein the Zika virus is the Yap strain with accession number EU545988.

28. The polynucleotide according to any one of statements 19 to 27, comprising the open reading frame from nucleotide 119 to 10393 depicted in SEQ ID NO:1. (stopcodon excluded).

29. The polynucleotide according to any one of statements 19 to 28, comprising the sequence depicted in SEQ ID NO:1.

30. The polynucleotide according to any one of statements 19 to 29, wherein the nucleotide sequence of the signal peptide of the Zika virus encodes the amino acid sequence GTDTSVGIVGLLLTTAMA [SEQ ID NO:4].

31. The polynucleotide according to any one of statements 19 to 30, wherein the encoded sequence at the junction of the C protein of the YF and the signal peptide of the Zika virus encodes the amino acid sequence comprising MRGLSSRKRR GTDTSVGIVG [SEQ ID NO:3].

32. The polynucleotide according to any one of statements 19 to 31, which is an Artificial Bacterial Chromosome.

33. The polynucleotide according to statement 32, wherein the BAC comprises an inducible bacterial ori sequence for amplification of said BAC to more than 10 copies per bacterial cell, and a viral expression cassette comprising a cDNA of said yellow fever zika chimeric virus and comprising cis-regulatory elements for transcription of said viral cDNA in mammalian cells and for processing of the transcribed RNA into infectious RNA virus.

34. A live, infectious, attenuated Yellow Fever—Zika chimeric virus wherein the signal sequence and prME protein of said yellow virus are replaced by the signal sequence and the prME protein of a Zika virus, characterised in that the amino acid sequence of the prME protein of the Zika virus differs from the wild type Zika sequence by the Ser742Leu substitution as indicated in SEQ ID NO:2.

Herein signal sequence refers to the C-terminal part of the Capsid protein.

35. The Yellow Fever—Zika chimeric virus according to statement 34, comprising in the Zika E protein the sequence IHQIFGAAFKLLFGGMSWFSQ [SEQ ID NO: 6]

36. The Yellow Fever—Zika chimeric virus according to statement 34 or 35, which further differs from the wild type sequence by the Ala327Thr substitution as indicated in SEQ ID NO:2.

37. The Yellow Fever—Zika chimeric virus according to any one of statements 34 to 36, comprising in the Zika E protein the sequence CVTVMAQDKPTVDIELVTTTV [SEQ ID NO: 7].

38. The Yellow Fever—Zika chimeric virus according to any one of statements 34 to 37, wherein the signal sequence and the prME protein of the Zika virus has or comprisise the amino acid sequence depicted in SEQ ID NO: 5.

39. The Yellow Fever—Zika chimeric virus according to any one of statements 34 to 38, wherein the amino acid sequence of the NS2A protein of the yellow fever virus has the Val1318Met substitution as indicated in SEQ ID NO:2, and/or wherein the amino acid sequence of the NS4B protein of the yellow fever virus has the Glu2416Lys substitution as indicated in SEQ ID NO:2.

40. The Yellow Fever—Zika chimeric virus according to any one of statements 34 to 39, wherein the yellow virus is the YFV 17D attenuated virus.

41. The polynucleotide according any one of statements 34 to 40, wherein the Zika virus is the Yap strain with accession number EU545988.

42. The Yellow Fever—Zika chimeric virus according to any one of statements 34 to 41, comprising the amino acid sequence GTDTSVGIVGLLLTTAMA [SEQ ID NO:4].

43. The Yellow Fever—Zika chimeric virus according to any one of statements 34 to 42, wherein the amino acid sequence at the junction of the C protein of the Yellow Fever virus and the signal peptide of the Zika virus has the amino acid sequence MRGLSSRKRR GTDTSVGIVG [SEQ ID NO:3].

44. A Yellow Fever—Zika chimeric virus according to any one of statements 34 to 43, for use as a vaccine.

45. A Yellow Fever—Zika chimeric virus according to statement 44, for use as a vaccine in the prevention against a Zika viral infection.

46. The polynucleotide according any one of statements 19 to 33 encoding a Yellow Fever—Zika chimeric virus, for use as a vaccine.

47. The polynucleotide according to statement 46, for use as a vaccine in the prevention against a Zika viral infection.

48. A pharmaceutical composition comprising a polynucleotide sequence encoding a Yellow Fever—Zika chimeric virus according any one of statements 19 to 43, and a pharmaceutical acceptable carrier.

49. A pharmaceutical composition comprising a Yellow Fever—Zika chimeric virus according any one of statements 34 to 43, and a pharmaceutical acceptable carrier.

50. A method of preparing a vaccine against a Zika infection, comprising the steps of:
a) providing a BAC which comprises
an inducible bacterial ori sequence for amplification of said BAC to more than 10 copies per bacterial cell, and
a viral expression cassette comprising a cDNA of a yellow fever zika chimeric virus according to any one of statements 19 to 33, and comprising cis-regulatory elements for transcription of said viral cDNA in mammalian cells and for processing of the transcribed RNA into infectious RNA virus
b) transfecting mammalian cells with the BAC of step a) and passaging the infected cells
c) validating replicated virus of the transfected cells of step b) for virulence and the capacity of generating antibodies and inducing protection against Zika virus infection.
d) cloning the virus validated in step c into a vector,
e) formulating the vector into a vaccine formulation.

51. The method according to statement 51, wherein the vector is a BAC which comprises an inducible bacterial ori sequence for amplification of said BAC to more than 10 copies per bacterial cell.

52. A method of inducing a neutralizing antibody response against Zika virus in a subject, thereby preventing an infection by Zika virus, comprising the step of administering to said subject the Yellow Fever—Zika chimeric virus of statements 34 to 43.

53. A method of inducing a neutralizing antibody response against Zika virus in a subject, thereby preventing an infection by Zika virus, comprising the step of administering to said subject a nucleotide sequence encoding chimeric live infectious attenuated *flavivirus* of a first and a second *flavivirus* in accordance with any one of statements 19 to 43.

DETAILED DESCRIPTION

Figure Legends

FIG. 1 Nucleotide and predicted polyprotein sequence of chimeric YF-ZIKprME vaccine virus.
<1>

Figures 2, 3:
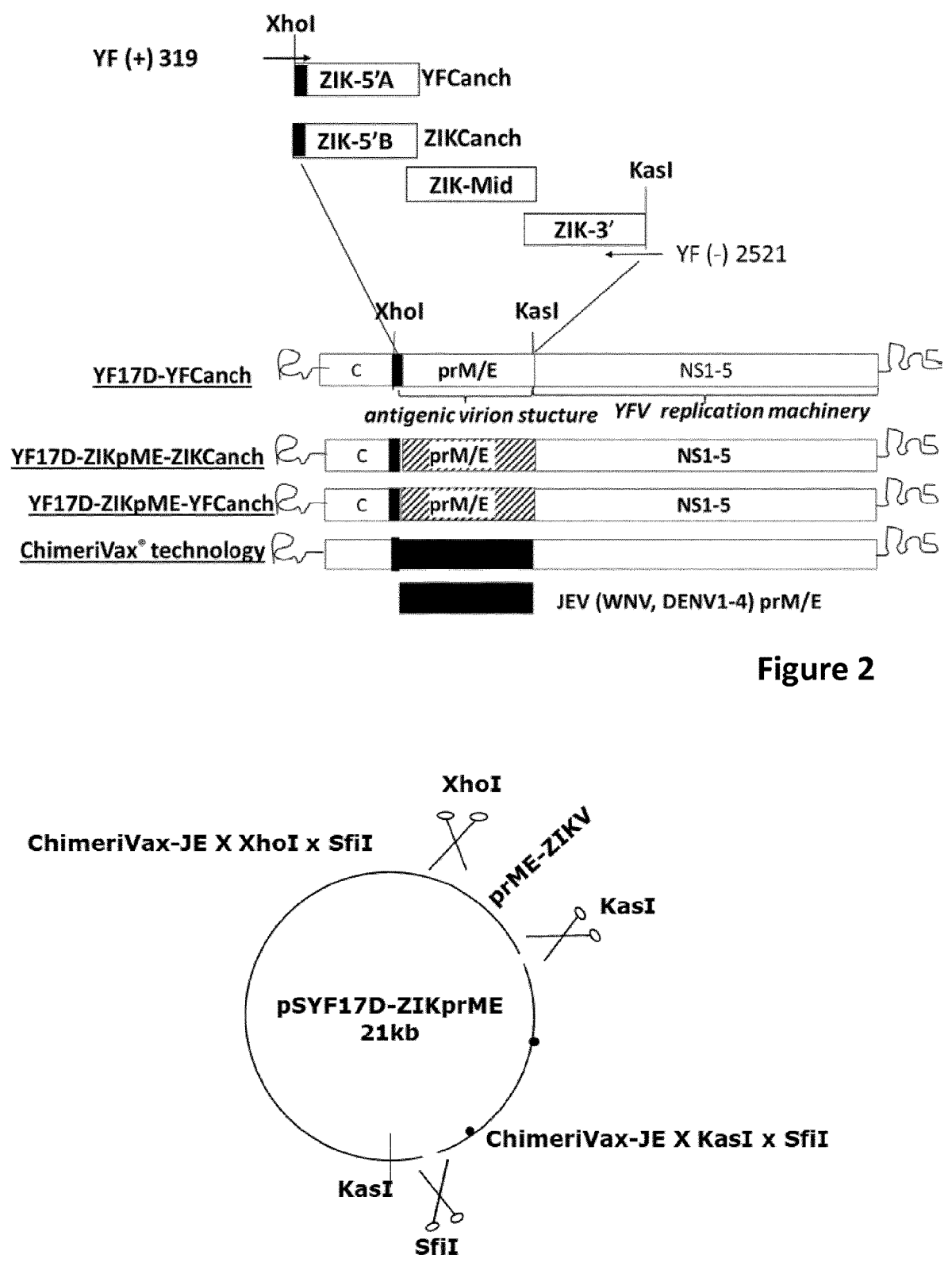

FIG. 2 Schematic representation of the YFV genome and its chimeric derivatives. The prME of YFV and its capsid anchor (C-signal) sequence were replaced by those of ZIKV to generate an attenuated yet replication competent virus. The upper panel depicts ZIKV gene blocks containing overlapping sequences with restriction sites for direct cloning into the YFV plasmid vector. ZIK 5'A contained the capsid anchor (C-signal sequence) of YFV while ZIK 5'B contains that of ZIKV. The bottom panels show the chimeric virus generated and other chimeric technologies that employ the same approach, albeit with prME of other heterologous *flaviviruses*.

FIG. 3 Schematic of the cloning strategy for the construction of pShuttle/ChimeriVax-ZIK-ZIKCanch. Zika virus-Yap (2007) polyprotein ORF nt 313 . . . 2382 was cloned into YF17D-ATCC between nucleotides 1 . . . 421 and 2452 . . . 10862, respectively. The last two codons of the ZIKV E gene where mutated to generate a KasI restriction endonuclease site (resulting in an amino acid change Serin-Alanin to Glycin-Alanin). The parental inducible BAC plasmid used in this study is pShuttle/ChimeriVax-JE which is an inducible BAC derived from Synthetic Construct #1 from WO2014174078 to express a ChimeriVax-JE virus that is similar to the construct made by Arroyo et al.
<1>

Numbering on highlighted letters correspond to nucleotides changes reported in FIG. 5. Numbers in brackets refer to the numbering in SEQ ID NO:1

Lower cases correspond to ZIKV-Yap 2007 prME with the bold/underlined sequence representing the ZIKV anchor domain.

Upper cases correspond to YFV 17D sequences.

n=G or A (A being the dominant peak) resulting in Thr (or Ala).

2001. pSYF17D-ZIK-prME: inducible BAC expressing chimeric YF-ZIKprME. The dots ** represent mutations already present in the ChimeriVax-JE backbone.

FIG. 4 Structure of C-prM junctions in natural *flaviviruses* and synthetic chimeric *flaviviruses*. Amino acid sequences upstream and downstream of the C anchor domain (=prM signal peptide) are shown in single letter SI abbreviation. Legend: (2a/3)—NS2b/3 protease cleavage site; (sign)—signal peptidase cleavage site; * are gaps introduced to facilitate sequence alignments.

FIG. 5 Mutational pattern of synthetic chimeric *flaviviruses* Chimerivax-JE (prior art) and novel YF-ZIKprME (YF/ZIKV-ZIK-Canch). FIG. 5 shows an overview of nucleotide and amino acids modifications in various chimeric constructs I-V. The numbering of the modifications is explained in Table 2 and the accompanying explanation. The copy DNAs of the parental virus YFV-17D (I) had been modified by Arroyo et al. (2001) *J. Virol.* 75, 934-942, to carry the prME sequence of the JE SA14-14-2 vaccine. Respective Chimerivax-JE virus (II) required adaptive mutations 1 and 2 for full replication fitness. Construct (III) that is based on (I) as described in PCT/EP2014/058459 (WO2014174078) with the prME sequence of the ZIKV-Yap 2008 strain plus an additionally engineered (translationally silent) mutation 3 (Xho1 restriction site) was not viable. Introduction of mutations 1 (accompanied with a translationally silent BstE2 restriction site; double nucleotide mutation 4) and 2 (accompanied with a translationally silent Nhe1 restriction site; mutation 5) into the backbone of (III) yield a viable YFV/ZIKV chimera, yet with poor replication fitness. Intracellular and extracellular passaging leads to fixation of mutations 6 to 9 (triangles) in passage 5 (recombinant virus V).

Figure 6:
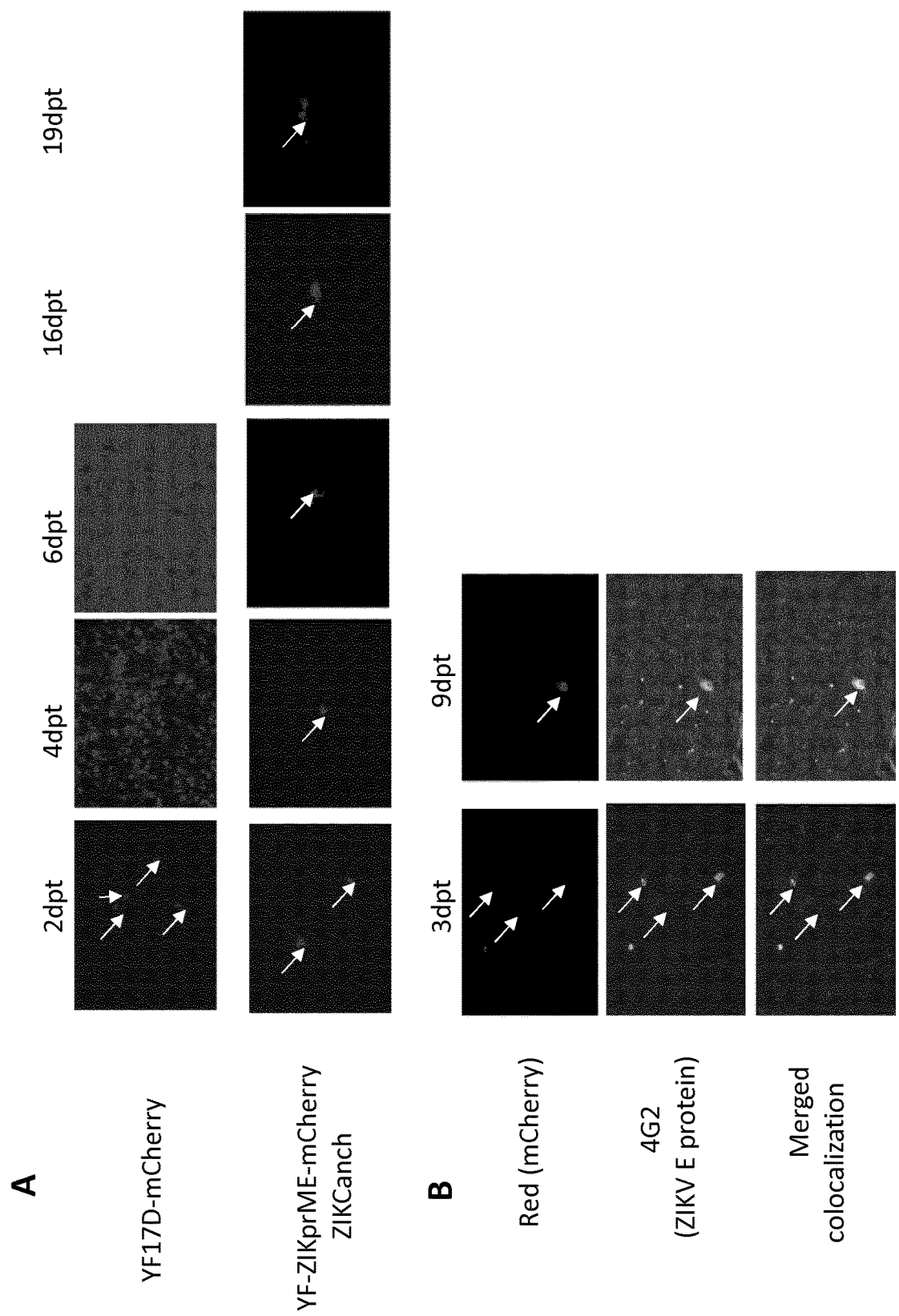

FIG. 6 Growth and propagation of mCherry YF-ZIK chimeric virus. Based on the YFV 17D backbone described in WO2014174078 (see also Construct I in FIG. 3) we constructed BACS expressing YF-ZIK chimeric viruses that are tagged with a mCherry gene expressed that is expressed as N-terminal translational fusion to the YFV 17D polyprotein essentially as described by Fischl & Bartenschlager (2013) *Methods. Mol. Biol.* 1030, 205-219. As a comparator, YFV 17D containing mCherry was constructed within the same backbone. (A) The upper panel show the growth and massive amplification of YFV mCherry in contrast to mCherry YF-ZIK chimeric virus (Lower panel) with little replication, yet no amplification or spread of the virus. (B) Staining of YF-ZIKprME virus (at indicated time points) with monoclonal Ab, 4G2, to confirm its replication. Figure reveals the co-localization of mCherry and envelop protein staining with 4G2 indicative of virus replication, yet no spread. [isolated stained cells indicated with arrows]

Figure 7:
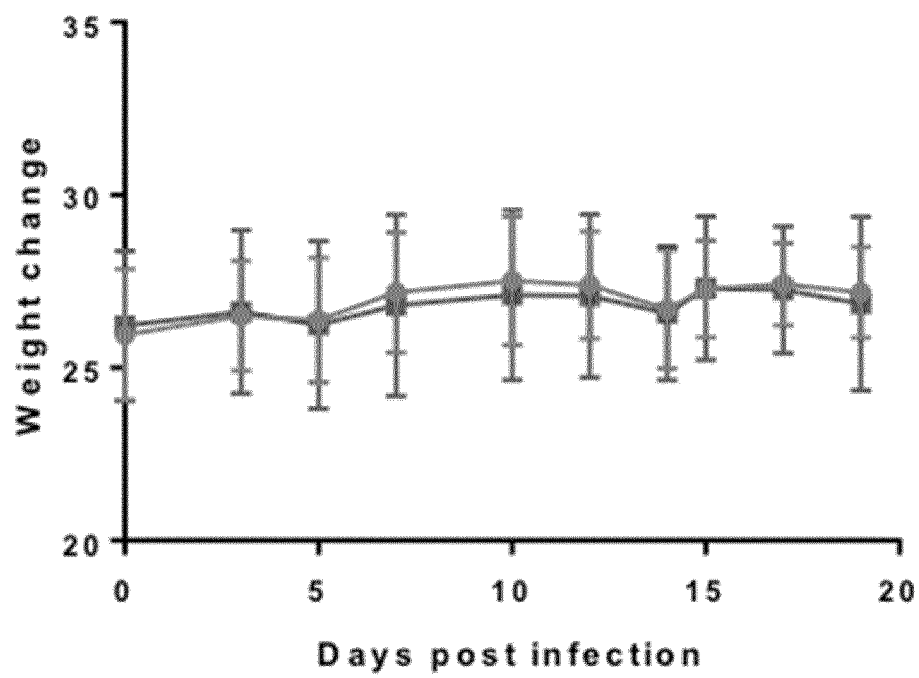

FIG. 7 Attempt to adapt chimeric YF ZIK viruses by intracranial passage in mice. Neither variant (circles (top line) and squares (lower lined)), neither with the capsid anchor (C-signal sequence) of YFV nor that of ZIKV, caused any morbidity or mortality in mice (weight loss) following intracranial inoculation of supernatant of transfected cells prior to virus passage and adaptation to more vigorous growth in tissue culture.

FIG. 8 Comparison of classical means (A) of generating and adapting recombinant *flaviviruses* (e.g. Arroyo et al. 2001, cited above) with novel staged approach (C). Alternatively to (A), infectious recombinant progeny has been amplified by intracranial inoculation into the brains of mice or mouse pups (B). IVT—in vitro transcription; TFXN—transfection.

Figure 9:
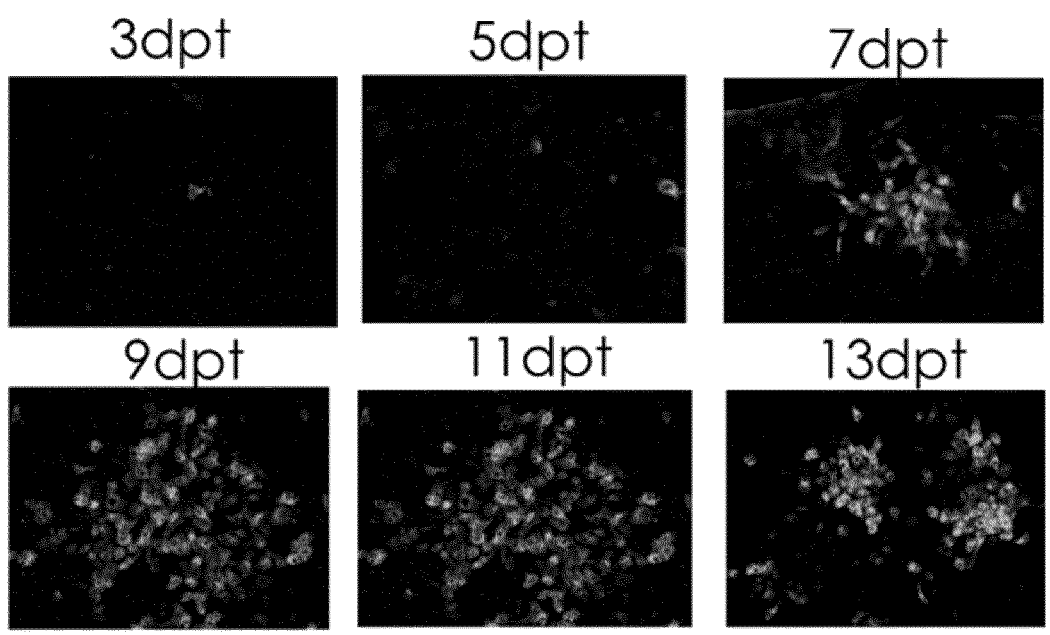

FIG. 9 Immunofluorescence assay at selected time points during the intracellular passaging of YF17D-ZIKprME. After splitting and resuspension of cells, 300 μl of cell suspension was seeded in Lab-tek 8well chamber slides and incubated overnight prior to subjection at indicated time points for IFA staining and microscopy. The pan-*flavivirus* monoclonal antibody (mAb) 4G2 was used to stain for viral envelope protein, serving as a surrogate for viral translation and replication. Before day 7 post transfection (dpt), IFA staining could barely detect positive signals in single cells. At 7 dpt, only 1 group (focus) of cells stained positive with 4G2 (with a few single infected cells) and by day 13, the number of foci had increased to more than 20. Focus: a group of cells that stained positive for the E protein C) Upon passaging, the low titre chimeric virus could be grown to significantly high titres from $1.25\times10^3$ PFU/mL (P1) to $1.75\times10^6$ PFU/mL (P3). D) Plaque phenotype of YF17D and its attenuated derivative YF-ZIKprME revealed that YF17D formed plaques that were markedly bigger than YF-ZIKprME suggesting that the chimeric virus might be as attenuated. Analysis of cells transfected with pShuttle/ChimeriVax-ZIK-YFCanch did not reveal any virus amplification.

Figure 10:
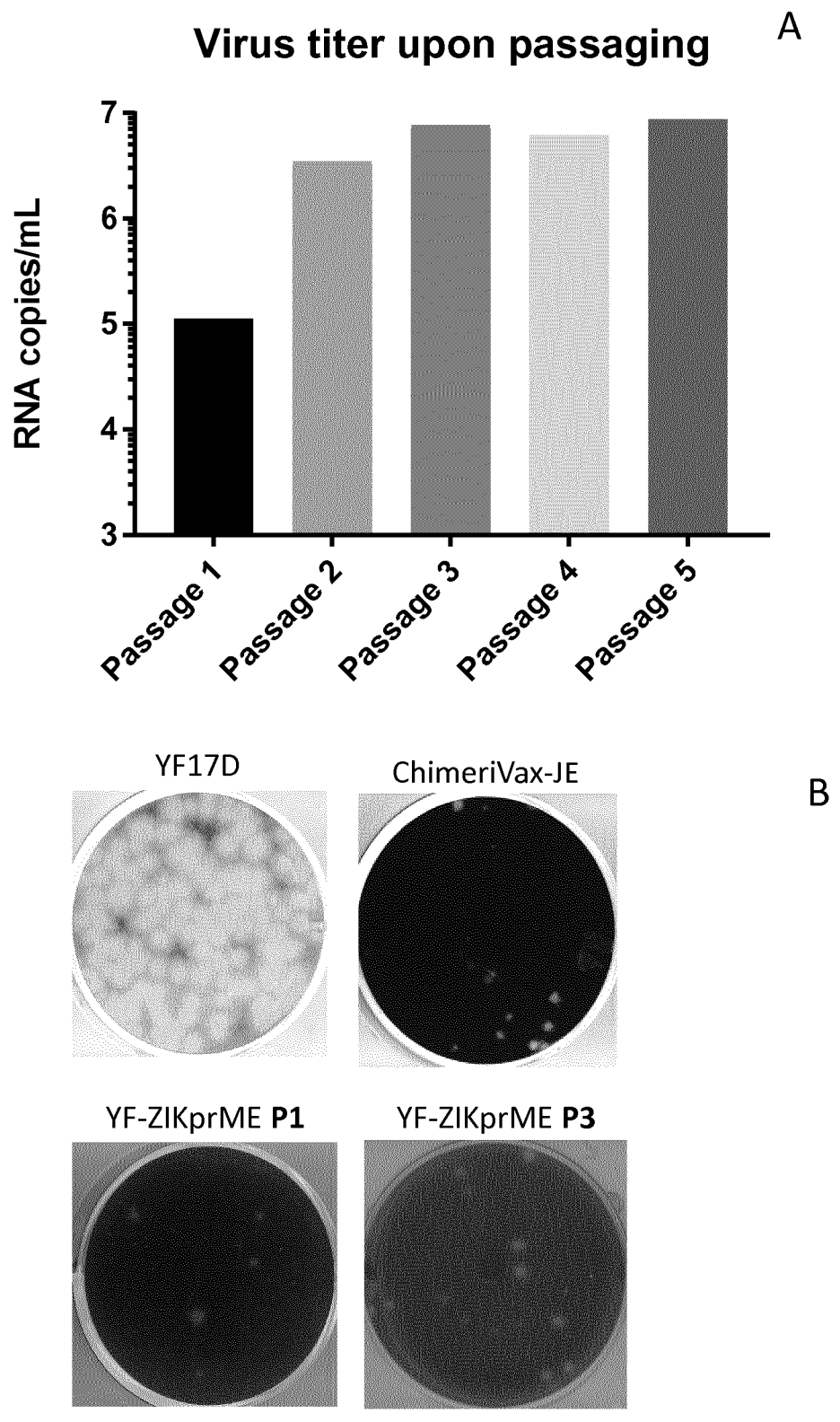

FIG. 10 YF-ZIKprME virus titres upon passaging and plaque phenotypes. (A) Upon extracellular passaging of YF-ZIKprME, decent virus yields could be achieved. RNA-qPCR values show an about 1.5-1.7 log increase in extracellular virus RNA from passage 1 to 3 which stayed fairly constant upon further passaging. (B) YF-ZIKprME chimeric virus formed smaller plaques compared to its parental YFV suggesting the attenuation of the former in vitro. Further passaging of YF-ZIKprME yielded a larger, somewhat heterogeneous plaque phenotype [suggesting the existence of a heterogeneous virus population which could be confirmed by sequencing (heterogeneity at nt position 1097)]. Plaques formed by ChimeriVax-JE for comparison. In summary, YFV 17D formed plaques that were markedly bigger than JEV and ZIKV chimeric viruses, with no marked difference in plaque size and morphology between the two chimeric viruses suggesting that YF-ZIKprME might be as attenuated as its sister chimera ChimeriVax-JE (YF-JEprME).

FIG. 11 Production of infectious progeny from pShuttle/ChimeriVax-ZIK-ZIKCanch after intracellular passage. Infectious YF-ZIKprME in tissue culture supernatants 22 days after transfection with pShuttle/ChinneriVax-ZIK-ZIK-Canch by medium transfer and infection of naive Vero cells. Subsequent infection could be detected by IFA stain for E protein (mAb 4G2). Transfection with pShuttle/ChimeriVax-ZIK-YFCanch did not yield any infectious viruses.

FIG. 12 New antigenicity of YF-ZIKprME. Cells infected with YFV 17D, a field isolate of ZIKV BeH819015, or YF-ZIKprME were stained for E antigen expression using either the pan-flavi mAb 4G2 (left), or using a JEV specific mAb (Biosource) cross-reacting only with ZIKV E yet not YFV E proteins, and for YFV NS1 using mAB 1A5 (Schlesinger et al. (1983) Virology 125, 8-17). Regarding the E protein, YF-ZIKprME infected cells stain like ZIKV BeH819015 infected cells; regarding the NS1 protein like YFV 17D infected cell. This indicates that YF-ZIKprME is a true chimera expressing antigens from both ZIKV and YFV.

FIG. 13 Growth kinetics of YF17D and its chimeric derivative YF-ZIKprME on mammalian and mosquito cell lines. (A) As expected YF17D showed reduced viral growth kinetics in C6/36 mosquito cells (compared to its growth in Vero cells) as opposed to (B) YF-ZIKprME with abolished replication in the same mosquito cell line, raising the safety margin of latter virus for mosquito transmission in a vaccinated population.

FIG. 14 Immunogenicity (seroconversion) and protective efficacy (survival of lethal challenge) induced by YF-ZIKprME. (A) Indirect immunofluorescence assay (IIFA) of serum from mice vaccinated with YF-ZIKprME revealed the presence of high titre antibodies 21 days post vaccination with $10^5$ PFU of YF-ZIKprME. Vaccinated mice (#770-772) seroconvert to high titres (>1:100) of ZIKV specific antibodies. Vaccination with this high dose is safe and does not cause any overt side effects in AG129 mice [a similarly high inoculum of YFV 17D represents a 10,000-fold lethal dose and is uniformly lethal in AG129 mice] (B) Vaccinated and non-vaccinated mice were challenged after 21 days and monitored daily for weight loss and signs of disease with a significant difference (p=0.008) between vaccinated and non-vaccinated mice. (C) Upon challenge, non-vaccinated mice succumbed to the challenge virus with mean day to euthanasia of 14±1, while vaccinated mice did not show any significant weight loss nor other disease symptoms. Vaccinated mice were monitored for 28 days, yet no death was recorded.

Figure 15:
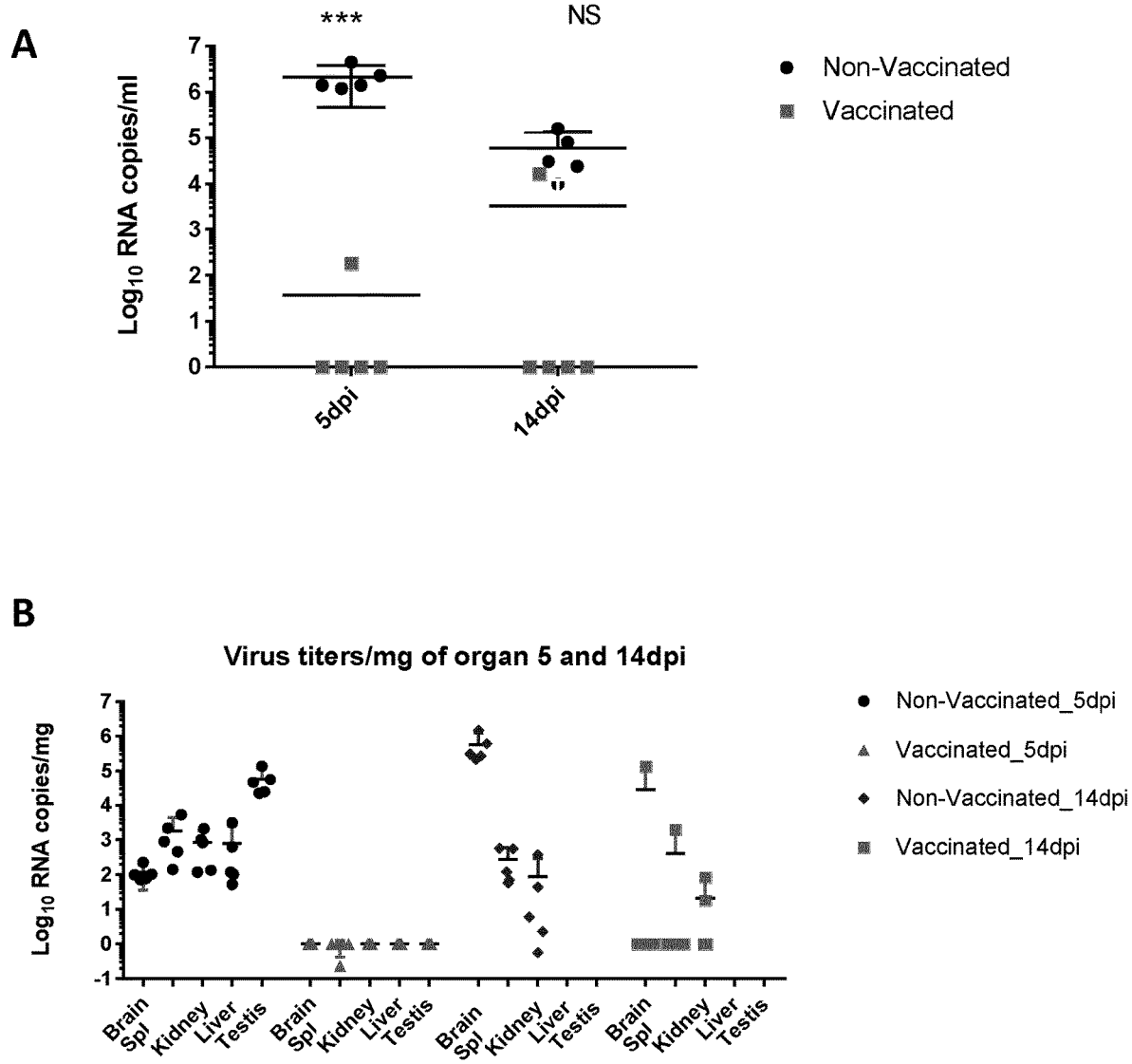

FIG. 15 Protection from viremia and virus dissemination to target organs by vaccination using YF-ZIKprME. Blood (A) and organs (B) collected at day 5 and 10 post challenge revealed a marked difference in viral titres between vaccinated and non-vaccinated mice at day 5 (p=0.0003) and at day 10.

FIG. 16 Protection from lethal challenge by vaccination with low dose inoculum. (A) Study design to show protection after vaccination with low dose inoculum. Mice vaccinated ip with $1\times10^2$ PFU YF17D-ZIKprME seroconverted (B) and were protected from virus induced weight loss (C) and mortality (D) when challenged with $10^4$ PFU MR766. Boosting at 14 days post vaccination is not required to confer full protection but however has additional benefits regarding magnitude of humoral immune response (B, middle versus lower panel).

Flaviviruses have a positive single-strand RNA genome of approximately 11,000 nucleotides in length. The genome contains a 5' untranslated region (UTR), a long open-reading frame (ORF), and a 3' UTR. The ORF encodes three structural (capsid [C], precursor membrane [prM], and envelope [E]) and seven non-structural (NS1, NS2A, NS2B, NS3, NS4A, NS4B, and NS5) proteins. Along with genomic RNA, the structural proteins form viral particles. The non-structural proteins participate in viral polyprotein processing, replication, virion assembly, and evasion of host immune response. The signal peptide at the C terminus of the C protein (C-signal peptide; also called C-anchor domain ("canch") regulates *flavivirus* packaging through coordination of sequential cleavages at the N terminus (by viral NS2B/NS3 protease in the cytoplasm) and C terminus (by host signalase in the endoplasmic reticulum [ER] lumen) of the signal peptide sequence. C terminal part of the C protein Mutations in the signal sequence can have a profound effect on the assembly of a *flavivirus*. In the same context, the assembly of a *Flavivirus* may be dramatically influenced in chimeric *flaviviruses* wherein the prME genes of a second *flavivirus* are cloned in frame with the C-signal peptide of a first *flavivirus*. Chimeric *flaviviruses* have been made wherein either the C-signal peptide of the first virus is preserved or wherein the C-signal peptide of the first virus is replaced by the one of the second virus. Also mutations in the signal peptide have been introduced to evaluate the effect of cleaving efficiency and subsequent viral replication.

The genus *flavivirus* comprises viruses of medical importance such as the dengue, yellow fever, West Nile, Japanese encephalitis, tick-borne encephalitis and Zika viruses. Of the medically important *flaviviruses*, only the tick-borne encephalitis virus, Omsk hemorrhagic fever virus, Kyasanur forest disease virus and Alkhurma hemorrhagic fever virus are transmitted by ticks, the others are transmitted by mosquito vectors mainly of the *Aedes* spp. and *Culex* spp. The genome of *flaviviruses* has been well characterized, with each member having the same genomic arrangement in which the genes are flanked by untranslated regions at the 5' and 3' ends, respectively. The positive-sense single-stranded genome is co- and post translationally modified into a single polyprotein that is later cleaved by viral and host proteins into three structural [Capsid (C), premembrane (prM), envelope (E)], and seven non-structural (NS1, NS2A, NS2B, NS3, NS4A, NS4B, NS5) proteins. The structural proteins are responsible for forming the (spherical) structure of the virion, initiating virion adhesion, internalization and release into cells, thereby orchestrating the virus life cycle. The non-structural proteins on the other hand are responsible for viral replication, modulation and evasion of immune responses in infected cells, and the transmission of viruses to mosquitoes. The intra- and inter-molecular interactions between the structural and non-structural proteins play key roles in the virus infection and pathogenesis. The envelop protein has been well characterized and shown to be the main determinant of antigenicity and humoral immune response. It has been shown that the prM gene plays a great role during the attachment and release of viral particles into the cytoplasm, permitting RNA replication and virus propagation. To demonstrate the importance of the prM in the aforementioned processes, various groups have cloned the the envelope (E) protein with or without the prM into plasmid vectors and monitor for the production of subviral particles. Results from these studies highlight the importance of the prM region in the production of subviral particles and elicitation of immune responses. Here, we describe the chimeric virus vaccine candidate generated by replacing the prM and E of the well characterized YFV 17D by an epidemic strain of Zika virus isolated from the Yaps Island in 2007. The rationally designed chimeric virus vaccine explores the safety of YF17D vector and the immunogenicity of the prME genes, making it a suitable candidate for further development. Recent evidence shows that ZIKV isolates that date from later epidemics contain amino acid substitutions that result in a higher risk of congenital birth defects (Yuan et al. (2017) *Science* 358, 933-936) and their prME genes may thus not be preferred antigens of choice for development of live attenuated vaccines due to the inherent risk of severe adverse effects.

A first aspect of the invention relates to chimeric constructs between the Yellow *Flavivirus* and the Zika virus as such that a novel chimeric recombinant *Flavivirus* is generated that is replication competent and can be used as a live-attenuated vaccine to protect from Zika virus infection and its sequelae such as congenital malformations caused by transplacental (mother-to-child) transmission of Zika virus infection. Protection from ZIKV infection using the chimeric construct as vaccine is surprisingly potent exemplified in protection from vaccine challenge in the most stringent AG129 mouse Zika virus infection model that has been described by the present inventors in great detail before (Zmurko et al. (2016) *PLoS Negl. Trop. Dis.* 10, e0004695). Intriguingly, in this stringent model protection was achieved from a single vaccine dose and protected against very high doses of challenge virus ($10^4$ PFU of ZIKV strain MR766 corresponding to a $10^4$-fold lethal dose). This protection extends firstly to protection from challenge virus viremia with a reduction by at least 5 Log 10 in viral RNA copy numbers compared to non-vaccinated individuals at peak of viremia 5 days after infection; down to non-detectable levels). Second, vaccination results in a most marked reduction of virus loads in several relevant organs including the brain and the testis. In either case reduction may reach non-detectable levels indicative for the construct being able to confer sterilizing immunity.

Only a single dose of the construct was sufficient to confer protection. Generally doses of $10^4$ PFU have been considered when using live-attenuated Zika viruses for vaccination (see e.g. Shan et al. (2017) *Nat. Commun.* 8, 676). For our construct we show that much lower doses (down to $10^2$ PFU) were sufficient to confer 100% protection from lethal challenge in AG129 mice with no need to booster vaccinate.

Our construct does not replicate anymore in mosquito cells. In YFV 17D its reduced replication competence in mosquito cells is considered an important safety feature prohibiting uncontrolled vaccine virus spread in the field (environmental safety). In line, our construct can be considered environmentally very safe.

In our construct the prME gene of the YF virus is replaced by the prME gene of the Zika virus. In addition the signal peptide of YF virus has been replaced by the signal peptide of Zika virus. As illustrated by the examples, the precise sequence of the signal peptide has a dramatic impact on the replication of the chimeric construct.

A chimeric *flavivirus* with a Dengue backbone and Zika prME has been described by Xie. The DENV-2 infectious clone used to generate this chimera contains the cDNA sequence of DENV-2 strain D2Y98P. This particular DENV-2 strain is a non-attenuated field isolate that has been described by Grant et al. (2011) *J. Virol.* 85, 7775-7787) to be especially virulent in mice resulting in organ damage or dysfunction and increased vascular permeability that are hallmarks of severe DENV infection in patients (Tan et al. (2010) *PLoS Negl. Trop. Dis.* 4, e672). DENV-2 strain D2Y98P can thus be considered a particularly virulent DENV-2 strain.

In general a virus is considered live when is has the potency to infect a host cell, amplify and produce infectious progeny. A virus is considered attenuated when it lost its virulence to a degree that it cannot cause overt disease anymore in a susceptible host in which a comparable dose of the originally pathogenic parent virus can be expected to induce such disease.

The propagation of the chimeric constructs prior to attenuation, as well as the cDNA of a construct after attenuation requires an error proof replication of the construct. The use of Bacterial Artificial Chromosomes, and especially the use of inducible BACS as disclosed by the present inventors in WO2014174078, is particularly suitable for high yield, high quality amplification of cDNA of RNA viruses such as chimeric constructs of the present invention.

A BAC as described in this publication BAC comprises:
an inducible bacterial ori sequence for amplification of said BAC to more than 10 copies per bacterial cell, and
a viral expression cassette comprising a cDNA of an the RNA virus genome and comprising cis-regulatory elements for transcription of said viral cDNA in mammalian cells and for processing of the transcribed RNA into infectious RNA virus.

As is the case in the present invention the RNA virus genome is a chimeric viral cDNA construct of two RNA virus genomes.

In these BACS, the viral expression cassette comprises a cDNA of a positive-strand RNA virus genome, an typically
a RNA polymerase driven promoter preceding the 5' end of said cDNA for initiating the transcription of said cDNA, and
an element for RNA self-cleaving following the 3' end of said cDNA for cleaving the RNA transcript of said viral cDNA at a set position.

The BAC may further comprise a yeast autonomously replicating sequence for shuttling to and maintaining said bacterial artificial chromosome in yeast. An example of a yeast ori sequence is the 2p plasmid origin or the ARS1

(autonomously replicating sequence 1) or functionally homologous derivatives thereof.

The RNA polymerase driven promoter of this first aspect of the invention can be an RNA polymerase II promoter, such as Cytomegalovirus Immediate Early (CMV-IE) promoter, or the Simian virus 40 promoter or functionally homologous derivatives thereof.

The RNA polymerase driven promoter can equally be an RNA polymerase I or III promoter.

The BAC may also comprise an element for RNA self-cleaving such as the cDNA of the genomic ribozyme of hepatitis delta virus or functionally homologous RNA elements.

The formulation of DNA into a vaccine preparation is known in the art and is described in detail in for example chapter 6 to 10 of "DNA Vaccines" Methods in Molecular Medicine Vol 127, (2006) Springer Saltzman, Shen and Brandsma (Eds.) Humana Press. Totoma, N.J. and in chapter 61 Alternative vaccine delivery methods, Pages 1200-1231, of Vaccines (6th Edition) (2013) (Plotkin et al. Eds.). Details on acceptable carrier, diluents, excipient and adjuvant suitable in the preparation of DNA vaccines can also be found in WO2005042014, as indicated below.

"Acceptable carrier, diluent or excipient" refers to an additional substance that is acceptable for use in human and/or veterinary medicine, with particular regard to immunotherapy.

By way of example, an acceptable carrier, diluent or excipient may be a solid or liquid filler, diluent or encapsulating substance that may be safely used in systemic or topic administration. Depending upon the particular route of administration, a variety of carriers, well known in the art may be used. These carriers may be selected from a group including sugars, starches, cellulose and its derivatives, malt, gelatine, talc, calcium sulphate and carbonates, vegetable oils, synthetic oils, polyols, alginic acid, phosphate buffered solutions, emulsifiers, isotonic saline and salts such as mineral acid salts including hydrochlorides, bromides and sulphates, organic acids such as acetates, propionates and malonates and pyrogen-free water.

A useful reference describing pharmaceutically acceptable carriers, diluents and excipients is Remington's Pharmaceutical Sciences (Mack Publishing Co. N.J. USA, (1991)) which is incorporated herein by reference.

Any safe route of administration may be employed for providing a patient with the DNA vaccine. For example, oral, rectal, parenteral, sublingual, buccal, intravenous, intra-articular, intra-muscular, intra-dermal, subcutaneous, inhalational, intraocular, intraperitoneal, intracerebroventricular, transdermal and the like may be employed. Intramuscular and subcutaneous injection may be appropriate, for example, for administration of immunotherapeutic compositions, proteinaceous vaccines and nucleic acid vaccines. It is also contemplated that microparticle bombardment or electroporation may be particularly useful for delivery of nucleic acid vaccines.

Dosage forms include tablets, dispersions, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release of the therapeutic agent may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

DNA vaccines suitable for oral or parenteral administration may be presented as discrete units such as capsules, sachets or tablets each containing a pre-determined amount of plasmid DNA, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association one or more agents as described above with the carrier which constitutes one or more necessary ingredients. In general, the compositions are prepared by uniformly and intimately admixing the DNA plasmids with liquid carriers or finely divided solid carriers or both, and then, if necessary, shaping the product into the desired presentation.

The above compositions may be administered in a manner compatible with the dosage formulation, and in such amount as is effective. The dose administered to a patient, should be sufficient to effect a beneficial response in a patient over an appropriate period of time. The quantity of agent (s) to be administered may depend on the subject to be treated inclusive of the age, sex, weight and general health condition thereof, factors that will depend on the judgement of the practitioner.

Furthermore DNA vaccine may be delivered by bacterial transduction as using live-attenuated strain of *Salmonella* transformed with said DNA plasmids as exemplified by Darji et al. (2000) *FEMS Immunol. Med. Microbiol.* 27, 341-349 and Cicin-Sain et al. (2003) *J. Virol.* 77, 8249-8255 given as reference.

Typically the DNA vaccines are used for prophylactic or therapeutic immunisation of humans, but can for certain viruses also be applied on vertebrate animals (typically mammals, birds and fish) including domestic animals such as livestock and companion animals. The vaccination is envisaged of animals which are a live reservoir of viruses (zoonosis) such as monkeys, mice, rats, birds and bats.

In certain embodiments vaccines may include an adjuvant, i.e. one or more substances that enhances the immunogenicity and/or efficacy of a vaccine composition However, life vaccines may eventually be harmed by adjuvants that may stimulate innate immune response independent of viral replication. Non-limiting examples of suitable adjuvants include squalane and squalene (or other oils of animal origin); block copolymers; detergents such as Tween-80; Quill A, mineral oils such as Drakeol or Marcol, vegetable oils such as peanut oil; *Corynebacterium*-derived adjuvants such as *Corynebacterium parvum*; *Propionibacterium*-derived adjuvants such as *Propionibacterium acne*; *Mycobacterium bovis* (Bacille Calmette and Guerin or BCG); interleukins such as interleukin 2 and interleukin 12; monokines such as interleukin 1; tumour necrosis factor; interferons such as gamma interferon; combinations such as saponin-aluminium hydroxide or Quil-A aluminium hydroxide; liposomes; ISCOMt) and ISCOMATRIX (B) adjuvant; mycobacterial cell wall extract; synthetic glycopeptides such as muramyl dipeptides or other derivatives; Avridine; Lipid A derivatives; dextran sulfate; DEAE-Dextran or with aluminium phosphate; carboxypolymethylene such as Carbopol'EMA; acrylic copolymer emulsions such as Neocryl A640; vaccinia or animal poxvirus proteins; sub-viral particle adjuvants such as cholera toxin, or mixtures thereof.

EXAMPLES

Example 1

Plasmid Construction

Plasmid pShuttle/ChimeriVax-JE is an inducible BAC and derivative of Synthetic Construct #1 as disclosed in WO2014174078 that was constructed using standard recombinant DNA methods. Plasmid pShuttle/ChimeriVax-JE was designed to contain the prME sequence of the Japanese encephalitis vaccine SA14-14-2 plus two additional adaptive (missense) codon changes in the YFV 17D NS2A and NS4B regions as described for the ChimeriVax-JE by Arroyo et al. (2001) *J. Virol.* 75, 934-942. The overall structure of said ChimeriVax-JE is depicted as 'Construct II' in Figure FIG. 5 and said codon changes specified as 'mutation 1' and 'mutation 2'. Also as described by Arroyo et al. 2001, a Kas1 site has been was introduced at the end of the prME coding sequence.

Distinct from Arroyo et al. 2001, plasmid pShuttle/ChimeriVax-JE was constructed to contain additional silent XhoI, BstE2 and Nhe1 restriction sites in the YFV 17D sequence, not present in the original ChimeriVax-JE, to serve as genetic markers and for ease of cloning (specified as 'mutations 3', 'mutation 4' and 'mutation 5' in 'Construct IV' in FIG. 5).

The prME region of the Yap (EU545988 Genbank accession (30 Jul. 2008)) ZIKV isolate corresponding to the polyprotein open reading (ORF) nt 313 to 2382 was ordered as gene blocks made by custom DNA synthesis (IDT Integrated DNA Technologies, Haasrode), flanked by the 5' end and NS1 sequences of YFV, namely; ZIK-5'A (YFV capsid anchor), ZIK 5'B (ZIKV capsid anchor), ZIK-Mid, and ZIK-3'. In particular, ZIK-5'A and ZIK 5'B already have the specific fusion of the YF ZIKA at the signal peptide junction to encode for the YFV capsid anchor and ZIKV capsid anchor, respectively.

Gene blocks contained overlapping sequences permitted them to be used directly as templates for fusion PCR using primers YF17D(+)319 (gttgtggaaaatgctggacccaa-gacaaggcttggctgttctaaggaaagtcaagagagt) [SEQ ID NO: 8] and YF17D(−)2521 (tctaaatatgaagataccatctccgcactt-gagctctctcttgccaaagttgatggcgca) [SEQ ID NO:9]. The fusion amplicon generated contained terminal XhoI and KasI sites that allowed for direct ligation into the plasmid pShuttle/ChimeriVax-JE by restriction digest and ligation into its respective XhoI and proximal KasI sites. FIG. 3 shows the overall cloning strategy and the insertion sites in the yellow fever backbone to generate the YF17D-prME-ZIKCanch chimeric virus (incorporating synthetic geneblock ZIK 5'B (ZIKV capsid anchor), referred to as YF-ZIKprME. A YF17D-prME-YFanch chimeric virus incorporating ZIK-5'A (YFV capsid anchor) was constructed accordingly. The respective cDNA constructs pShuttle/YF17D-prME-ZIK-Canch and pShuttle/YF17D-prME-YFCanch are inducible BAC according to WO2014174078

Example 2

Virus Production

Cells used in this study were purchase from ATCC and maintained in Minimum Essential Medium (MEM-Rega-3, Invitrogen Life Technologies) supplemented with 10% FBS, 1% Anti-Anti (1% Streptomycin and Amphoteracin B; Invitrogen), 1% sodium bicarbonate (Gibco, Belgium), 1% glutamine (Gibco, Belgium) and incubated at 37° C., 5% CO2. Virus was generated and propagated in Vero E6 cells, a generally accepted substrate used for the production of *flaviviruses* for vaccine use. Due to our inability to generate an infectious virus capable of orchestrating (i) a full-blown infection following transfection protocol, neither (ii) producing sufficient progeny to initiate replication following intracranial inoculation in mouse brain, a protocol was designed that permitted the in situ replication of the otherwise highly attenuated YF-ZIKprME chimeric virus. To this end, 2.5 µg of either plasmid pShuttle/YF17D-prME-ZIK-Canch or plasmid pShuttle/YF17D-prME-YFCanch were used to transfect $5 \times 10^5$ Vero E6 cells in a 6 well plate using TransIT®-LT1 transfection reagent (Mirrus Bio LLC, Belgium) following manufacturer's instruction. Two days post transfection (dpt), cells were washed twice with PBS, trypsinized and transferred to 25 cm$^3$ flasks in a total volume of 5 ml of 2% FBS medium containing 1% Anti-Anti (1% Streptomycin and Amphotericin B; Invitrogen).

This cycle was repeated for three more times at day 8, 14 and 20 post transfection, each time expending the cell substrate by providing increasingly larger tissue culture vessels. Cell culture was terminated after overall 22 days.

Intracellular replication of chimeric viruses launched from the inducible BACS may lead to the production and release of fully infectious progeny virus particles into the tissue culture supernatant. To allow amplification of such chimeric virus as soon as it emerges also a fraction of the supernatant of the transfected cells was transferred to each next cell passage. Because during the course of intracellular passaging no amplification of YF17D-prME-YFCanch progeny (initiated from pShuttle/YF17D-prME-YFCanch transfection) could be observed by IFA any further attempt to adapt the chimera YF17D-prME-YFCanch as discontinued. The YF17D-prME-ZIKCanch chimeric virus (YF-ZIKprME) derived from transfected pShuttle/YF17D-prME-ZIKCanch was passaged in Vero cells and passage 3 and 5 were used for further study.

TABLE 1

Work flow for the propagation of highly attenuated chimeric virus:

Protocol for the propagation of highly attenuated chimeric flaviviruses

| | | |
|---|---|---|
| Day-1 | Seed Vero E6 cells at $5 \times 10^5$ cells/well in 6well plates | |
| Day 0 | Transfect cells with 2.5 µg of plasmid | |
| Day 1 | | |
| Day 2 | Wash/Trypsonize and transfer all cells to 25 cm$^3$ flask + 2 ml supernatant | |
| Day 3 | 1 day post split (dps) | IFA |
| Day 4 | 2 dps | |
| Day 5 | 3 dps | IFA |
| Day 6 | 4 dps | |
| Day 7 | 5 dps | IFA |
| Day 8 | Wash/Trypsonize and transfer all cells to 75 cm$^3$ flask + 3 ml supernatant | |
| Day 9 | 1 dps | IFA |
| Day 10 | 2 dps | |
| Day 11 | 3 dps | IFA |
| Day 12 | 4 dps | |
| Day 13 | 5 dps | IFA |
| Day 14 | Wash/Trypsonize and transfer all cells to 150 cm$^3$ flask | |
| Day 15 | 1 dps | IFA |
| Day 16 | 2 dps | |
| Day 17 | 3 dps | IFA |
| Day 18 | 4 dps | |
| Day 19 | 5 dps | IFA |

TABLE 1-continued

| Work flow for the propagation of highly attenuated chimeric virus: | | | |
|---|---|---|---|
| | | Protocol for the propagation of highly attenuated chimeric flaviviruses | |
| | Day 20 | Wash/Trypsonize and transfer 1/3 cells to 150 $cm^3$ flask + 1/3 fresh cells | |
| Passage 1 | Day 21 | 1 dpi | IFA |
| | Day 22 | 2 dpi (Infection of naive Vero cells with 200 μl of cell supernatant) | |
| | Day 23 | 3 dpi | IFA |
| | Day 24 | 4 dpi | |
| | Day 25 | 5 dpi | IFA |

Immunofluorescence Assay (IFA) was used at indicated time points to monitor the infectivity and spread of the virus.

Animals. Mice deficient in both interferon alpha and gamma receptors, IFNAGR$^{-/-}$ (AG129; B&K Universal, Marshall Bio resources, UK) were bred in house and vaccinated with $5\times10^2$-$1\times10^5$PFU of YF-ZIKprME prior to being challenged with $1\times10^4$PFU-$1\times10^5$PFU of heterologous strains MR766 as described by Zmurko et al. (2016) *PLoS Negl. Trop. Dis.* 10, e0004695. Mice were monitored for weight change and virus induced disease.

Virus challenge. Six groups (n=5/group) of 6-8 weeks old mice were vaccinated intraperitoneally (i.p) with 200 μl of $1\times10^5$ PFU of vaccine virus and challenged 21 days post vaccination. To determine viremia and virus dissemination to organs after challenge, vaccinated (n=5) and non-vaccinated (n=5) mice were euthanized on day 5 and 14 (at death). Blood was collected through heart puncture while organs were profusely perfused and harvested in two tubes; one in RNAlater (Thermofischer, USA) for overnight storage at 4° C. for RNA fixation and extraction, and in 1.5 mL tubes on dry ice for storage at −80° C. Upon collection, blood samples for viremia were stored on ice, centrifuged at 2500 rpm for 15 minutes and stored at −80° C. for RNA extraction and qRT-PCR. To determine vaccination kinetics and time required to confer protection, mice were randomly caged in groups of 5 (n=5) and vaccinated at various time points (−d21, −d14, −d10 and −d7) prior to challenge with $1\times10^5$PFU MR766. Mice were monitored daily signs of disease and mortality.

RNA extraction and qRT-PCR. Samples were treated as described in Zmurko et al. (2016) *PLoS Negl. Trop. Dis.* 10, e0004695 under materials and methods.

Plaque assay and plaque reduction neutralization test (PRNT). Virus titres in serum and organs were determined by plaque assay. In brief, BHK-21J cells were seeded overnight at $1\times10^6$ cells per well in a 6-well plate. Virus stock was diluted in 2% assay medium starting from $10^{-1}$ through $10^{-5}$ and 1 mL of each dilution series was added to a well in the 6-well plate that had been washed twice with PBS. Plates were incubated at 37° C. for 1 hour and virus removed thereafter. Agar overlay, prepared in 2% FBS at a concentration of 0.5%, was added to each well and the agar was allowed to solidify at room temperature before incubation at 37° C. for 7 days. Cells were fixed with 4% formaldehyde, washed and plaques were visualized by staining with 1% crystal violet for 5 minutes. Plaques were counted and reported as PFU/mL of virus stock.

Immunofluorescent Assay (IFA)

Virus replication and spread was monitored using an in-house developed IFA. To achieve this, 300 μl of cell suspension derived after trypsinization and resuspension (of transfected cells) in appropriate volume of growth medium was transferred to wells in an 8well Lab-tek chamber slide and stained at indicated time points. Briefly, cells were washed twice with PBS, fixed with 4% paraformaldehyde (PFA) for 20 minutes followed by two washes and permeabilization with 0.1% Triton X-100 for 5 minutes. Cells were then washed twice with PBS and covered with blocking buffer (1% FBS in PBS and 0.05% Tween-20). After 1 hour of incubation at room temperature, blocking buffer was removed and 200 μl of pan-*flavivirus* mouse monoclonal antibody 4G2 (EMD-Millipore) diluted in blocking buffer was added and the slide was rocked on a shaker at 300 rpm for 1 hour. Cells were washed 3 times (5 minutes per wash on a shaker) with wash buffer (PBS+0.05% Tween-20) and counter stained with goat anti-mouse secondary antibody conjugated with a fluorescent probe, Alexa 488, that permits visualization under a fluorescence microscope upon excitation. Secondary antibody was removed and the cells were again washed 3 times (5 minutes per wash on shaker) with wash buffer. Finally, cells were covered with a mounting medium that contained a DAPI stain for nuclear staining (blue) and observed under a fluorescent microscope (Floid Cell Imaging Station, ThermoFisher, Germany).

To determine seroconversion, an in-house IIFA was generated. To this end, Vero E6 cells were infected with the chimeric vaccine virus and incubated for 3 days to allow >95% infection of cells. Cells were then washed, trypsinized, and resuspended in 2% FBS medium. Two hundred (200) μl of cell suspension was transferred to 8-well Lab-tek chamber slides and incubated for 6 hours or overnight prior to the experiment. The infected cells served as antigen for the detection of antibodies in sera of vaccinated mice. All seroconversion studies were done on day 21 post vaccination just before mice were challenged.

Statistical analysis. Data was analysed using GraphPad-Prism software and expressed as mean+/−standard deviation. Comparison of groups was performed using one-way ANOVA, with p values <0.05 indicating a statistical difference between groups.

Example 4

Immunogenicity and Vaccine Efficacy Results in AG129 Mice

Mice were randomly assigned to 2 cages in groups of 5 (n=5). Twenty-one days prior to challenge, one group was vaccinated intraperitoneally (i.p) with $2\times10^4$PFU of YF-ZIKprME and monitored daily for weight loss and signs of disease. No weight loss was observed prior to challenge. On day 21 post vaccination, vaccinated and non-vaccinated mice were challenged i.p with $2\times10^4$PFU of MR766 and monitored daily for weight loss, and visible signs of disease. Vaccinated mice were fully protected from the lethal challenged and were monitored for 28 days post challenge. Non-vaccinated mice on the other hand succumbed to infection and were euthanized, with mean day to euthanasia (MDE) of 14±1. Mice presented with characteristic signs of *flavivirus* infection, namely: hunch posture, sunken eyes, paralysis of hind limbs, and where therefore euthanized.

All vaccinated mice seroconverted and were fully protected from a lethal challenge with $2\times10^4$PFU of MR766. Non-vaccinated mice showed progressive weight loss and signs of disease while the vaccinated mice were protected from weight loss and survived the lethal challenge. We observed a significant difference in mean weight loss (p=0.008) and survival (p=0.0019) between vaccinated and non-vaccinated mice, thanks to the protective efficacy conferred on mice by the YF-ZIKprME vaccine candidate (FIG. 14).

To assess the ability of the vaccine candidate to protect against viremia and viral dissemination to organs, 2 groups of mice (n=5/group) were vaccinated 21 days post challenge. At day 21, mice were challenged with 2×10$^4$PFU of MR766 and 2 control groups of non-vaccinated mice (n=5/group) were equally challenged with same dose of MR766. Five and ten days post challenge, mice were euthanized and organs were harvested for RNA isolation and quantitation by qRT-PCR. Blood was collected by heart puncture, centrifuged and stored at −80° C. for RT extraction and viremia determination. No viremia was detected in 4 out of 5 vaccinated mice by day 5 post challenge, while the non-vaccinated mice showed peak viremia. The mouse with viremia was shown to have <1:2000 antibody titres, opposed to >1:4000 antibody titres in mice with no viremia. Mean viral titres of vaccinated mice were significantly (p=0.0003) lower than non-vaccinated mice. At day 10 post challenge, only 1 out of 5 vaccinated mice showed high viremia comparable to non-vaccinated mice. The remaining 4 vaccinated mice had undetectable viremia. The mouse with high viremia was shown to have no antibody in serum, as a result could not neutralize the challenge virus. Absence of antibodies in this mouse could be due to a failed vaccination or omission to vaccinate, with the latter being more probable. Likewise, successfully vaccinated mice were fully protected from viremia and virus dissemination to organs by the 5 post challenge while non-vaccinated mice presently with viremia and multiple organ infection. By day 10 post challenge, 3 out of 5 vaccinated mice had no virus in blood and organs while 1 mouse had viruses in some organs. The remaining mouse with no seroconversion, as reported earlier, had comparable virus titres in serum and organs as non-vaccinated mice. Taken all together, our results confirm that antibody play a key role to protection and virus neutralization, with the latter markedly dependent on the antibody titres (see FIG. 15).

Example 5

Plaque Assay

Plaque assays were done on BHK-21J cells in 6well plates. To this end, BHK-21J cells were seeded at 1×10$^6$ cells per well and incubated overnight at 37° C., 5% Co2. Serial dilutions of viruses were made starting from 10$^{-1}$ to 10$^{-5}$. As comparators, YF17D and YF-JE (ChimeriVax-JE, chimera between YFV and prME of Japanese encephalitis virus, JEV) were used to decipher, phenotypically, the attenuation of YF-ZIKprME virus. Results revealed that YF-ZIKprME forms markedly smaller plaques when compared to YF17D but showed no marked difference when compared with the attenuated YF-JEprME virus.

Plaque phenotype can be used as proxy for attenuation; in turn, too little attenuation poses an important safety issue for use as live-attenuated vaccine. With that respect YF-ZIKprME shows a similar degree of attenuation as the safe and potent chimeric ChimeriVax-JE (marketed as Imojev® in Australia and South East Asia) as judged by plaque phenotype (see FIG. 10 panel B). Also beneficial is that the new construct does not gain an overt enhanced cytopathogenicity over the parental YFV 17D. The live YFV 17D is considered to be safe as vaccine, it harbour a minimal residual risk of severe adverse side effects, mainly for yellow fever vaccine-associated viscerotropic disease (YEL-AVD) that is a very rare condition (~0.1:100,000) and confined mainly to certain risk groups as discussed by Seligman Vaccine 32:5769-5775). As judged by plaque phenotype YF-ZIKprME is less aggressively growing than YFV 17D and may thus be considered comparably more safe than YFV 17D. Such a favourable safety profile will allow the use of YF-ZIKprME also in more vulnerable populations such young infants, elderly and pregnant women that are contraindicated from YFV 17D vaccination.

TABLE 2

Mutational pattern of synthetic chimeric flaviviruses Chimerivax-JE and novel YF-ZIKprME (YF/ZIKV-ZIK-Canch):

| Virus [construct in FIG. 5] | nucleotide position in YFV | | | | | | | | | |
|---|---|---|---|---|---|---|---|---|---|---|
| | 409 | 1097* | 2343* | 3979 | 3985 | 4025 | 5641 | 7288 | 7319 | 10454 |
| Corresponding position in SEQ ID NO: 1 | 409 | 1097 | 2343 | 4024 | 4030 | 4070 | 5686 | 7333 | 7364 | 10499 |
| Mutation # in FIG. 5 | 3 | 6 | 7 | 4 | 4 | 1 | 8 | 5 | 2 | 9 |
| YFV-17D [I] (WO2014174078) | A | | | T | T | G | A | T | G | G |
| Chimerivax-JE [II] (Arroyo et al. 2001) | A | | | T | T | A | A | A | A | G |
| YF/ZIKprME [IV] (molecular cDNA construct) | G | G | C | G | C | A | A | A | A | G |
| YF/ZIKprME passage 5 [V] | G | R (A, G) # | T | G | C | A | G | A | A | A |
| Amino acid change | — | Ala > Thr | Ser > Leu | — | — | Val > Met | — | — | Glu > Lys | — |
| Codon in SEQ ID NO: 2 | 97 | 327 | 742 | 1302 | 1304 | 1318 | 1856 | 2405 | 2416 | — |

TABLE 2-continued

Mutational pattern of synthetic chimeric flaviviruses Chimerivax-JE and novel YF-ZIKprME (YF/ZIKV-ZIK-Canch):

| Virus [construct in FIG. 5] | nucleotide position in YFV | | | | | | | | | |
|---|---|---|---|---|---|---|---|---|---|---|
| | 409 | 1097* | 2343* | 3979 | 3985 | 4025 | 5641 | 7288 | 7319 | 10454 |
| Genomic region | C | E | E | NS2A | NS2A | NS2A | NS2B | NS4A | NS4B | 3' UTR |

FIG. 5 and Table 2 illustrate the modifications that have been introduced in the different construct disclosed in the present invention.

Construct I is the YFV 17D attenuated strain used in vaccines.

Construct II is the commercial Chimerivax strain wherein the prME genes of YFV are replaced by those of Japanese encephalitis. Herein modifications 1 and 2 have been introduced to increase replication fitness.

Construct (III) is based on (I) as described in (WO2014174078) with the prME sequence of the ZIKV-Yap 2008 strain plus an additionally engineered (translationally silent) mutation 3 to generate a Xho1 restriction site for cloning) This construct was not viable.

Construct (IV) contains the XhoI site (mutation 3) as well as the mutations 1 and 2 of the Chimerivax strain. The introduction of mutation 1 is accompanied with additional mutations 4 to generate a silent BstE2 restriction site.

The introduction of mutation 2 is accompanied with additional mutation 5 to generate a silent Nhe1 restriction site. The construct is viable, yet with poor replication fitness.

Intracellular and extracellular passaging leads to fixation of mutations 6-9 (triangles) in passage 5 (recombinant virus V). This leads to silent nucleotide substitutions as well as amino acid modifications in the Envelope protein of the Zika insert.

The numbering at the top of the table and in FIG. 1 refers to the nucleotides of the yellow fever construct as generally describe in the art. Due to the difference in length of the Zika prME insert of 45 nucleotides, the numbering differs. The numbering of nucleotides as occurring in the chimeric construct of SEQ ID NO:1 and 2 is indicated in the above table and is also indicated within [ ] square brackets in FIG. 1.

Upon sequencing it was encountered that codon 327 is generally mutated leading to an Ala to Thr substitution. Although this substitution is the preferred embodiments, strains where Ala 327 is unmodified are equally envisaged.

In conclusion, a chimeric virus has been generated by replacing the structural genes of YF with those of the heterologous ZIKV. By designing a protocol that permits the propagation of the rather highly attenuated (over-attenuated) chimeric virus, we could successfully grow the virus to higher titres by means of (intracellular) passaging in dividing cells. The virus thus generated formed plaques that were markedly smaller than plaques formed by the parental YFV 17D suggesting that the virus is attenuated in vitro. The chimeric virus also shows an markedly poor growth in mosquito cells suggesting that it will be environmentally safe and has a very low risk to spread via mosquito vectors. The chimeric virus does not cause any signs of ouvert disease anymore in a lethal mouse model of YFV 17D and ZIKV virus infection suggesting that the virus is attenuated in vivo and safe for use as a live vaccine. A single dose of the chimeric virus induces seroconversion to ZIKV specific antibodies and confers within maximum of 21 days after vaccination full protection from a more than 10,000-fold lethal ZIKV challenge when scoring for absence viremia and evidence for infection of relevant target organs, including the brain and the testis. Hence, the chimeric YFV ZIKV virus generated is highly immunogenic and can be used as a safe and efficient live-attenuated vaccine for the prevention of Zika virus infections.

The invention claimed is:

1. A polynucleotide comprising a sequence of a live, infectious, attenuated Yellow Fever-Zika chimeric virus, wherein a nucleotide sequence encoding a signal sequence of a C terminal part of a C protein and a pre-membrane and envelope (prME) protein of the Yellow Fever (YF) virus is replaced by a nucleotide sequence encoding a signal sequence of a C terminal part of a C protein and a prME protein of a Zika virus, so that the signal sequence and the prME protein of the Zika virus are expressed, and wherein an encoded amino acid sequence of the prME protein of the Zika virus differs from a wild type Zika sequence by a Ser742Leu substitution and an Ala327Thr substitution as set forth in SEQ ID NO: 2.

2. The polynucleotide according to claim 1, wherein the signal sequence and the prME protein of the encoded amino acid sequence of the Zika virus has the amino acid sequence set forth in SEQ ID NO: 5.

3. The polynucleotide according to claim 1, wherein:
an encoded amino acid sequence of non-structural protein 2A (NS2A) of the Yellow Fever virus has a Val1318Met substitution as set forth in SEQ ID NO: 2, and/or
an encoded amino acid sequence of non-structural protein 4B (NS4B) of the Yellow Fever virus has a Glu2416Lys substitution as set forth in SEQ ID NO: 2.

4. The polynucleotide according to claim 1, wherein the Yellow Fever virus has a backbone having, as compared with a sequence of Yellow Fever virus vaccine, mutations g4070a, t7333a, and g7364a as set forth in SEQ ID NO: 1.

5. The polynucleotide according to claim 1, wherein the Yellow Fever virus is a Yellow Fever virus vaccine attenuated virus, and wherein the Zika virus is a Yap strain with GenBank accession number EU545988.

6. The polynucleotide according to claim 1, comprising an open reading frame from nucleotide 119 to 10393 set forth in SEQ ID NO: 1 excluding a stop codon, or comprising the nucleotide sequence set forth in SEQ ID NO: 1.

7. The polynucleotide according to claim 1, wherein the nucleotide sequence of the signal peptide of the Zika virus encodes the amino acid sequence set forth in SEQ ID NO: 4.

8. The polynucleotide according to claim 1, wherein the nucleotide sequence at a junction of the C protein of the YF virus and the signal peptide of the Zika virus encodes the amino acid sequence comprising SEQ ID NO: 3.

9. The polynucleotide according to claim 1, which is an Artificial Bacterial Chromosome (BAC).

10. The polynucleotide according to claim 9, wherein the BAC comprises:
an inducible bacterial or sequence for amplification of the BAC to more than 10 copies per bacterial cell, and
a viral expression cassette comprising a cDNA of the Yellow Fever-Zika chimeric virus and comprising cis-regulatory elements for transcription of viral cDNA in mammalian cells and for processing of transcribed RNA into infectious RNA virus.

11. A live, infectious, attenuated Yellow Fever-Zika chimeric virus wherein a signal sequence of a C terminal part of a C protein and a pre-membrane and envelope (prME) protein of the Yellow Fever (YF) virus are replaced by a signal sequence of a C terminal part of a C protein and a prME protein of a Zika virus, wherein an amino acid sequence of the prME protein of the Zika virus differs from a wild type Zika sequence by a Ser742Leu substitution and an Ala327Thr substitution as set forth in SEQ ID NO: 2.

12. The Yellow Fever-Zika chimeric virus according to claim 11, wherein the signal sequence and the prME protein of the Zika virus has the amino acid sequence set forth in SEQ ID NO: 5.

13. The Yellow Fever-Zika chimeric virus according to claim 11, wherein:
an encoded amino acid sequence of non-structural protein 2A (NS2A) of the Yellow Fever virus has a Val1318Met substitution as set forth in SEQ ID NO: 2, and/or
an encoded amino acid sequence of non-structural protein 4B (NS4B) of the Yellow Fever virus has a Glu2416Lys substitution as set forth in SEQ ID NO: 2.

14. The Yellow Fever-Zika chimeric virus according to claim 11, wherein the Yellow Fever Virus is a Yellow Fever virus vaccine attenuated virus, or wherein the Zika virus is a Yap strain with GenBank accession number EU545988.

15. The Yellow Fever-Zika chimeric virus according to claim 11, comprising an amino acid sequence set forth in SEQ ID NO: 4.

16. The Yellow Fever-Zika chimeric virus according to claim 11, wherein the nucleotide sequence at a junction of the C protein of the Yellow Fever virus and the signal peptide of the Zika virus encodes the amino acid sequence set forth in SEQ ID NO: 3.

17. A pharmaceutical composition comprising a polynucleotide sequence encoding a live, infectious, attenuated Yellow Fever-Zika chimeric virus, wherein a nucleotide sequence encoding a signal sequence of a C terminal part of a C protein and a pre-membrane and envelope (prME) protein of the Yellow Fever (YF) virus is replaced by a nucleotide sequence encoding a signal sequence of a C terminal part of a C protein and a prME protein of a Zika virus, so that the signal sequence and prME protein of the Zika are expressed, wherein an encoded amino acid of the prME protein of the Zika virus differs from a wild type Zika sequence by a Ser742Leu substitution and an Ala327Thr substitution as set forth in SEQ ID NO: 2, and a pharmaceutical acceptable carrier.

18. A pharmaceutical composition comprising a live, infectious, attenuated Yellow Fever-Zika chimeric virus wherein a signal sequence of a C terminal part of a C protein and a pre-membrane and envelope (prME) protein of the Yellow Fever (YF) virus are replaced by a signal sequence of a C terminal part of a C protein and a prME protein of a Zika virus, wherein an amino acid sequence of the prME protein of the Zika virus differs from a wild type Zika sequence by a Ser742Leu substitution and an Ala327Thr substitution as set forth in SEQ ID NO: 2, and a pharmaceutical acceptable carrier.

19. A method of inducing a neutralizing antibody response against Zika virus in a subject, thereby preventing an infection by the Zika virus, the method comprising:
administering to the subject a live, infectious, attenuated Yellow Fever-Zika chimeric virus wherein a signal sequence of a C terminal part of a C protein and a pre-membrane and envelope (prME) protein of the Yellow Fever (YF) virus are replaced by a signal sequence of a C terminal part of a C protein and a prME protein of a Zika virus, wherein an amino acid sequence of the prME protein of the Zika virus differs from a wild type Zika sequence by a Ser742Leu substitution and an Ala327Thr substitution as set forth in SEQ ID NO: 2.

20. A method of inducing a neutralizing antibody response against Zika virus in a subject, thereby preventing an infection by the Zika virus, the method comprising:
administering to the subject a polynucleotide comprising a sequence of a live, infectious, attenuated Yellow Fever-Zika chimeric virus wherein a nucleotide sequence encoding a signal sequence of a C terminal part of a C protein and a pre-membrane and envelope (prME) protein of the Yellow Fever (YF) virus is replaced by a nucleotide sequence encoding a signal sequence of a C terminal part of a C protein and a prME protein of a Zika virus, so that the signal sequence and the prME protein of the Zika virus are expressed, wherein an encoded amino acid of the prME protein of the Zika virus differs from a wild type Zika sequence by a Ser742Leu substitution and an Ala327Thr substitution as set forth in SEQ ID NO: 2.

* * * * *